(12) United States Patent
Nakasuji et al.

(10) Patent No.: US 7,888,642 B2
(45) Date of Patent: Feb. 15, 2011

(54) ELECTRON BEAM APPARATUS AND METHOD OF MANUFACTURING SEMICONDUCTOR DEVICE USING THE APPARATUS

(75) Inventors: Mamoru Nakasuji, Kanagawa (JP); Nabuharu Noji, Kanagawa (JP); Tohru Satake, Kanagawa (JP); Masahiro Hatakeyama, Kanagawa (JP); Kenji Watanabe, Kanagawa (JP); Takao Kato, Tokyo (JP); Hirosi Sobukawa, Kanagawa (JP); Tsutomu Karimata, Kanagawa (JP); Shoji Yoshikawa, Tokyo (JP); Toshifumi Kimba, Kanagawa (JP); Shin Oowada, Kanagawa (JP); Mutsumi Saito, Kanagawa (JP); Muneki Hamashima, Kanagawa (JP)

(73) Assignee: Ebara Corporation, Tokyo (JP)

( * ) Notice: Subject to any disclaimer, the term of this patent is extended or adjusted under 35 U.S.C. 154(b) by 241 days.

(21) Appl. No.: 12/188,567

(22) Filed: Aug. 8, 2008

(65) Prior Publication Data

US 2009/0039262 A1    Feb. 12, 2009

Related U.S. Application Data

(60) Division of application No. 11/528,673, filed on Sep. 28, 2006, now Pat. No. 7,423,267, which is a continuation of application No. 10/766,041, filed on Jan. 29, 2004, now Pat. No. 7,129,485, which is a continuation of application No. 09/985,322, filed on Nov. 2, 2001, now Pat. No. 7,095,022.

(30) Foreign Application Priority Data

| Dec. 12, 2000 | (JP) | ............................. 2000-378040 |
| Dec. 21, 2000 | (JP) | ............................. 2000-388385 |
| Jan. 11, 2001 | (JP) | ............................. 2001-3666 |
| Jan. 12, 2001 | (JP) | ............................. 2001-5128 |
| Jan. 26, 2001 | (JP) | ............................. 2001-17901 |
| Jan. 30, 2001 | (JP) | ............................. 2001-21183 |
| Jan. 31, 2001 | (JP) | ............................. 2001-23804 |
| Feb. 2, 2001 | (JP) | ............................. 200126580 |
| Feb. 8, 2001 | (JP) | ............................. 2001-31901 |
| Feb. 8, 2001 | (JP) | ............................. 2001-31906 |
| Feb. 9, 2001 | (JP) | ............................. 2001-33599 |
| Feb. 21, 2001 | (JP) | ............................. 2001-44964 |
| Feb. 27, 2001 | (JP) | ............................. 2001-52095 |
| Mar. 15, 2001 | (JP) | ............................. 2001-73380 |
| Apr. 27, 2001 | (JP) | ............................. 2001-131238 |
| May 28, 2001 | (JP) | ............................. 2001-158571 |

(51) Int. Cl.
*H01J 49/48* (2006.01)
*G21K 5/04* (2006.01)

(52) U.S. Cl. ..................... 250/310; 250/306; 250/307; 250/309

(58) Field of Classification Search .................. None
See application file for complete search history.

(56) References Cited

U.S. PATENT DOCUMENTS 4,431,915 A    2/1984    Nakagawa et al.

(Continued)

OTHER PUBLICATIONS

Sandland; "An Electron-beam inspection system for x-ray mask production", J. of Vacuum Sci. & Tech. B (1991) vol. 9, No. 6; pp. 3005-3009.

(Continued)

*Primary Examiner*—David A Vanore
(74) *Attorney, Agent, or Firm*—Westerman, Hattori, Daniels & Adrian, LLP

(57) ABSTRACT

The present invention provides an electron beam apparatus for irradiating a sample with primary electron beams to detect secondary electron beams generated from a surface of the sample by the irradiation for evaluating the sample surface. In the electron beam apparatus, an electron gun has a cathode for emitting primary electron beams. The cathode includes a plurality of emitters for emitting primary electron beams, arranged apart from one another on a circle centered at an optical axis of a primary electro-optical system. The plurality of emitters are arranged such that when the plurality of emitters are projected onto a straight line parallel with a direction in which the primary electron beams are scanned, resulting points on the straight line are spaced at equal intervals.

9 Claims, 58 Drawing Sheets

U.S. PATENT DOCUMENTS

| | | | |
|---|---|---|---|
| 4,528,451 A | 7/1985 | Petric et al. | |
| 4,726,689 A | 2/1988 | Pollock | |
| 4,864,228 A | 9/1989 | Richardson | |
| 4,912,052 A | 3/1990 | Miyoshi et al. | |
| 5,359,197 A | 10/1994 | Komatsu et al. | |
| 5,892,224 A * | 4/1999 | Nakasuji | 250/310 |
| 5,981,947 A | 11/1999 | Nakasuji et al. | |
| 6,038,018 A * | 3/2000 | Yamazaki et al. | 356/237.1 |
| 6,087,667 A | 7/2000 | Nakasuji et al. | |
| 6,125,522 A | 10/2000 | Nakasuji | |
| 6,465,797 B2 * | 10/2002 | Okunuki | 250/492.3 |
| 6,509,957 B1 | 1/2003 | Tanaka | |
| 6,586,753 B2 | 7/2003 | Wada | |
| 6,593,152 B2 * | 7/2003 | Nakasuji et al. | 438/14 |
| 6,855,929 B2 * | 2/2005 | Kimba et al. | 850/9 |
| 7,109,483 B2 * | 9/2006 | Nakasuji et al. | 250/310 |
| 7,223,973 B2 * | 5/2007 | Kimba et al. | 250/307 |
| 7,244,932 B2 * | 7/2007 | Nakasuji et al. | 250/306 |
| 2002/0020822 A1 | 2/2002 | Okunuki | |
| 2005/0121611 A1 * | 6/2005 | Kimba et al. | 250/311 |
| 2007/0194235 A1 * | 8/2007 | Kimba et al. | 250/310 |
| 2007/0272859 A1 * | 11/2007 | Nakasuji et al. | 250/310 |
| 2008/0173815 A1 * | 7/2008 | Nakasuji et al. | 250/310 |
| 2008/0308729 A1 * | 12/2008 | Kimba et al. | 250/307 |

OTHER PUBLICATIONS

Meisburger et al.; Requirements and performance of an electron-beam column designed for x-ray mask inspection; J. of Vacuum Sci. & Tech. B (1991) vol. 9, No. 6; pp. 3010-3014.

Lischke et al. "Multi-beam concepts for Nanometer Devices"; JP J. Applied Physics (1989) vol. 28, pp. 2058-2064.

Electron/Ion Beam Handbook 2nd; Nikkan Kogyo (1988) pp. 115-119 (with partial English Translation).

* cited by examiner

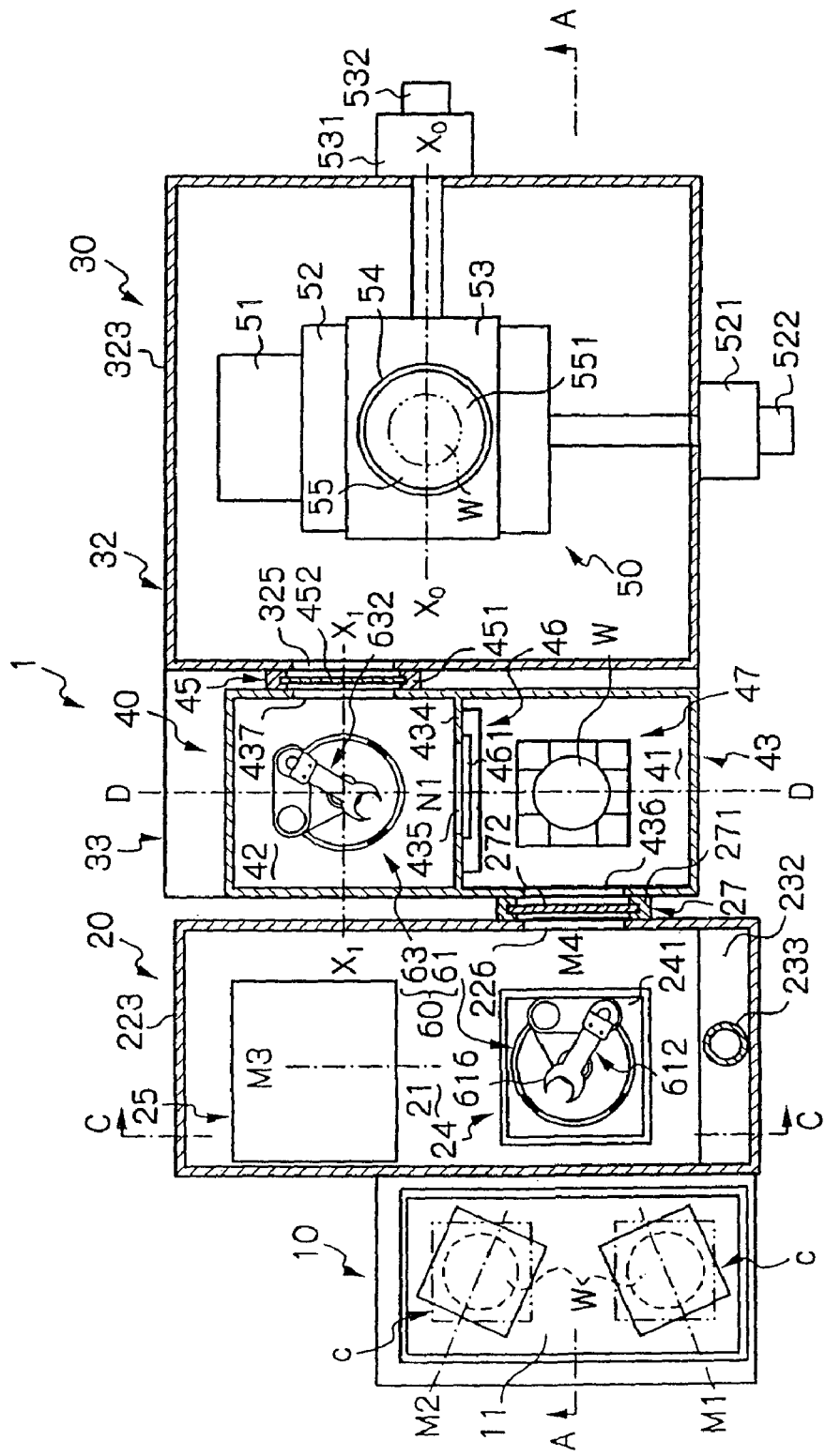

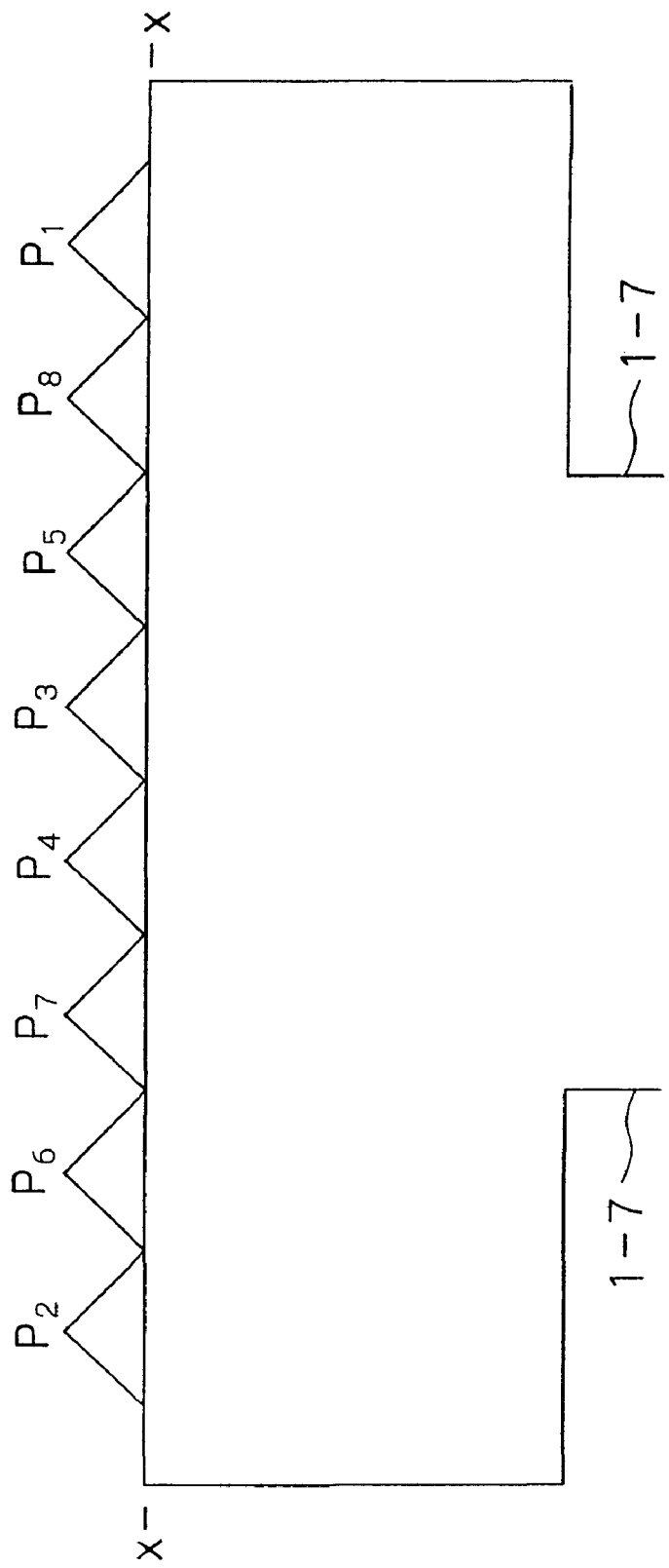

49-10a　　　49-10b

ELECTRON BEAM APPARATUS AND METHOD OF MANUFACTURING SEMICONDUCTOR DEVICE USING THE APPARATUS

This application is a divisional of application Ser. No. 11/528,673, filed Sep. 28, 2006 which is a continuation of application Ser. No. 10/766,041, filed Jan. 29, 2004, which is a continuation of application Ser. No. 09/985,322, filed Nov. 2, 2001 now U.S. Pat. No. 7,095,022.

BACKGROUND OF THE INVENTION

The present invention relates to a technique for testing or inspecting a property or aspect of a sample such as a wafer. In more detail, the present invention relates to an electron beam apparatus applicable to a defect detection and/or line width measurement of a wafer during a semiconductor manufacturing process and so on, in which electron beams are irradiated to a sample, secondary electrons emitted from the sample and varying according to a property of the sample surface are captured, and image data is created therefrom to evaluate patterns on the sample surface with a high throughput on the basis of the image data. The present invention also relates to an evaluation system and a semiconductor device manufacturing method, both of which utilize the electron beam apparatus. In the present description, the meaning of the term "evaluation" of a sample also includes the meaning of "inspection" such as defect detection and line width measurement of a sample.

In semiconductor processes, design rules are now going to enter the era of 100 nm, and the production scheme is shifting from small-kind mass production represented by DRAM to a multi-kind small production such as SOC (silicon on chip). Associated with this shifting, the number of manufacturing steps has been increased, and an improved yield of each process is essential, so that testing for defects caused by the process becomes important.

With the trend of increasingly higher integration of semiconductor devices and finer patterns, a need exists for high resolution, high throughput testing apparatuses. A resolution of 100 nm or less is required for examining defects on a wafer of 100 nm design rule. Also, as manufacturing steps are increased in response to the requirement of higher integration of devices, the amount of testing is increased and thus a higher throughput is required. Further, as devices are formed of an increased number of layers, testing apparatuses are required to have the ability to detect defective contacts (electric defect) of vias which connect lines on layers to each other. While optical defect testing apparatuses are mainly used at present, it is anticipated that electron beam based defect testing apparatuses will substitute for optical defect testing apparatus as a dominant testing apparatus in the future from a viewpoint of the resolution and defective contact testing capabilities. However, the electron beam based defect testing apparatus also has a disadvantage in that it is inferior to the optical one in the throughput. For this reason, a need exists for the development of a high resolution, high throughput electron beam based testing apparatus which is capable of electrically detecting defects.

It is said that the resolution of an optical defect testing apparatus is limited to one half of the wavelength of used light, and the limit is approximately 0.2 μm in an example of practically used optical defect detecting apparatus which uses visible light. On the other hand, in electron beam based systems, scanning electron microscopes (SEM) have been commercially available. The scanning electron microscope has a resolution of 0.1 μm and takes a testing time of eight hours per 20 cm wafer. The electron beam based system also has a significant feature that it is capable of testing electric defects (broken lines, defective conduction of lines, defective conduction of vias, and so on). However, it takes so long testing time that it is expected to develop a defect testing apparatus which can rapidly conduct a test. Further, a testing apparatus is expensive and low in throughput as compared with other process apparatuses, so that it is presently used after critical steps, such as after etching, deposition (including copper coating), CMP (chemical-mechanical polishing) planarization processing, and so on.

A testing apparatus in accordance with an electron beam based scanning (SEM) scheme will be described. An SEM based testing apparatus narrows down an electron beam which is linearly irradiated to a sample for scanning. The diameter of the electron beam corresponds to the resolution. On the other hand, by moving a stage in a direction perpendicular to a direction in which the electron beam is scanned, a region under observation is two-dimensionally irradiated with the electron beam. In general, the width over which the electron beam is scanned, extends over several hundred μm. Secondary electron beams emitted from the sample by the irradiation of the focussed electron beam (called the "primary electron beam") are detected by a combination of a scintillator and a photomultiplier (photomultiplier tube) or a semiconductor based detector (using PIN diodes). The coordinates of irradiated positions and the amount of the secondary electron beams (signal strength) are combined to generate an image which is stored in a storage device or output on a CRT (Braun tube). The foregoing is the principle of SEM (scanning electron microscope). From an image generated by this system, defects on a semiconductor (generally, Si) wafer is detected in the middle of a manufacturing procedure. A detecting speed corresponding to the throughput, is determined by the intensity of a primary electron beam (current value), a size of a pixel, and a response speed of a detector. Currently available maximum values are 0.1 μm for the beam diameter (which may be regarded as the same as the resolution), 100 nA for the current value of the primary electron beam, and 100 MHz for the response speed of the detector, in which case it is said that a testing speed is approximately eight hours per wafer of 20 cm diameter. Therefore, there exists a problem that a testing speed is significantly low in comparison with that in an optical based testing apparatus. For instance, the former testing speed is ¹⁄₂₀ or less of the latter testing speed.

If a beam current is increased in order to achieve a high throughput, a satisfactory SEM image cannot be obtained in the case of a wafer having an insulating membrane on its surface because charging occurs.

As another method for improving an inspection speed, in terms of which an SEM system is poor, there have been proposed SEM systems (multi-beam SEM systems) and apparatuses employing a plurality of electron beams. According to the systems and apparatuses, an inspection speed is improved in proportion to the number of electron beams. However, as a plurality of primary electron beams impinge obliquely on a wafer and a plurality of secondary electron beams are pulled from the wafer obliquely, only secondary electrons released obliquely from the wafer are caught by a detector. Further, a shadow occasionally appears on an image and secondary electrons from a plurality of electron beams are difficult to separate from one another, which disadvantageously results in a mix of the secondary electrons.

Still further, there has been no suggestion or consideration about an interaction between an electron beam apparatus and other sub-systems in an evaluation system employing a multi-beam based electron beam apparatus and thus, at present there aren't any complete evaluation systems of a high throughput. In the meantime, as a wafer to be inspected becomes greater, sub-systems must be re-designed to accommodate to a greater wafer, a solution for which has not yet been suggested either.

SUMMARY OF THE INVENTION

The present invention has been accomplished with a view to obviating the aforementioned problems of prior art and therefore, it is an object of the present invention to provide an evaluation system employing an SEM electron beam apparatus of a multi-beam type and especially an evaluation system capable of improving a throughput of inspection processing.

It is another object of the present invention to provide an SEM electron beam apparatus of a multi-beam type capable of improving not only a throughput of inspection processing but also detection accuracy.

It is still another object of the present invention to provide a method of manufacturing semiconductor devices, according to which a semiconductor wafer can be evaluated by utilizing such an electron beam apparatus or evaluation system as mentioned above irrespective of whether it is in the middle of a fabrication process or upon completion of a fabrication process.

In order to achieve the above objects, the present invention is constituted as follows. That is, a plurality of primary electron beams (multi-beam) are employed to scan a sample in the one-dimensional direction (X direction). The primary electron beams pass through an ExB filter (Wien filter) to impinge perpendicularly upon the surface of the sample, and secondary electrons released from the sample are separated from the primary electron beams by the ExB filter to be pulled obliquely in relation to the axis of the primary electron beams to converge or form an image on a detection system by means of a lens system. Then, a stage is moved in the perpendicular direction (Y direction) with respect to the primary electron beam scanning direction (X direction) to obtain continuous images.

When the primary electron beams pass through the ExB filter, a condition (Wien condition) where the force applied to the electron beams from the electrical field is equal to the force applied from the magnetic field and the directions of the forces are opposite, is set so that the primary electron beams go straight. On the other hand, since the secondary electrons and the primary electron beams advance in the opposite directions, the directions of the forces applied to the secondary electrons from the electrical field and magnetic field are the same and thus, the secondary electrons are deflected from the axial direction of the primary electron beams. As a result, the primary electron beams and secondary electron beams are separated from each other. When electron beams pass through an ExB filter, aberration is larger if the electron beams curve than if the electron beams travel straight. Given that, the optical system of the present invention is designed in such a manner as to cause primary electron beams, which require low aberration, to go straight and cause secondary electron beams, which do not necessarily require low aberration, to deflect.

A detection system of the present invention consists of detectors respectively corresponding to primary electron beams, which are arranged such that a secondary electron deriving from its corresponding primary electron beam impinges on the corresponding detector by means of an image-formation system, whereby interaction of signals, that is, cross-talk can be substantially reduced. As a detector, a combination of a scintillator and a photomultiplier, a PIN diode, etc. may be employed. In the electron beam apparatus according to one embodiment of the present invention, sixteen primary electron beams are employed and a beam current of 20 nA having a beam diameter of 0.1 μm is obtained from each of them and therefore, a value of current obtained from the sixteen electron beams in the electron beam apparatus is three times as great as that obtained from the commercially available apparatus at present.

Further, an electron gun for the electron beam apparatus of the present invention uses a thermal cathode as an electron beam source, and LaB6 is employed as an electron emitting material (emitter). Other materials may be used as long as they have a high melting point (low steam pressure at high temperatures) and small work function. In the present invention, two different ways of providing multiple electron beams are employed. One is to pull one electron beam from an emitter (with one protrusion) and pass the electron beam through a thin plate with a plurality of apertures, thereby obtaining a plurality of electron beams. The other is to provide an emitter with a plurality of protrusions and pull a plurality of electron beams directly from the protrusions. The both ways make use of the properties of an electron beam that an electron beam is more easily emitted from the tip of a protrusion. Electron beams from an electron beam source employing other methods, for example, thermal field emission type electron beams may be employed. A thermal electron beam source uses a system for heating an electron emission material to emit electrons, whereas a thermal field emission electron beam source uses a system for applying a high electric field to an electron emission material to emit electrons and further heating an electron beam emission portion to stabilize electron emission.

BRIEF DESCRIPTION OF THE DRAWINGS

FIG. 6 is an enlarged view of the wafer rack, in which

FIG. 12 illustrates an electron beam calibration mechanism applicable to the electron beam apparatus concerning the present invention, in which

FIG. 40 is an illustration showing that when emitters consisting of the plurality of protrusions shown in FIG. 41 are projected on the X-axis, the protrusions show up at equal spaces;

FIG. 50 shows waveforms representing a signal contrast in the case that electron beams of various beam diameters scan the standard marks by means of the electron beam apparatus shown in FIG. 48;

BEST MODE FOR IMPLEMENTING THE INVENTION

In the following, embodiments of a evaluation system according to the present invention will be described in a case that evaluation samples are semiconductor substrates or wafers having patterns on surfaces thereof. It should be noted that samples other than the wafer are applicable.

Figure 1:
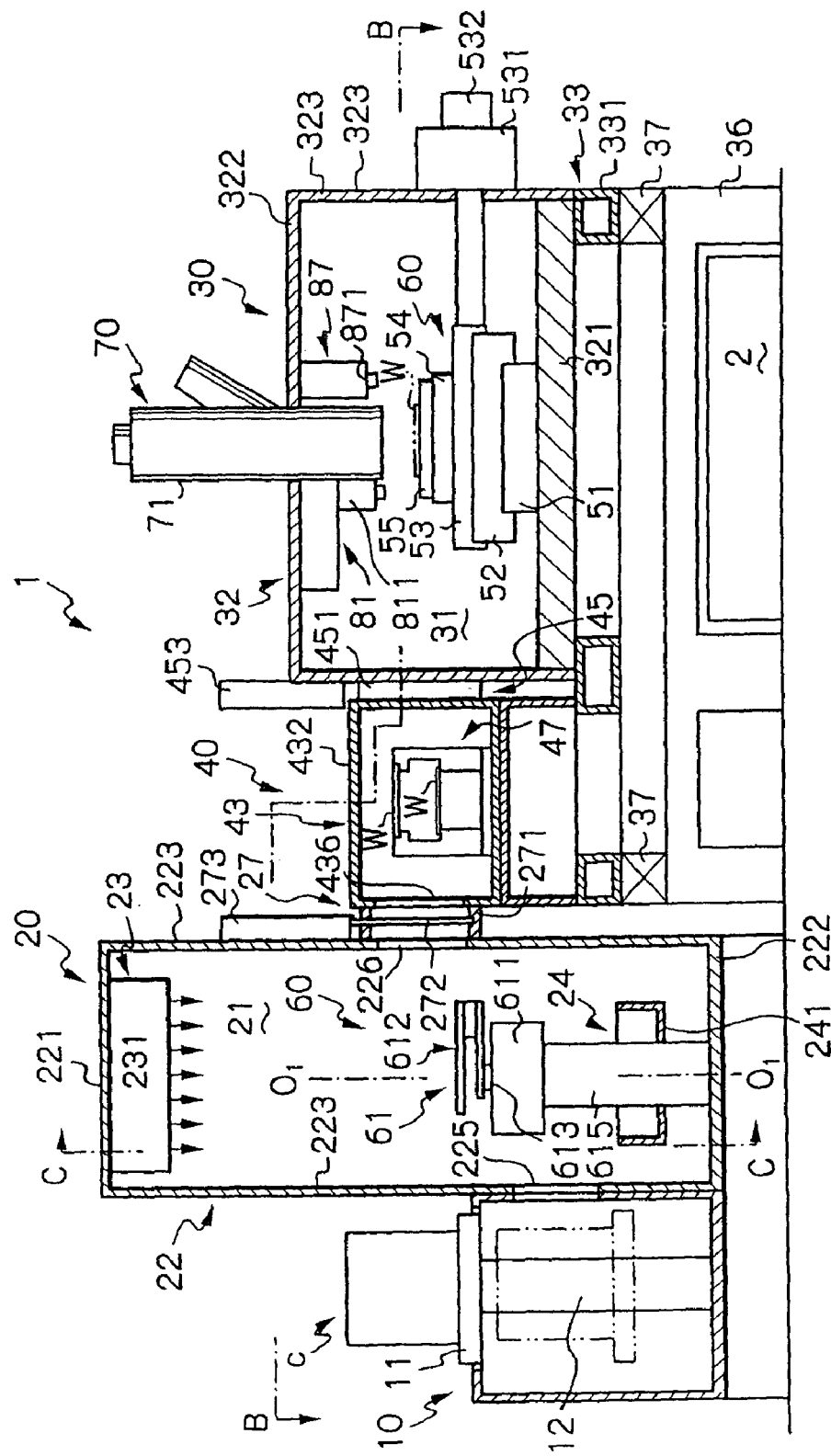
FIG. 1 is an elevation view illustrating major components of an evaluation system according to the present invention.
Figures 1, 50A:
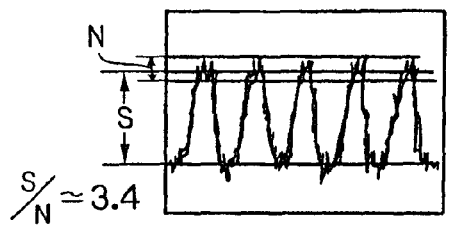
Figures 1, 50B:
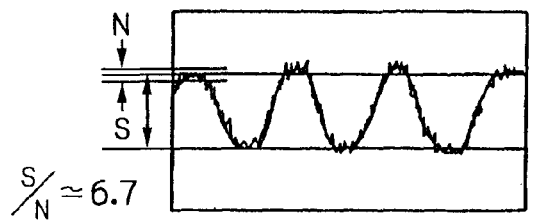
Figures 2, 50A:
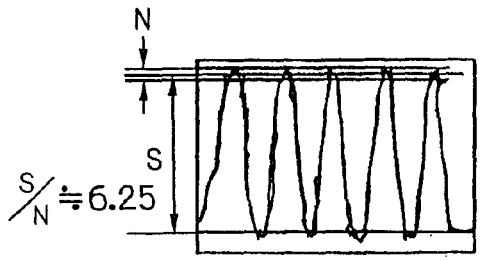
FIG. 2 is a plan view illustrating major components of the evaluation system indicated in FIG. 1 seen from above along the line in B-B in FIG. 1.
Figures 2, 50B:
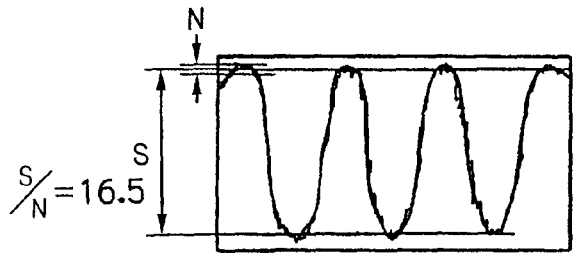
Figures 3, 50A:
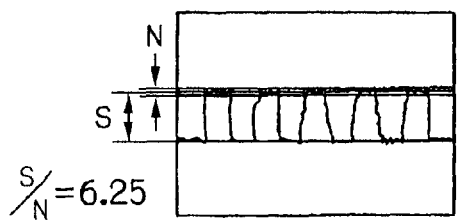
Figures 3, 50B:
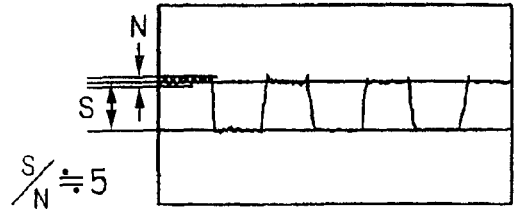

FIGS. 1 and 2 respectively shows a cross-sectional and plan views illustrating main components of evaluation system 1 according to an embodiment of the present invention. The evaluation system 1 comprises a cassette holder 10 for holding a cassette which stores a plurality of wafers; a mini-environment chamber 20; a main housing 30; a loader housing 40 disposed between the mini-environment chamber 20 and the main housing 30 to define two loading chambers; a loader 60 for loading a wafer from the cassette holder 10 (onto a stage apparatus 50 disposed in the main housing 30); the stage apparatus 50 for carrying and moving the wafer W; and an electro-optical system 70 installed in the vacuum main housing 30. These components are arranged in a positional relationship as illustrated in FIGS. 1 and 2. The evaluation system further comprises a pre-charge unit 81 disposed in the vacuum main housing 30; a potential applying mechanism 83 (see in FIG. 11) for applying a wafer with a potential; an electron beam calibration mechanism 85 (see in FIG. 12); and an optical microscope 871 which forms part of an alignment controller 87 for aligning the wafer on the stage apparatus 50.

Constitutions of the main components (sub-system) will next be explained in detail.

Cassette Holder 10

The cassette holder 10 is configured to hold a plurality (two in this embodiment) of cassettes c (for example, closed cassettes such as SMIF, FOUP manufactured by Assist Co.) in which a plurality (for example, twenty-five) wafers are placed side by side in parallel, oriented in the vertical direction. The cassette holder 10 can be arbitrarily selected for installation adapted to a particular loading mechanism. Specifically, when a cassette is automatically loaded into the cassette holder 10 by a robot or the like, the cassette holder 10 having a structure adapted to the automatic loading can be installed. When a cassette is manually loaded into the cassette holder 10, the cassette holder 10 having an open cassette structure can be installed. In this embodiment, the cassette holder 10 is a type adapted to the automatic cassette loading, and comprises, for example, an up/down table 11, and an elevating mechanism 12 for moving the up/down table 11 up and down. The cassette c can be automatically set onto the up/down table 11 in a state indicated by chain lines in FIG. 2. After the setting, the cassette c is automatically rotated to a state indicated by solid lines in FIG. 2 so that it is directed to the axis of pivotal movement of a first carrier unit within the mini-environment chamber 20. In addition, the up/down table 11 is moved down to a state indicated by chain lines in FIG. 1. In this way, since the cassette holder 10 for use in automatic loading, or the cassette holder 10 for use in manual loading may be both implemented by those in known structures, detailed description on their structures and functions are omitted.

Figure 3:
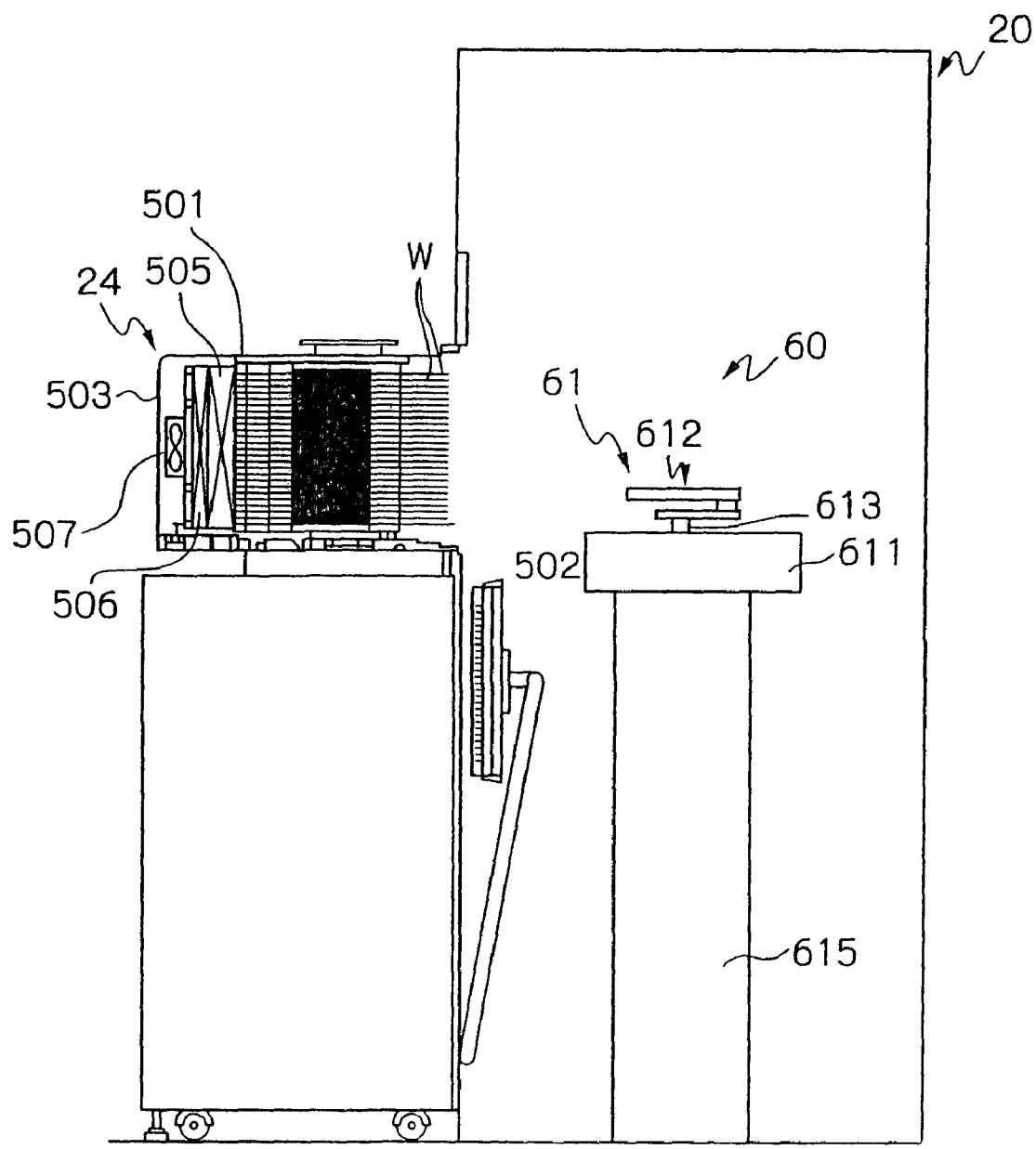
FIG. 3 illustrates a relationship between a wafer transfer chamber and a loader.

FIG. 3 shows a modification to a mechanism for automatically loading a cassette. A plurality of 300 mm wafers W are contained in a slotted pocket (not shown) fixed to the inner surface of a chamber 501 for carriage and storage. This wafer carrying section 24 comprises a chamber 501 of a squared cylinder, a wafer carrying in/out door 502 connected to the chamber 501 and an automatic opening apparatus for a door at a substrate carrying in/out aperture positioned at a side of the chamber 501 and capable of opening and closing mechanically the aperture, a cap 503 positioned in opposite to the aperture for covering an aperture for the purpose of detachably mounting filers and fan motors, and a slotted pocket 507 for holding a wafer W. In this embodiment, the wafers are carried in and out by means of a robot type carrying unit 612 of the loader 60.

It should be noted that wafers accommodated in the cassette c are subjected to testing which is generally performed after a process for processing the wafers or in the middle of the process within semiconductor manufacturing processes. Specifically, accommodated in the cassette are wafers which have undergone a deposition process, CMP, ion implantation and so on; wafers each formed with wiring patterns on the surface thereof; or wafers which have not been formed with wiring patterns. Since a large number of wafers accommodated in the cassette c are spaced from each other in the vertical direction and arranged side by side in parallel, and the first carrier unit has an arm which is vertically movable, a wafer at an arbitrary position can be held by the first carrier unit which will be described later in detail.

Mini-Environment Device 20

Figure 4:
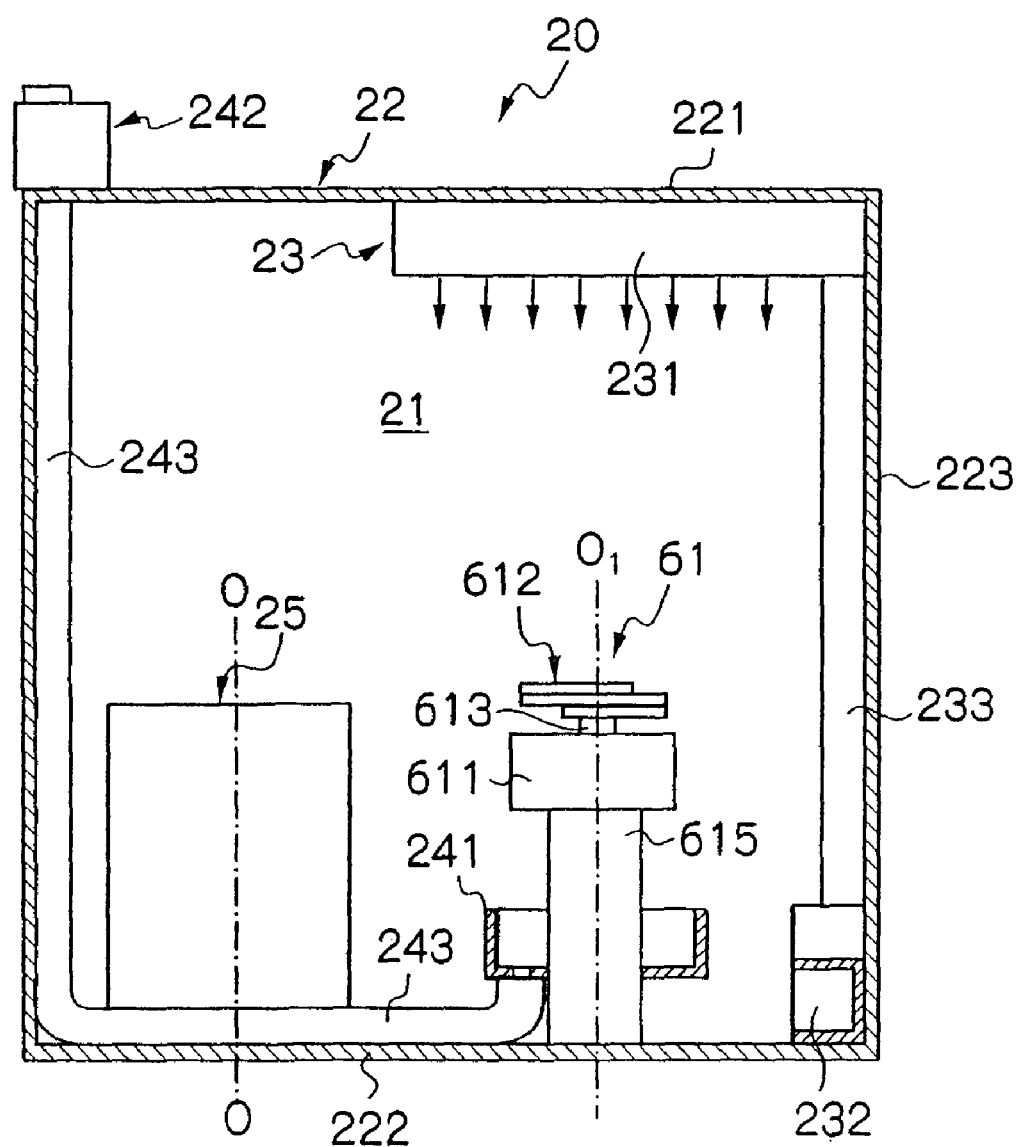
FIG. 4 is a cross section of the mini environment device shown in FIG. 1 taken along the line C-C in FIG. 1.

In FIG. 4 shows an elevation of the mini-environment device 20 in a direction different to that in FIG. 1. As illustrated in FIG. 4 as well as FIGS. 1 and 2, the mini-environment device 20 comprises a housing 22 defining a mini-environment space 21 that is controlled for the atmosphere; a gas circulator 23 for circulating a gas such as clean air within the mini-environment space 21 to execute the atmosphere control; a discharger 24 for recovering a portion of air supplied into the mini-environment space 21 to discharge it; and a prealigner 25 for roughly aligning a sample, i.e., a wafer placed in the mini-environment space 21.

The housing 22 has a top wall 221, bottom wall 222, and peripheral wall 223 which surrounds four sides of the housing 22, to provide a structure for isolating the mini-environment space 21 from the outside. For controlling the atmosphere in the mini-environment space 21, as illustrated in FIG. 4, the gas circulator 23 comprises a gas supply unit 231 attached to the top wall 221 within the mini-environment space 21 for cleaning a gas (air in this embodiment) and delivering the cleaned gas downward through one or more gas nozzles (not shown) in laminar flow; a recovery duct 232 disposed on the bottom wall 222 within the mini-environment space for recovering air which has flown down to the bottom; and a conduit 233 for connecting the recovery duct 232 to the gas supply unit 231 for returning recovered air to the gas supply unit 231.

In this embodiment, the gas supply unit 231 takes about 20% of air to be supplied, from the outside of the housing 22 to clean the air in the mini-environment space 21. However, the percentage of gas taken from the outside may be arbitrarily selected. The gas supply unit 231 comprises an HEPA or ULPA filter in a known structure for creating cleaned air. The laminar down-flow of cleaned air is mainly supplied such that the air passes a carrying surface formed by the first carrier unit (which is described later) disposed within the mini-environment space 21 to prevent particle particles, which could be produced by the carrier unit, from attaching to the wafer. Therefore, the down-flow nozzles need not be positioned near the top wall as illustrated, but is only required to be above the carrying surface formed by the carrier unit. In addition, the air is not supplied over the entire mini-environment space 21. It should be noted that an ion wind may be used as cleaned air to ensure the cleanliness. Also, a sensor may be provided within the mini-environment space 21 for observing the cleanliness such that the apparatus is shut down when the cleanliness is degraded. An access port 225 is formed in a portion of the peripheral wall 223 of the housing 22 that is adjacent to the cassette holder 10. A gate valve in a known structure may be provided near the access port 225 to shut the port from the mini-environment device 20. The laminar down-flow near the wafer may be, for example, at a rate of 0.3 to 0.4 m/sec. The gas supply unit 231 may be disposed outside the mini-environment space 21 instead of within the space.

The discharger 24 comprises a suction duct 241 disposed at a position below the wafer carrying surface of the carrier unit and below the carrier unit; a blower 242 disposed outside the housing 22; and a conduit 243 for connecting the suction duct 241 to the blower 242. The discharger 24 aspires a gas flowing down around the carrier unit and including particle, which could be produced by the carrier unit, through the suction duct 241, and discharges the gas outside the housing 22 through the conduits 243, 244 and the blower 242. In this event, the gas may be discharged into an pumping pipe (not shown) which is laid to the vicinity of the housing 22.

The prealigner 25 disposed within the mini-environment space 21 optically or mechanically detects an orientation flat (which refers to a flat portion formed along the outer periphery of a circular wafer and hereunder called as ori-fla) formed on the wafer, or one or more V-shaped notches formed on the outer peripheral edge of the wafer, and previously aligns the position of the waver in a rotating direction about the axis $O_1$-$O_1$ at an accuracy of approximately ±one degree. The prealigner forms part of a mechanism for determining the coordinates of the wafer, and executes a rough alignment of the wafer. Since the prealigner itself may be of a known structure, explanation on its structure and operation is omitted. Though not shown, a recovery duct for the discharger may also be provided below the prealigner so that air including particle discharged from the prealigner, may be discharged to the outside.

Main Housing 30

As illustrated in FIGS. 1 and 2, the main housing 30 which defines the working chamber 31, comprises a housing body 32 that is supported by a housing supporting device 33 carried on a vibration isolator 37 disposed on a base frame 36. The housing supporting device 33 comprises a frame structure 331 assembled into a rectangular form. The housing body 32 comprises a bottom wall 321 mounted on and securely carried on the frame structure 331; a top wall 322; and a peripheral wall 323 which is connected to the bottom wall 321 and the top wall 322 and surrounds four sides of the housing body 32, thereby isolating the working chamber 31 from the outside. In this embodiment, the bottom wall 321 is made of a relatively thick steel plate to prevent distortion due to the weight of equipment carried thereon such as the stage apparatus 50. Alternatively, another structure may be employed. In this embodiment, each of the housing body 32 and the housing supporting device 33 is assembled into a rigid construction, and the vibration isolator 37 blocks vibrations from the floor, on which the base frame 36 is installed, from being transmitted to the rigid structure. A portion of the peripheral wall 323 of the housing body 32 that adjoins the loader housing 40 is formed with an access port 325 for introducing and removing a wafer.

The vibration isolator may be either of an active type which has an air spring, a magnetic bearing and so on, or a passive type likewise having these components. Since any known structure may be employed for the vibration isolator, description on the structure and functions of the vibration isolator itself is omitted. The working chamber 31 is kept in a vacuum atmosphere by a vacuum system (not shown) in a known structure. A controller 2 for controlling the operation of the overall evacuation system is disposed below the base frame 36.

In the evaluation system 1, some housings including the main housing 30 are kept in vacuum atmosphere. A system for evaporating such a housing comprises a vacuum pump, vacuum valve, vacuum gauge, and vacuum pipes, and evaporates the housing such as an electro-optical system portion, detector portion, wafer housing, load lock housing or the like, in accordance with a predetermined sequence. The vacuum valves are adjusted to kept a required vacuum level of the housings. Further, the vacuum levels are always monitored, and when an abnormal vacuum level is detected, an interlock function enables isolation valves to shut dawn the path between chambers or between a chamber and a pumping system to kept the required vacuum level of the housing. As to the vacuum pump, a turbo-molecular pump can be utilized for main evacuation, and a dry pump of a Roots type can be utilized for rough evacuation. The pressure at a test location (electron beam irradiated region) is $10^{-3}$ to $10^{-5}$ Pa. Preferably, pressure of $10^{-4}$ to $10^{-6}$ Pa is practical.

Loader Housing 40

Figure 5:
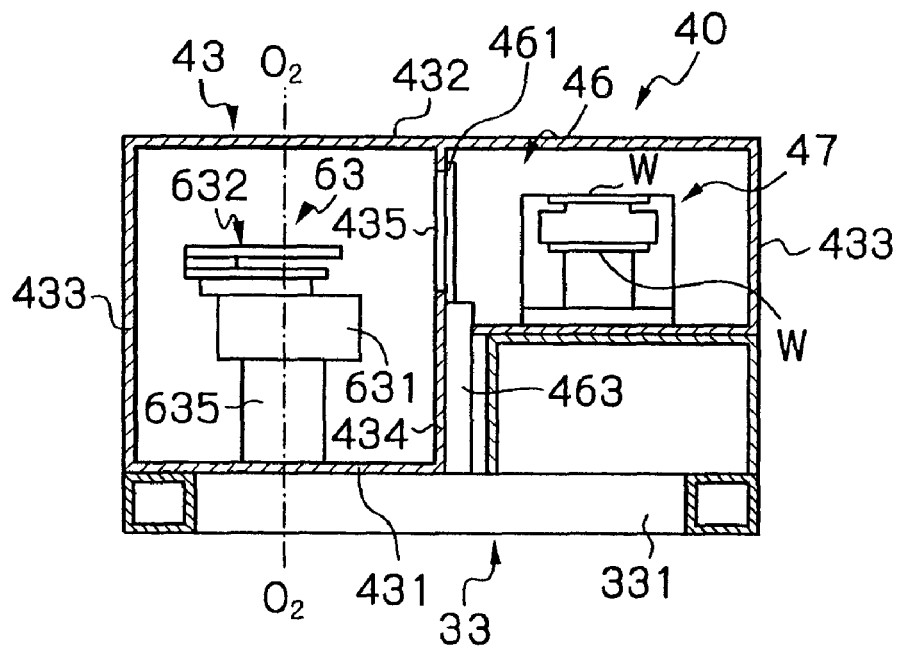
FIG. 5 illustrates the loader housing indicated in FIG. 1 seen along the line D-D in FIG. 2.

FIG. 5 shows an elevation of the loader housing 40, in view of the direction different to that in FIG. 1. As illustrated in FIG. 5 as well as FIGS. 1 and 2, the loader housing 40 comprises a housing body 43 which defines a first loading chamber 41 and a second loading chamber 42. The housing body 43 comprises a bottom wall 431; a top wall 432; a peripheral wall 433 which surrounds four sides of the housing body 43; and a partition wall 434 for partitioning the first loading chamber 41 and the second loading chamber 42 to isolate the two loading chambers from the outside. The partition wall 434 is formed with an aperture, i.e., an access port 435 for passing a wafer W between the two loading chambers. Also, a portion of the peripheral wall 433 that adjoins the mini-environment device 20 and the main housing 30, is formed with access ports 436, 437. The housing body 43 of the loader housing 40 is carried on and supported by the frame structure 331 of the housing supporting device 33. This prevents the vibrations of the floor from being transmitted to the loader housing 40 as well.

The access port 436 of the loader housing 40 is in alignment with the access port 226 of the housing 22 of the mini-environment device 20, and a gate valve 27 is provided for selectively blocking a communication between the mini-environment space 21 and the first loading chamber 41. The gate valve 27 has a sealing member 271 which surrounds the peripheries of the access ports 226, 436 and is fixed to the side wall 433 in close contact therewith; a door 272 for blocking air from flowing through the access ports in cooperation with the sealing material 271; and a driver 273 for moving the door 272. Likewise, the access port 437 of the loader housing 40 is in alignment with the access port 325 of the housing body 32, and a gate valve 45 is provided for selectively blocking a communication between the second loading chamber 42 and the working chamber 31 in a hermetic manner. The gate valve 45 comprises a sealing member 451 which surrounds the peripheries of the access ports 437, 325 and is fixed to side walls 433, 323 in close contact therewith; a door 452 for blocking air from flowing through the access ports in cooperation with the sealing material 451; and a driver 453 for moving the door 452. Further, the opening formed through the partition wall 434 is provided with a gate valve 46 for closing the opening with the door 461 to selectively blocking a communication between the first and second loading chambers in a hermetic manner. These gate valves 27, 45, 46 are configured to provide air-tight sealing for the respective chambers when they are in a closed state. Since these gate valves may be implemented by conventional ones, detailed description on their structures and operations is omitted.

It should be noted that a method of supporting the housing 22 of the mini-environment chamber 20 is different from a method of supporting the loader housing 40. Therefore, for preventing vibrations from being transmitted from the floor through the mini-environment chamber 20 to the loader housing 40 and the main housing 30, a vibration-absorption damper member may be disposed between the housing 22 and the loader housing 40 to provide air-tight sealing for the peripheries of the access ports.

Within the first loading chamber 41, a wafer rack 47 is disposed for supporting a plurality (two in this embodiment) of wafers spaced in the vertical direction and maintained in a horizontal state. As illustrated in FIG. 6, the wafer rack 47 comprises posts 472 fixed at four corners of a rectangular substrate 471, spaced from one another, in an upright state. Each of the posts 472 is formed with supporting devices 473, 474 in two stages, such that peripheral edges of wafers W are carried on and held by these supporting devices. Then, bottoms of arms of the first and second carrier units, later described, are brought closer to wafers from adjacent posts and chuck the wafers.

The loading chambers 41, 42 can be controlled for the atmosphere to be maintained in a high vacuum state (at a vacuum degree of $10^{-5}$ to $10^{-6}$ Pa) by a vacuum evacuator (not shown) in a conventional structure including a vacuum pump, not shown. In this event, the first loading chamber 41 may be held in a low vacuum atmosphere as a low vacuum chamber, while the second loading chamber 42 may be held in a high vacuum atmosphere as a high vacuum chamber, to effectively prevent contamination of wafers. The employment of such a loading housing structure including two loading chambers allows a wafer W to be carried, without significant delay from the loading chamber the working chamber. The employment of such a loading chamber structure provides for an improved throughput for the defect testing, and the highest possible vacuum state around the electron source which is required to be kept in a high vacuum state.

The first and second loading chambers 41, 42 are connected to vacuum pumping pipes and vent pipes for an inert gas (for example, dried pure nitrogen) (neither of which are shown), respectively. In this way, the atmospheric state within each loading chamber is attained by an inert gas vent (which injects an inert gas to prevent an oxygen gas and so on other than the inert gas from attaching on the surface). Since an apparatus itself for implementing the inert gas vent is known in structure, detailed description thereon is omitted.

In the main housing 30 of the invention using electron beams, when representative lanthanum hexaborate ($LaB_6$) used as an electron source for an electro-optical system, later described, is once heated to such a high temperature that causes emission of thermal electrons, it should not be exposed to oxygen within the limits of possibility so as not to shorten the lifetime. In the invention, the exposure to oxygen can be prevented without fail by carrying out the atmosphere control as mentioned above at a stage before introducing the wafer W into the working chamber of the main housing in which the electro-optical system 70 is disposed.

Stage Apparatus 50

The stage apparatus 50 comprises a fixed table 51 disposed on the bottom wall 321 of the main housing 30; a Y-table 52 movable in a Y direction on the fixed table (the direction vertical to the drawing sheet in FIG. 1); an X-table 53 movable in an X direction on the Y-table 52 (in the left-to-right direction in FIG. 1); a turntable 54 rotatable on the X-table; and a holder 55 disposed on the turntable 54. A wafer is releasably held on a wafer carrying surface 551 of the holder 55. The holder 55 may be of a conventional structure which is capable of releasably chucking a wafer by means of a mechanical or electrostatic chuck feature. The stage apparatus 50 uses servo motors, encoders and a variety of sensors (not shown) to operate the above tables to permit highly accurate alignment of a wafer held on the carrying surface 551 by the holder 55 in the X direction, Y direction and Z-direction (the Z-direction is the up-down direction in FIG. 1) with respect to electron beams irradiated from the electro-optical system 70, and in a direction (θ direction) about the axis normal to the wafer supporting surface. The alignment in the Z-direction may be made such that the position on the carrying surface 551 of the holder 55, for example, can be finely adjusted in the Z-direction. In this event, a reference position on the carrying surface is sensed by a position measuring device using a laser of an extremely small diameter (a laser interference range finder using the principles of interferometer) to control the position by a feedback circuit (not shown). Additionally or alternatively, the position of a notch or an orientation flat of a wafer is measured to sense a plane position or a rotational position of the wafer relative to the electron beam to control the position of the wafer by rotating the turntable 54 by a stepping motor which can be controlled in extremely small angular increments. It may be possible to remove the holder 55 and carry a wafer W directly on the rotational table. In order to maximally prevent particle produced within the working chamber, servo motors 531, 531 and encoders 522, 532 for the stage apparatus 50 are disposed outside the main housing 30. Since the stage apparatus 50 may be of a conventional structure used, for example, in steppers and so on, detailed description on its structure and operation is omitted. Likewise, since the laser interference range finder may also be of a conventional one, detailed description on its structure and operation is omitted.

It is also possible to establish a basis for signals which are generated by previously inputting a rotational position, and X-Y-positions of a wafer relative to the electron beams in a signal detecting system or an image processing system, later described. The wafer chucking mechanism provided in the holder 55 is configured to apply a voltage for chucking a wafer to an electrode of an electrostatic chuck, and the alignment is made by pinning three points on the outer periphery of the wafer (preferably spaced equally in the circumferential direction). The wafer chucking mechanism comprises two fixed aligning pins and a push-type clamp pin. The clamp pin can implement automatic chucking and automatic releasing, and constitutes a conducting spot for applying the voltage.

Figures 6A, 6B:
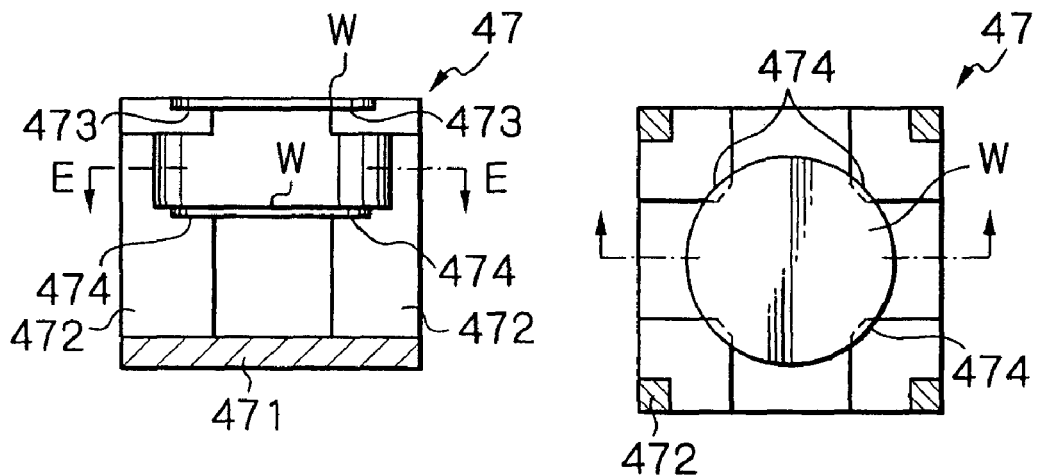
FIG. 6A is a side view thereof and FIG. 6B is a cross section thereof taken along the line E-E in FIG. 6A.

While in this embodiment, the X-table is defined as a table which is movable in the left-to-right direction in FIG. 6(a); and the Y-table as a table which is movable in the up-down direction, a table movable in the left-to-right direction in FIG. 2 may be defined as the Y-table; and a table movable in the up-down direction as the X-table.

Loader 60

The loader 60 comprises a robot-type first carrier unit 61 disposed within the housing 22 of the mini-environment chamber 20; and a robot-type second carrier unit 63 disposed within the second loading chamber 42.

The first carrier unit 61 comprises a multi-node arm 612 rotatable about an axis $O_1$-$O_1$ with respect to a driver 611. While an arbitrary structure may be used for the multi-node arm, the multi-node arm in this embodiment has three parts which are pivotably attached to each other. One part of the arm 612 of the first carrier unit 61, i.e., the first part closest to the driver 611 is attached to a rotatable shaft 613 by a driving mechanism (not shown) of a conventional structure, disposed within the driver 611. The arm 612 is pivotable about the axis $O_1$-$O_1$ by means of the shaft 613, and radially telescopic as a whole with respect to the axis $O_1$-$O_1$ through relative rotations among the parts. At a bottom of the third part of the arm 612 furthest away from the shaft 613, a chuck 616 in a conventional structure for chucking a wafer, such as a mechanical chuck or an electrostatic chuck, is disposed. The driver 611 is movable in the vertical direction by an elevating mechanism 615 of a conventional structure.

The first carrier unit 61 extends the arm 612 in either a direction M1 or a direction M2 (FIG. 2) within two cassettes c held in the cassette holder 10, and removes a wafer accommodated in a cassette c by carrying the wafer on the arm or by chuck bing the wafer with the chuck (not shown) attached at the bottom of the arm. Subsequently, the arm is retracted (in a state as illustrated in FIG. 2), and then rotated to a position at which the arm can extend in a direction M3 toward the prealigner 25, and stopped at this position. Then, the arm is again extended to transfer the wafer held on the arm to the prealigner 25. After receiving a wafer from the prealigner 25, contrary to the foregoing, the arm is further rotated and stopped at a position at which it can extend to the second loading chamber 41 (in the direction M4), and transfers the wafer to a wafer receiver 47 within the second loading chamber 41. For mechanically chuck bing a wafer, the wafer should be chuck bed on a peripheral region (in a range of approximately 5 mm from the peripheral edge). This is because the wafer is formed with devices (circuit patterns) over the entire surface except for the peripheral region, and chuck bing the inner region would result in failed or defective devices.

The second carrier unit 63 is basically identical to the first carrier unit 61 in structure except that the second carrier unit 63 carries a wafer between the wafer rack 47 and the carrying surface of the stage apparatus 50, so that detailed description thereon is omitted.

Each of the first and second carrier units 61, 63 carry a wafer from a cassette held in the cassette holder 10 to the stage apparatus 50 disposed in the working chamber 31 and vice versa, while remaining substantially in a horizontal state. The arms of the carrier units 61, 63 are moved in the vertical direction only when a wafer is removed from and inserted into a cassette, when a wafer is carried on and removed from the wafer rack, and when a wafer is carried on and removed from the stage apparatus 50. It is therefore possible to smoothly carry a larger wafer, for example, a wafer having a diameter of 30 cm.

Next, how a wafer is carried will be described in sequence from the cassette c held by the cassette holder 10 to the stage apparatus 50 disposed in the working chamber 31.

As described above, when the cassette is manually set, the cassette holder 10 having a structure adapted to the manual setting is used, and when the cassette is automatically set, the cassette holder 10 having a structure adapted to the automatic setting is used. In this embodiment, as the cassette c is set on the up/down table 11 of the cassette holder 10, the up/down table 11 is moved down by the elevating mechanism 12 to align the cassette c with the access port 225. As the cassette is aligned with the access port 225, a cover (not shown) provided for the cassette is opened, and a cylindrical cover is applied between the cassette c and the access port 225 of the mini-environment to block the cassette and the mini-environment space 21 from the outside. Since these structures are known, detailed description on their structures and operations is omitted. When the mini-environment device 20 is provided with a gate valve for opening and closing the access port 225, the gate valve is operated to open the access port 225.

On the other hand, the arm 612 of the first carrier unit 61 remains oriented in either the direction M1 or M2 (in the direction M1 in this description). As the access port 225 is opened, the arm 612 extends to receive one of wafers accommodated in the cassette at the bottom. While the arm and a wafer to be removed from the cassette are adjusted in the vertical position by moving up or down the driver 611 of the first carrier unit 61 and the arm 612 in this embodiment, the adjustment may be made by moving up and down the up/down table 11 of the cassette holder 10, or made by both.

As the arm 612 has received the wafer, the arm 621 is retracted, and the gate valve is operated to close the access port (when the gate valve is provided). Next, the arm 612 is pivoted about the axis $O_1$-$O_1$ such that it can extend in the direction M3. Then, the arm 612 is extended and transfers the wafer carried at the bottom or chucked by the chuck onto the prealigner 25 which aligns the orientation of the rotating direction of the wafer (the direction about the central axis vertical to the wafer plane) within a predetermined range. Upon completion of the alignment, the carrier unit 61 retracts the arm 612 after a wafer has been received from the prealigner 25 to the bottom of the arm 612, and takes a posture in which the arm 612 can be extended in a direction M4. Then, the door 272 of the gate valve 27 is moved to open the access ports 223, 236, and the arm 612 is extended to place the wafer on the upper stage or the lower stage of the wafer rack 47 within the first loading chamber 41. It should be noted that before the gate valve 27 opens the access ports to transfer the wafer to the wafer rack 47, the opening 435 formed through the partition wall 434 is closed by the door 461 of the gate valve 46 in an air-tight state.

In the process of carrying a wafer by the first carrier unit, clean air flows (as down flows) in laminar flow from the gas supply unit 231 disposed on the housing of the mini-environment chamber to prevent particle from attaching on the upper surface of the wafer during the carriage. A portion of the air near the carrier unit (in this embodiment, about 20% of the air supplied from the supply unit 231, mainly contaminated air) is aspired from the suction duct 241 of the discharger 24 and discharged outside the housing. The remaining air is recovered through the recovery duct 232 disposed on the bottom of the housing and returned again to the gas supply unit 231.

As the wafer is placed into the wafer rack 47 within the first loading chamber 41 of the loader housing 40 by the first carrier unit 61, the gate valve 27 is closed to seal the loading chamber 41. Then, the first loading chamber 41 is filled with an inert gas to expel air. Subsequently, the inert gas is also evacuated so that a vacuum atmosphere dominates within the loading chamber 41. The vacuum atmosphere within the loading chamber 41 may be at a low vacuum degree. When a certain degree of vacuum is provided within the loading chamber 41, the gate valve 46 is operated to open the access port 434 which has been sealed by the door 461, and the arm 632 of the second carrier unit 63 is extended to receive one wafer from the wafer receiver 47 with the chuck at the bottom (the wafer is carried on the bottom or chuck bed by the chuck attached to the bottom). Upon completion of the receipt of the wafer, the arm 632 is retracted, followed by the gate valve 46 again operated to close the access port 435 by the door 461. It should be noted that the arm 632 has previously taken a posture in which it can extend in the direction N1 of the wafer rack 47 before the gate valve 46 is operated to open the access port 435. Also, as described above, the access ports 437, 325 have been closed by the door 452 of the gate valve 45 before the gate valve 46 is operated to block the communication between the second loading chamber 42 and the working chamber 31 in an air-tight state, so that the second loading chamber 42 is evacuated.

As the gate valve 46 is operated to close the access port 435, the second loading chamber 42 is again evacuated at a higher degree of vacuum than the first loading chamber 41. Meanwhile, the arm 632 of the second carrier unit 63 is rotated to a position at which it can extend toward the stage apparatus 50 within the working chamber 31. On the other hand, in the stage apparatus 50 within the working chamber 31, the Y-table 52 is moved upward, as viewed in FIG. 2, to a position at which the center line $O_0$-$O_0$ of the X-table 53 substantially matches an X-axis $X_1$-$X_1$ which passes a pivotal axis $O_2$-$O_2$ of the second carrier unit 63. The X-table 53 in turn is moved to the position closest to the leftmost position in FIG. 2, and remains awaiting at this position. When the second loading chamber 42 is evacuated to substantially the same degree of vacuum as the working chamber 31, the door 452 of the gate valve 45 is moved to open the access ports 437, 325, allowing the arm 632 to extend so that the bottom of the arm 632, which holds a wafer, approaches the stage apparatus 50 within the working chamber 31. Then, the wafer is placed on the carrying surface 551 of the stage apparatus 50. As the wafer has been placed on the carrying surface 551, the arm 632 is retracted, followed by the gate 45 operated to close the access ports 437, 325.

The foregoing description has been made on the operation until a wafer in the cassette c is carried and placed on the stage apparatus 50. For returning a wafer, which has been carried on the stage apparatus 50 and processed, from the stage apparatus 50 to the cassette c, the operation reverse to the foregoing is performed. Since a plurality of wafers are stored in the wafer rack 47, the first carrier unit 61 can carry a wafer between the cassette and the wafer rack 47 while the second carrier unit 63 is carrying a wafer between the wafer rack 47 and the stage apparatus 50, so that the testing operation can be efficiently carried out.

Specifically, if an already-processed wafer A and a unprocessed wafer B are placed on the wafer rack 47 of the second carrier unit, (1) the unprocessed wafer B is moved to the stage apparatus 50 and a process for the wafer B starts. In the middle of this process, (2) the processed wafer A is moved to the wafer rack 47 from the stage apparatus 50. A unprocessed wafer C is likewise extracted from the wafer rack 47 by the arm and is aligned by the pre-aligner. Then, the wafer C is moved to the wafer rack of the loading chamber 41. By doing so, it is possible to replace the wafer A with the unprocessed wafer C in the wafer rack 47 during the wafer B is being processed.

Depending upon how such an apparatus for performing a test or evaluation is utilized, a plurality of the stage apparatus 50 can be disposed to cause a wafer to be transferred from one wafer rack 47 to each stage apparatus, making it possible to process a plurality of wafers in a similar manner.

Figure 7A:
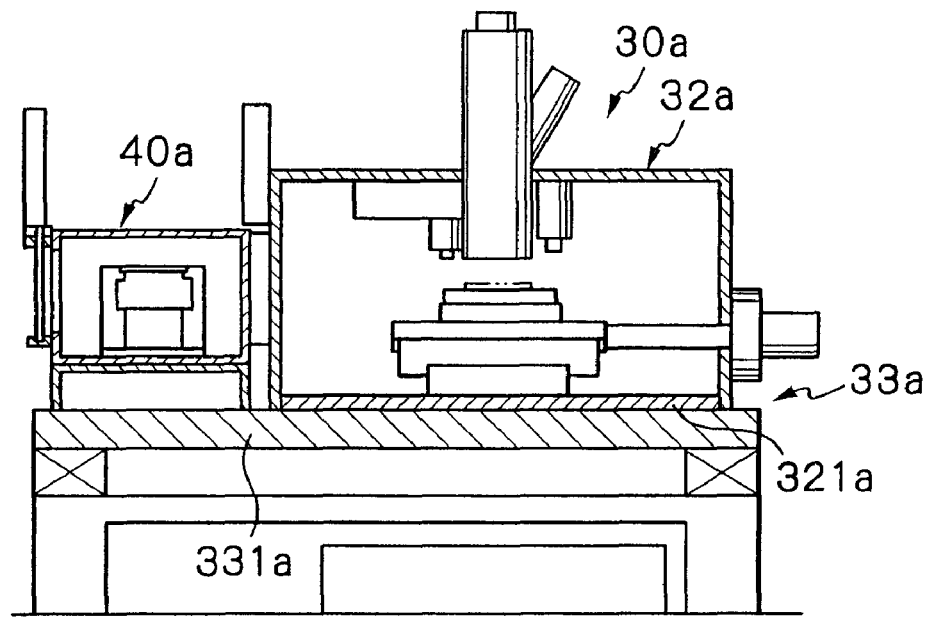
FIG. 7 illustrates a variation of a method of supporting a main housing.
Figure 7B:
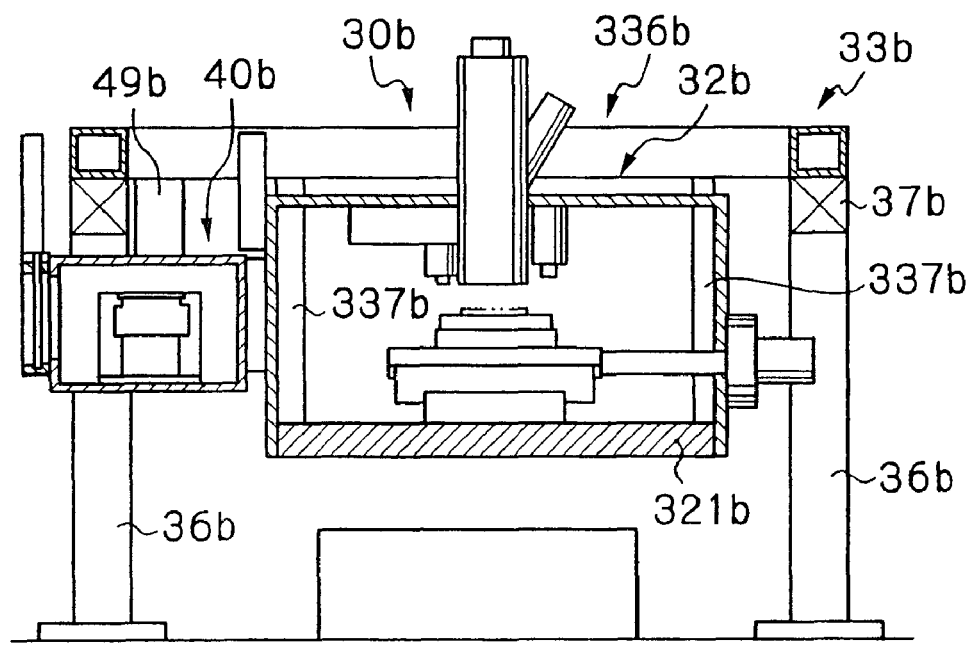

FIGS. 7A and 7B illustrate an exemplary modification to the method of supporting the main housing 30. In an exemplary modification illustrated in FIG. 7A, a housing supporting device 33a is made of a thick rectangular steel plate 331a, and a housing body 32a is carried on the steel plate. Therefore, the bottom wall 321a of the housing body 32a is thinner than the bottom wall 222 of the housing body 32 in the foregoing embodiment. In an exemplary modification illustrated in FIG. 7B, a housing body 32b and a loader housing 40b are suspended by a frame structure 336b of a housing supporting device 33b. Lower ends of a plurality of vertical frames 337b fixed to the frame structure 336b are fixed to four corners of a bottom wall 321b of the housing body 32b, such that the peripheral wall and the top wall are supported by the bottom wall. A vibration isolator 37b is disposed between the frame structure 336b and a base frame 36b. Likewise, the loader housing 40 is suspended by a suspending member 49b fixed to the frame structure 336. In the exemplary modification of the housing body 32b illustrated in FIG. 7B, the housing body 32b is supported in suspension, the general center of gravity of the main housing and a variety of devices disposed therein can be brought downward. The methods of supporting the main housing and the loader housing are configured to prevent vibrations from being transmitted from the floor to the main housing and the loader housing.

In another exemplary modification, not shown, the housing body of the main housing is only supported by the housing supporting device from below, while the loader housing may be placed on the floor in the same way as the adjacent mini-environment chamber. Alternatively, in a further exemplary modification, not shown, the housing body of the main housing is only supported by the frame structure in suspension, while the loader housing may be placed on the floor in the same way as the adjacent mini-environment device.

Electro-Optical System 70

The electro-optical system 70 comprises a column or column 71 fixed on the housing body 32. Disposed within the column 71 are an electro-optical system comprised of a primary electro-optical system (hereinafter simply called the "primary optical system") and a secondary electro-optical system (hereinafter simply called the "secondary optical system"), and a detecting system.

Figure 8:
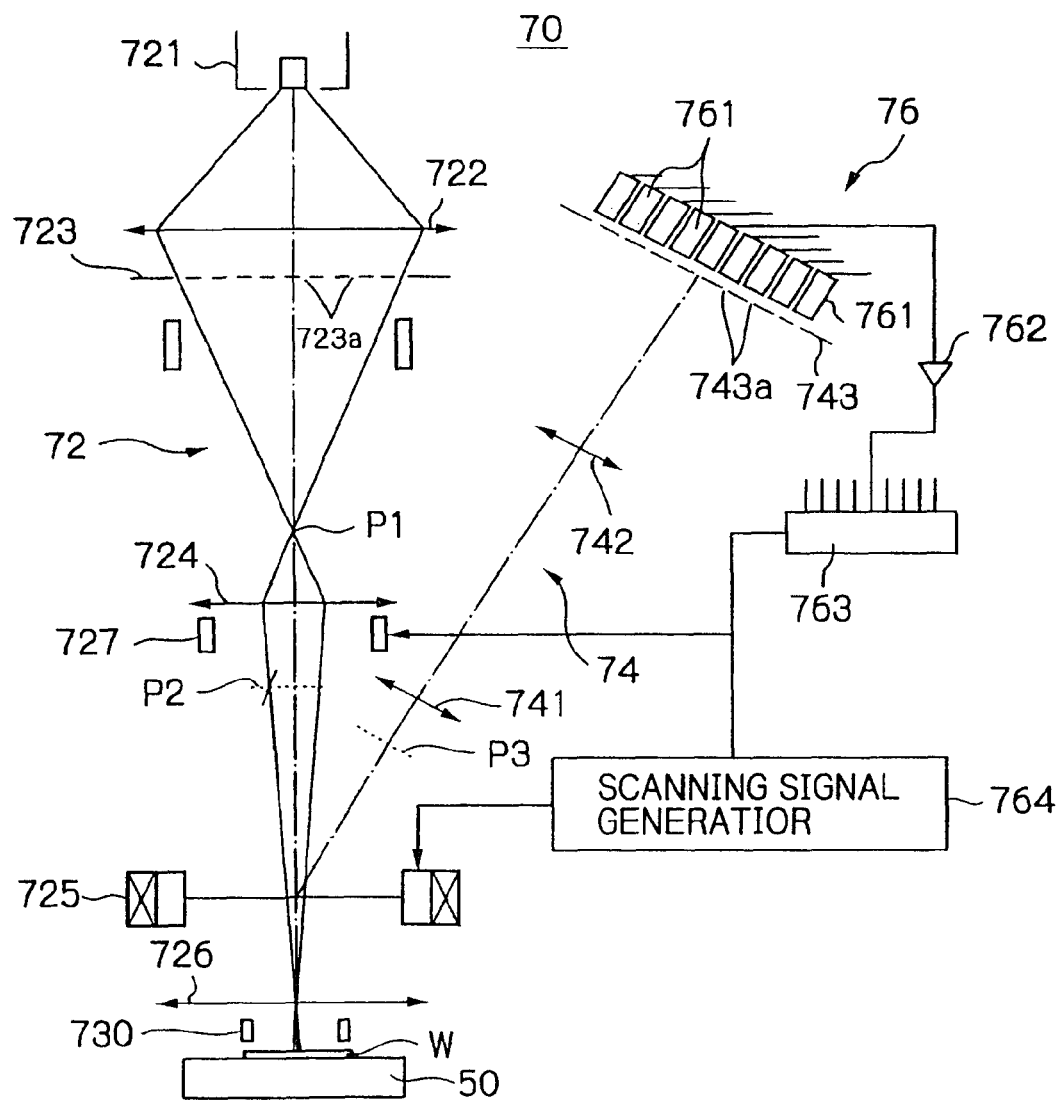
FIG. 8 schematically illustrates an embodiment of an electron beam apparatus concerning the present invention, which can be applied to the evaluation system indicated in FIG. 1.

FIG. 8 shows an embodiment of the electro-optical system 70. In the drawing, 72 denotes a primary optical system, 74 a secondary optical system and 76 a detecting system. FIG. 8 also illustrates a stage apparatus 50 carrying a wafer W and a scanning signal generation circuit 764 which is a part of a control apparatus. The primary optical system 72 irradiates the surface of the sample or wafer W with electron beams, and comprises an electron gun 721 for emitting an electron beam(s); a condenser lens 722 comprised of an electrostatic lens for converging the primary the electron beam emitted from the electron gun 721; a multi-aperture plate 723 located below the condenser lens 722 and having a plurality of apertures, for forming a plurality of primary electron beams or multi-beams from the primary electron beam from the gun 721; a reducing lens 724 comprised of an electrostatic lens for reducing the primary electron beams; a Wien filter or an ExB separator or deflector 725; and an objective lens 726. These components are arranged in order with the electron gun 721 placed at the top, as illustrated in FIG. 8, and settled such that the optical axes of the electron beams irradiated are orthogonal to the surface of the wafer W.

Figure 9A:
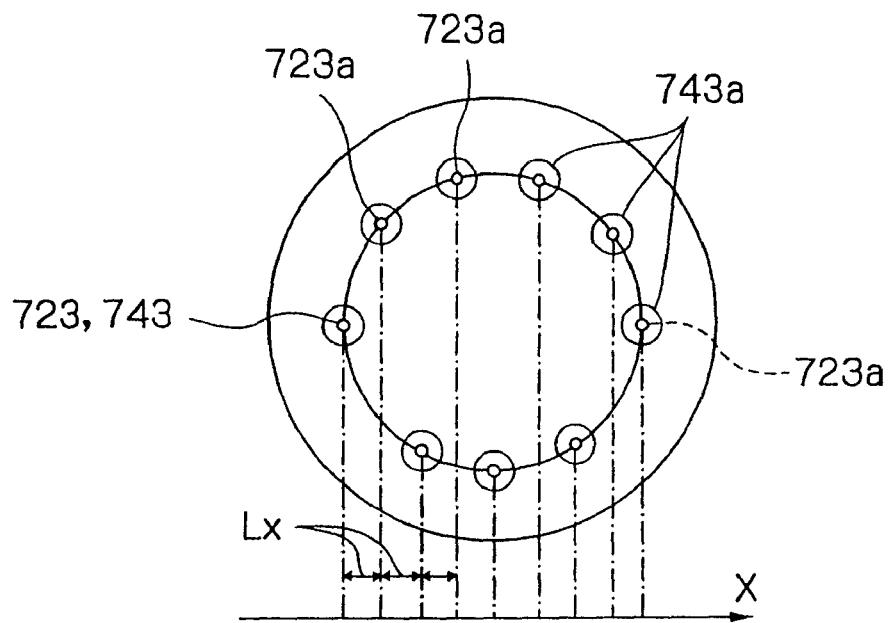
FIG. 9A illustrates an arrangement of apertures bored on a multi-aperture plate used in primary and secondary optical systems of the electron beam apparatus shown in FIG. 8.

In order to reduce aberration effect of field curvature by the reducing lens 724 and objective lens 726, the multi-apertures 723a (9 apertures in this embodiment) are positioned through the multi-aperture plate 723 such that when the apertures are projected on the X-axis, the distance Lx between the adjacent points on the X-axis is equal, as shown in FIG. 9A.

The secondary optical system 74 comprises magnification lenses 741, 742 each comprised of an electrostatic lens which pass secondary electrons separated from the primary optical system by an ExB deflector 725; and a multi-aperture plate 743. A plurality of apertures 743a of the multi-aperture plate 743 are located such that they coincide, one by one, with the apertures 723a of the multi-aperture plate 723 of the primary optical system, as illustrated in FIG. 9A.

The detecting system 76 comprises a plurality of detectors 761 (9 detectors in this embodiment) the number of which is equal to that of the apertures 743a of the multi-aperture plate 743 of the secondary optical system 74 and located correspondingly thereto; and an image processing section 763 connected through A/D converters 762. The image processing section 763 is not necessary to physically located in the electro-optical system 70.

Next, the operation of the electro-optical system 70 configured as described above will be described. The primary electron beam emitted from the electron gun 721 is converged by the condenser lens 722 to form a cross-over at a point P. The primary electron beam which has been converged by the condenser lens 722 passes through the apertures 723a of the multi-aperture plate 723, resulting in that a multiple electron beams are created. Each of the multi-electron beams is then reduced by the reducing lens 724 and projected at a point P2. After the focussing at the point P2, the beam passes the objective lens 726 to focus on the surface of the wafer W. In this situation, the primary electron beams are deflected by a deflector 727 located between the reducing lens 724 and the objective lens 726 to be scanned on the surface of the wafer W. The deflector 727 deflects the primary electron beams in response to a scanning signal applied thereto.

Figure 9B:
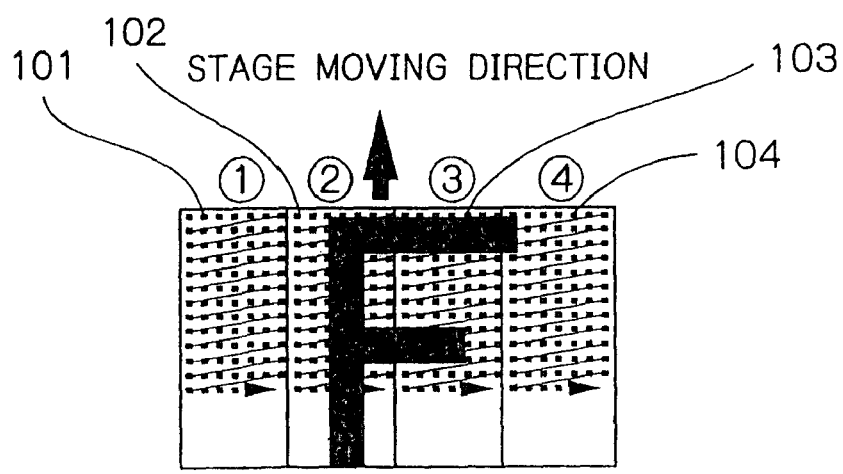
FIG. 9B depicts a mode of primary electron beam scanning.

A method of irradiating primary electron beams by the primary optical system 72 will next be explained, with reference to FIG. 9B. In the example of FIG. 9B, in order to make explanation brief, four primary electron beams 101, 102, 103, 104 are employed. It is assumed that each of the electron beams is scanned by 50 μm width. As to the beam 101, it scans in the right direction from the left end, returns to the left end immediately after reaching the right end, and again scans in the right direction. Since the four electron beams scan simultaneously on a wafer surface, a throughput can be improved.

Returning to FIG. 8, a plurality of points on the wafer W are illuminated by a plurality of focussed primary electron beams (nine beams in the embodiment in FIG. 8), resulting in that secondary electrons are emitted from the illuminated points. The secondary electrons are then converged by pulling the electric field created by the objective lens, deflected by the ExB separator 725 to be directed to the secondary optical system 74. An image created by the secondary electrons are focussed at a point P3 which is closer than the point P2. This is because a primary electron has energy of about 500 eV and the secondary electron has energy of only several eV.

Figure 10A:
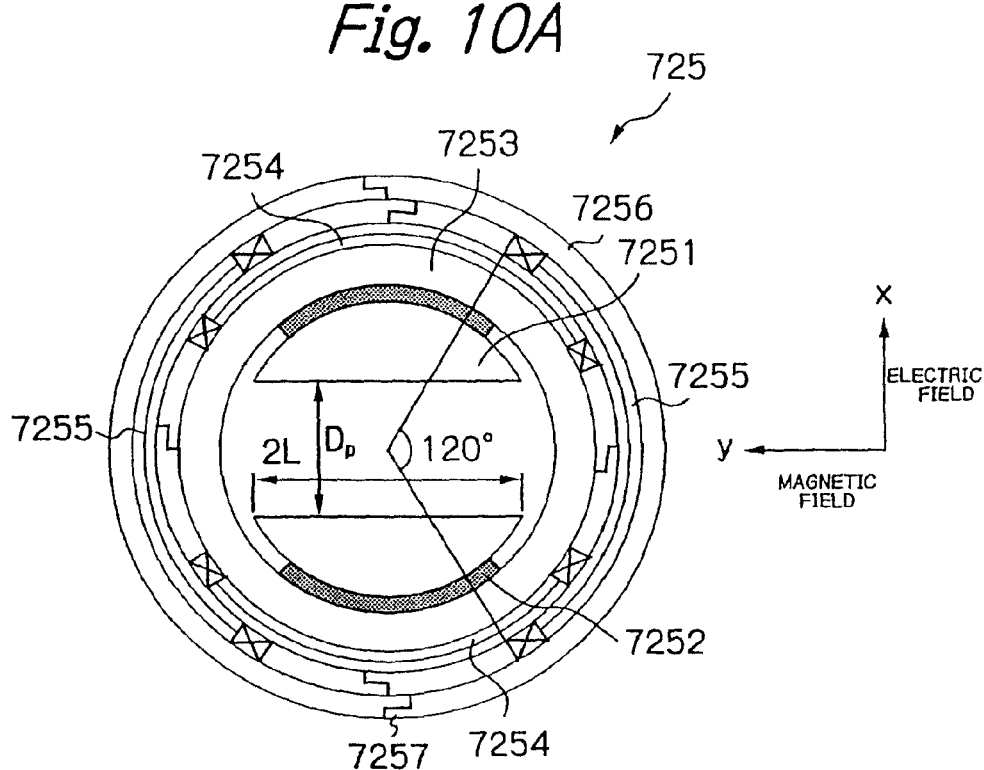
FIGS. 10A and 10B illustrate embodiments of an ExB separator applicable to the electron beam apparatus concerning the present invention.

It will be explained the ExB separator 725 with reference to FIG. 10. FIG. 10A illustrates an example of the ExB separator applicable to the electro-optical apparatus according to the present invention. The ExB separator comprises an electrostatic deflector and electromagnetic deflector. FIG. 10 shows a cross sectional view in X-Y plane perpendicular to an optical axis (perpendicular to the drawing surface) OA1. The X and Y-axes are perpendicular to each other.

The electro-static deflector has a pair of electrodes (electro-static deflection electrodes) 7251 in a vacuum to create a electric field in the X direction. The electro-static deflection electrodes 7251 are mounted on an inside wall 7253 of the vacuum via isolation spacers 7252, the distance Dp therebetween is set to be smaller than a length 2 L of the electro-static deflection electrodes in the Y direction. By setting the above, a range where a strength of the electric field around the Z-axis or the optical axis is substantially constant may be made wide. However, ideally, it is better to set Dp<L to create a more wider range having a constant strength electric field.

In particular, the strength of the electric field is not constant in a range of Dp/2 from the end of the electrode. Therefore, the range where a strength of the electric field is constant is represented by 2 L-Dp which is a center portion of the electrode, excluding the non-constant regions. Accordingly, in order to create a range where the strength electric field is constant, it is necessary to settle to satisfy 2 L>Dp, and it is more preferable to set L>Dp to create a broader range thereof. The electromagnetic deflector for creating a magnetic field in the Y direction is provided outside the vacuum wall 7253. The electromagnetic deflector comprises electromagnetic coils 7254, 7255, which generate magnetic fields in the X and Y directions. Although only the coil 7255 can provide the magnetic field in the Y direction, the coil for generating the magnetic field in the X direction is also provided to improve the perpendicular character between the electric and magnetic fields. Namely, the component in the −X direction of the magnetic field created by the coil 7254 cancels the component in the +X direction created by the coil 7255 to obtain the improved perpendicular character between the electric and magnetic fields.

Each of the coils for generating the magnetic field consists of two parts to be installed outside the vacuum wall, which are mounted on the surface of the vacuum wall 7253 from the both sides thereof, and fixedly clamped at portions 7257 with screws or the like.

The most outer layer 7256 of the ExB separator is formed as yokes made of Permalloy or ferrite. The most outer layer 7256 consists of two parts, and are mounted on the outer surface of the coil 7255 and fixedly clamped at portions 7257 with screws or the like.

Figure 10B:
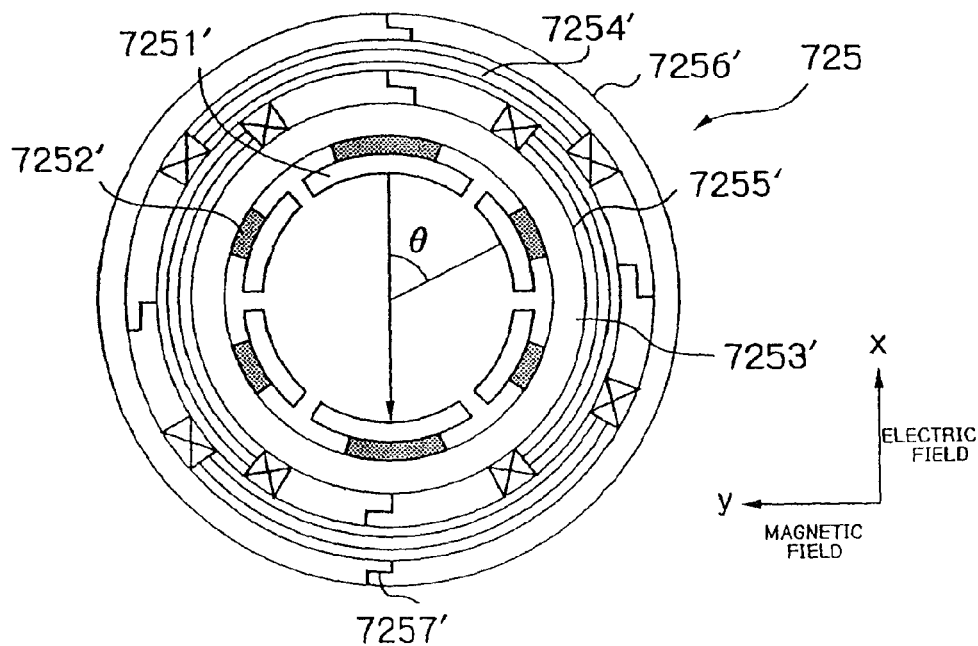

FIG. 10B illustrates another example of the ExB separator applicable to the electro-optical system 70 according to this invention, with a cross sectional view perpendicular to an optical axis. This ExB separator is different to the example shown in FIG. 10A in the point of view that it includes six electro-static deflection electrodes 7251. In FIG. 10B, components of the ExB separator corresponding to those of FIG. 10A are denoted by the same reference numerals with "'", and description thereof is omitted. The electro-static deflection electrodes 7251' are supplied with the voltages k*cos θi (k:constant value), where θi (i=0, 1, 2, 3, 4, 5) is an angle between a line from the electrode center to the optical axis and the electric field direction (X direction)

The ExB separator illustrated in FIG. 10B has coils 7254', 7255' for generating magnetic fields in the X and Y directions to control the perpendicular character, similar to that in FIG. 10A.

The ExB separator shown in FIG. 10B can provide a wider range where the electric field strength is constant, in comparison with that in FIG. 10A.

The coils for generating the magnetic fields are of a saddle-shaped type in the ExB separators illustrated in FIGS. 10A and 10B. However, a coil of a troidal type can also be employed. Further, the ExB separators shown in FIG. 10 can be applied to embodiments of the electron beam apparatuses explained below as well as the electron beam apparatus 70 shown in FIG. 8.

Returning to FIG. 8, the images of the secondary electron beams focussed at the point P3 are again focussed at respective corresponding apertures 743a of the multi-aperture detection plate 743 by through the enlarging lenses 741, 742, and detected the detectors 761 correspondingly located to the apertures 743a. The detectors 761 convert the detected beams to electric signals representing the strength of the beams. The electric signals are converted to digital signals at the A/D converters 762 and inputted to the image processing unit 763. As the detectors 761, PN junction diodes which directly detect strengths of electron beams, PMT (photo multiplier tubes) which detect strengths of electron beams after converting them to radiation light by a fluorescent plate.

The image processing unit 763 provides image data obtained from the input digital data. The image processing unit 763 receives a scanning signal which is used to deflect the primary electron beams, from the control unit 2 (FIG. 1). Therefore, the image processing unit receives a signal representing positions of irradiated points on the wafer, and hence can produce an image representing the wafer surface. By comparing the image obtained as above with a predetermined reference pattern, the quality of the pattern on the wafer to be evaluated is determined.

Further, by moving the pattern on the wafer to be evaluated to a position near the optical axis of the primary optical system by registration, obtaining a line width evaluation signal by line-scanning, and by calibrating it, a line width of a pattern on the wafer surface can be detected.

In a prior electron beam apparatus, secondary electrons which are generated when primary electron beams are irradiated on a wafer, are focussed to a point via two steps lenses common to the primary electrons, are deflected by an ExB separator 725 located at the focal point, and are imaged at multiple detectors without passing any lens. As to the common lenses of the primary and secondary optical systems, since it is required to adjust a lens conditions of the primary optical system prior to that of the secondary optical system, a focal condition and enlarging rate of the secondary optical system cannot be controlled. Therefore, the focal condition and enlarging rate thereof cannot be sufficiently adjusted when they are incorrect.

On the other hand, in the present invention, after the secondary electrons are deflected by the ExB separator 725, they are enlarged by the lens of the secondary optical system, a focal condition and enlarging rate can be adjustable apart from a lens condition setting of the primary optical system.

After the primary electron beams pass through the apertures of the multi-aperture plate 723 of the primary optical system, they are focussed on the wafer W, and thereby the secondary electrons are emitted from the wafer. The secondary electron beams are then imaged at the detectors 761. In this event, it is necessary to minimize three aberration effects which are distortion, axial chromatic aberration, and field astigmatism derived in the primary optical system.

In particular, in the case where optical paths of the primary and secondary electron beams are partially common, since primary electron streams and secondary electron streams flow through the common optical path, a beam current having 2 times flows, and thus peculiar in the focal condition of the primary electron beam caused by a space charge effect is two times. Also, it is difficult to adjust the axes of the primary and secondary electron beams in the common optical path. That is, when an adjustment of the axis of the primary electron beams, the axis of the secondary electron beams may be out of their condition, and when an adjustment of an axis of the secondary electron beams, the axis of the primary electron beams may be out of their condition. Further, in the common optical path, when the lens is adjusted to satisfy a focal condition of the primary electron beams, a focal condition of the secondary electron beams may be out of the condition, and the focal condition of the secondary electron beams is adjusted, the focal condition of the primary electron beams may be out of the condition.

Therefore, it is better to design the common path as short as possible. However, when an ExB separator 725 is installed at a position under an objective lens 726, this occurs a problem that an image plan distance of the objective lens is longer, and thereby aberrations are larger. In the present invention, the ExB separator 725 is installed at a side of the electron gun 721 with respect to the objective lens, resulting in that the primary and secondary optical systems commonly employ only a single lens.

In addition, as to relationships between spaces among the primary electron beams and the secondary optical system, when the primary electron beams are spaced to each other by a distance larger than the aberration of the secondary optical system to reduce cross-talk between the beams.

Further, it is preferable to set an deflection angle of the electro-static deflector 727 to be −½ of an electromagnetic deflection angle by the electromagnetic deflector of the ExB separator 725. Since the chromatic aberration of deflection may be small by setting above, a beam diameter of the beam may be made relatively small even the beam passes the ExB separator.

Pre-Charge Unit 81

The pre-charge unit 81, as illustrated in FIG. 1, is disposed adjacent to the column 71 of the electro-optical system 70 within the working chamber 31. Since this evaluation system 1 is configured to test a wafer for device patterns or the like formed on the surface thereof by irradiating the wafer with electron beams, the surface of the wafer may be charged up depending on conditions such as the wafer material, energy of the irradiated electrons, and so on. Further, even on the surface of a single wafer, some regions may be highly charged, while the other regions may be lowly charged. Variations in the amount of charge on the surface of the wafer would cause corresponding variations in information provided by the resulting secondary electrons, thereby failing to acquire correct information. For preventing such variations, in this embodiment, the pre-charge unit 81 is provided with a charged particle irradiating unit 811. Before testing electrons are irradiated to a predetermined region on a wafer, charged particles are irradiated from the charged particle irradiating unit 811 of the pre-charge unit 81 to eliminate variations in charge. The charges on the surface of the wafer previously form an image of the surface of the wafer, which image is evaluated to detect possible variations in charge to operate the pre-charge unit 81 based on the detection. Alternatively, the pre-charge unit 81 may irradiate a blurred primary electron beam.

In a method of detecting an electrical defect of a wafer, it is capable to utilize such a phenomenon that when there are electrically isolated and conductive portions on the wafer, voltages of the portions are different to each other. In order that, a wafer is pre-charged to cause a difference in potential between portions which are intended to be electrically isolated, provided that one of them is conductive in fact, and then electron beams are irradiated on the wafer to detect the voltage difference therebetween. By analyzing the detected data, the conductive portion which is intended to be isolated can be detected.

In such a method of detecting an electrical defect, the pre-charge unit 81 can be employed to pre-charge a wafer.

Potential Applying Unit 83

Figure 11:
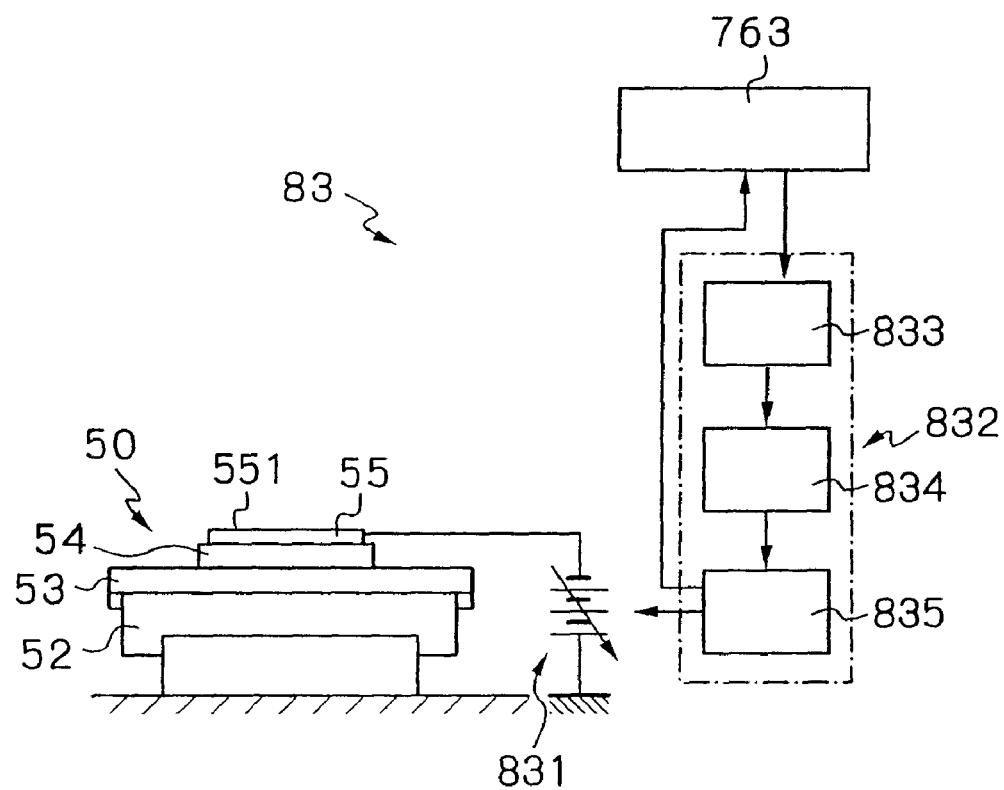
FIG. 11 illustrates a potential application system applicable to the electron beam apparatus concerning the present invention.

FIG. 11 shows a constitution of the potential applying mechanism 83. The mechanism 83 applies a potential of ± several volts to a carrier of a stage, on which the wafer is placed, to control the generation of secondary electrons based on the fact that the information on the secondary electrons emitted from the wafer (secondary electron yield) depend on the potential on the wafer. The potential applying mechanism 83 also serves to decelerate the energy originally possessed by irradiated electrons to provide the wafer with irradiated electron energy of approximately 100 to 500 eV.

As illustrated in FIG. 11, the potential applying mechanism 83 comprises a voltage applying device 831 electrically connected to the carrying surface 551 of the stage apparatus 50; and a charge-up examining/voltage determining system (hereinafter examining/determining system) 832. The examining/determining system 832 comprises a monitor 833 electrically connected to an image processing unit 763 of the detecting system 76 in the electro-optical system 70; an operator 834 connected to the monitor 833; and a CPU 835 connected to the operator 834. The CPU 835 is incorporated in the control unit 2 (FIG. 1), and supplies a voltage control signal to the voltage applying device 831. The CPU 835 further provides some components of the electron system with control signals. For instance, it applies a scanning signal to the deflector 727 (FIG. 8) of the electro-optical system 70. In the potential applying mechanism 83, the monitor 833 displays an image reproduced by the image processing unit 763. By studying the image, an operator can search, using an operation input unit 834 and CPU 835, a potential at which the wafer is hardly charged, and control the potential applying device 831 to provide the potential to the holder 55 of the stage apparatus 50.

Electron Beam Calibration Mechanism 85

Figure 12A:
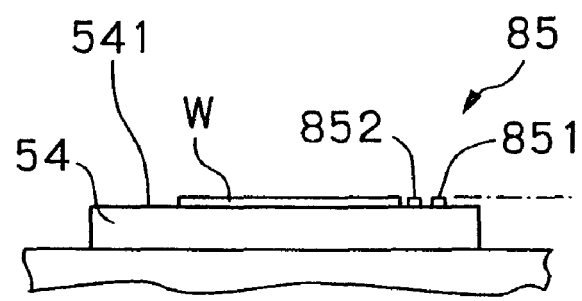
FIG. 12A is a side view thereof and FIG. 12B is a plan view thereof.
Figure 12B:
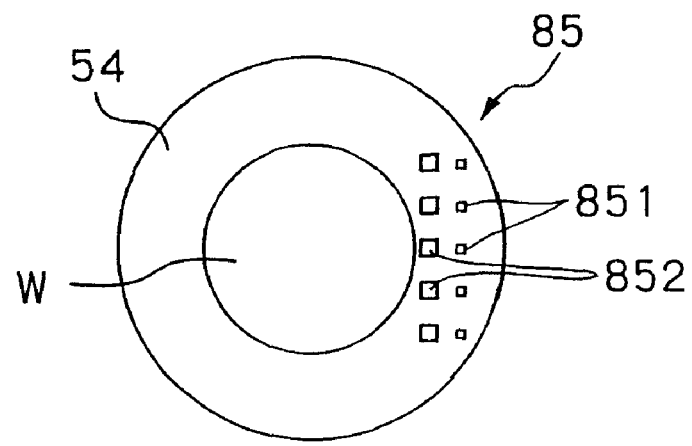

As illustrated in FIGS. 12A and 12B, the electron beam calibration mechanism 85 comprises a plurality of Faraday cups 851, 852 for measuring a beam current, disposed at a plurality of positions in a lateral region of the wafer carrying surface 541 on the turntable 54. The Faraday cups 851 are provided for a narrow beam (approximately φ=2 μm), while the Faraday cups 852 for a wide beam (approximately φ=30 μm). The Faraday cuts 851 for a narrow beam measure a beam profile by driving the turntable 54 step by step, while the Faraday cups 852 for a wide beam measure a total amount of currents. The Faraday cups 851, 852 are mounted on the wafer carrying surface 541 such that their top surfaces are coplanar with the upper surface of the wafer W carried on the carrying surface 541. In this way, the primary electron beam emitted from the electron gun is monitored at all times, and a voltage to the electron gun is controlled so that the strength of the electron beams applied at the wafer W is substantially constant. That is, since electron guns cannot emit a constant electron beams at all times but varies in the emission current as it is used over time, the electron beam strength is calibrated by the calibration mechanism.

Alignment Controller 87

The alignment controller 87 aligns the wafer W with the electro-optical system 70 using the stage apparatus 50. The alignment controller 87 performs the control for rough alignment through wide field observation using the optical microscope 871 (a measurement with a lower magnification than a measurement made by the electro-optical system); high magnification alignment using the electro-optical system of the electro-optical system 70; focus adjustment; testing region setting; pattern alignment; and so on. The wafer is tested at a low magnification in this way because an alignment mark must be readily detected by an electron beam when the wafer is aligned by observing patterns on the wafer in a narrow field using the electron beam for automatically testing the wafer for patterns thereon.

The optical microscope 871 is disposed on the housing 30. Alternatively, it may be movably disposed within the housing 30. A light source (not shown) for operating the optical microscope 871 is additionally disposed within the housing 30. The electro-optical system for observing the wafer at a high magnification, shares the electro-optical systems (primary optical system 72 and secondary optical system 74) of the electro-optical system 70.

Figure 13:
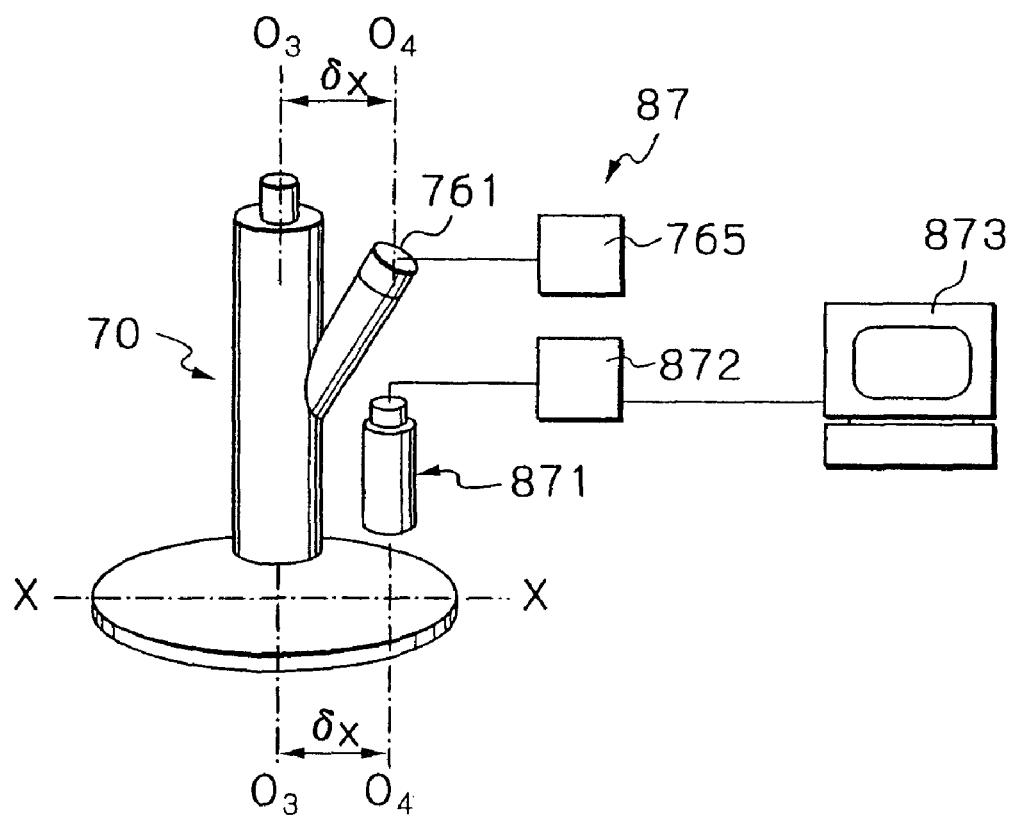
FIG. 13 schematically illustrates a device for controlling an alignment of wafers, which is applicable to the electron beam apparatus concerning the present invention.

The configuration of the alignment controller 87 may be generally illustrated in FIG. 13. For observing a point of interest on a wafer at a low magnification, the X-stage or Y-stage of the stage apparatus 50 is controlled to move the point of interest on the wafer into a field of the optical microscope 871. The wafer is studied in a wide field by the optical microscope 871, and the point of interest on the wafer to be observed is displayed on a monitor 873 through a CCD 872 to roughly determine a position to be observed. In this event, the magnification of the optical microscope may be changed from a low magnification to a high magnification.

Next, the stage apparatus 50 is moved by a distance corresponding to a spacing δx between the optical axis of the electro-optical system 70 and the optical axis of the optical microscope 871 to move the point on the wafer under observation, previously determined by the optical microscope 871, to a point in the field of the electro-optical system 70. In this event, since the distance δx between the axis $O_3$-$O_3$ of the electro-optical system and the axis $O_4$-$O_4$ of the optical microscope 871 is previously known (while it is assumed that the electro-optical system 70 is deviated from the optical microscope 871 in the direction along the X-axis in this embodiment, they may be deviated in the Y direction as well as in the X direction), the point under observation can be moved to the viewing position by moving the stage apparatus 50 by the distance δx. After the point under observation has been moved to the viewing position of the electro-optical system 70, the point under observation is imaged by the electro-optical system at a high magnification for storing a resulting image or displaying the image on the monitor 765.

After the point under observation on the wafer imaged by the electro-optical system at a high magnification is displayed on the monitor, misalignment of the stage apparatus 50 with respect to the center of rotation of the turntable 54 in the wafer rotating direction, or misalignment 80 of the wafer in the wafer rotating direction with respect to the optical axis $O_3$-$O_3$ of the electro-optical system 70 are detected in a conventional method. Then, the operation of the stage apparatus 50 is controlled to align the wafer, based on the detected values and data on a testing mark attached on the wafer, or data on the shape of the patterns on the wafer which have been acquired in separation.

Controller 2

The controller mainly comprises a main controller, a control controller and a stage controller.

The main controller has a man-machine interface through which the operation by an operator (input of various instructions/commands and menus, instruction to start a test, switch between automatic and manual test modes, input of all commands necessary when the manual test mode) is performed. Further, the main controller performs a communication to a host computer in a factory, control of a vacuum pumping system, carriage of a sample such as a wafer, control of alignment, transmission of commands to the control controller and the stage controller and receipt of information. Moreover, the main controller has a function of obtaining an image signal from the optical microscope, a stage vibration correcting function for feeding back a vibration signal of the stage to the electro-optical system to correct a deteriorated image, and an automatic focus correcting function for detecting a Z-direction (the direction of the axis of the primary optical system) displacement of a sample observing position to feed back the displacement to the electro-optical system so as to automatically correct the focus. Reception and transmission of a feedback signal to the electro-optical system and a signal from the stage can be performed through the control controller and the stage controller.

The control controller is mainly responsible for control of the electro-optical system, or control of highly accurate voltage sources for electron gun, lenses, aligner and Wien filter). Specifically, the control controller effects control (gang control) of automatic voltage setting to each lens system and the aligner in correspondence with each operation mode, for example, causes a region to be irradiated by a constant electron current even if the magnification is changed, and automatically sets a voltage applied to each lens system and the aligner in correspondence with each magnification.

The stage controller is mainly responsible for control regarding the movement of the stage and enables the achievement of accurate X and Y direction movements of micrometer order (tolerance:±0.5 micrometer). Further, the stage controller achieves control of rotation (θ control) of the stage within an error accuracy of ±0.3 seconds.

The evaluating system according to the invention as described above, can functionally combine the electron beam apparatus of a multi-beam type with the respective components of the evaluation system, resulting in that samples can be evaluated with a high throughput. If a sensor for detecting a clean level of the environment housing, it is possible to test samples while monitoring refuses in the housing. Further, since the pre-charge unit is provided, a wafer made of an insulation material may not be affected from charging.

Some embodiments of a combination of a stage apparatus 50 and a charged particle beam irradiation portion of a electro-optical system 70 in the electron beam apparatus accommodated in the evaluation system 1 according to the present invention.

When testing a sample such as a semiconductor wafer possessed with ultra accurate processing, a stage apparatus 50 which is capable of accurately positioning the wafer in a vacuum working chamber 31, is required. As such a stage apparatus usable in such a case that ultra accurately positioning is required, a mechanism for supporting X-Y stage with a hydrostatic bearings with a non-contact manner, is employed. In this event, a degree of vacuum is maintained in the vacuum chamber or working chamber 31 by forming a differential pumping mechanism for pumping a high pressure gas in a range of the hydrostatic bearing so that the high pressure gas supplied from the hydrostatic bearings will not be pumped directly to the working chamber 31. In the description, the term "vacuum" means a vacuum condition so-called in this field.

Figure 14A:
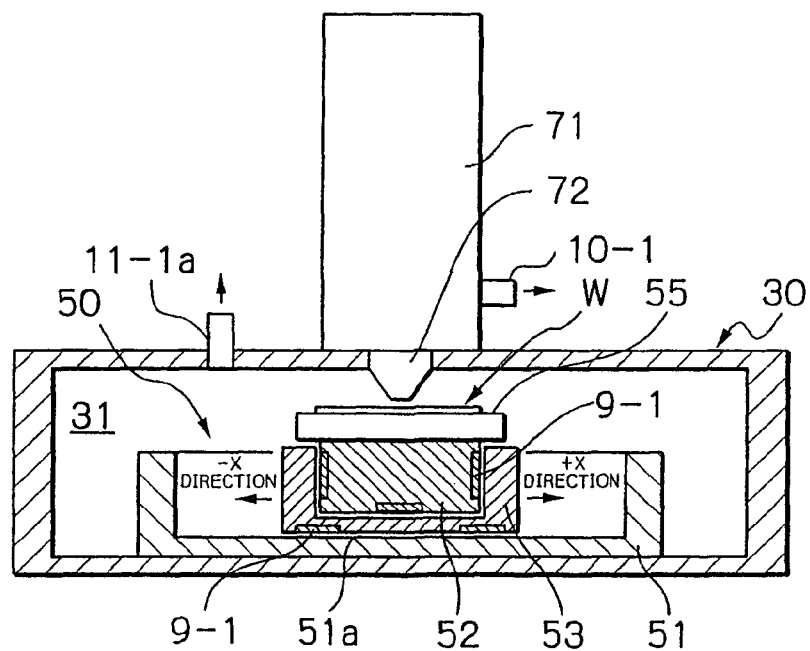
FIG. 14 illustrates a relationship between an X-Y stage and a charged particle beam irradiation means of an electron optical system in a conventional electron beam apparatus.
Figure 14B:
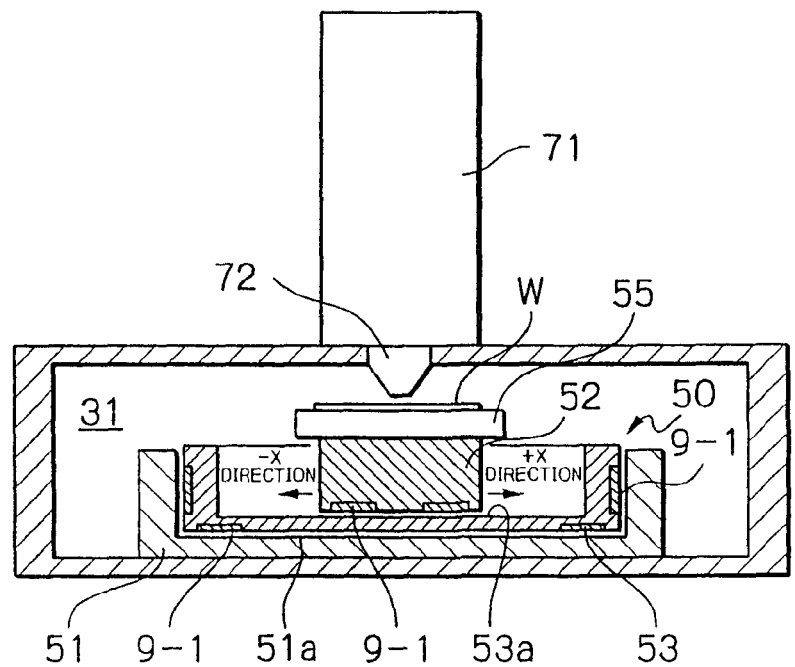

An example of the combination of a stage apparatus and electro-optical system 70 according to the prior art is illustrated in FIG. 14. FIGS. 14A and 14B are elevation and side views, respectively. In the prior art, a bottom of a column 71 of an electron beam apparatus for generating an electron beam to irradiate a wafer, i.e., an electron beam emitting tip 72 is attached to a main housing 30 which constitutes a vacuum chamber 31. The inside of the column 71 is evacuated to vacuum by a vacuum pipe 10-1, and the chamber 31 is evacuated to a vacuum by a vacuum pipe 11-1$a$. Then, electron beam is emitted from the bottom 72 of the column 71 to a sample such as a wafer W placed therebelow.

The wafer W is removably held on a holder 55 in a known method. The holder 55 is mounted on the top surface of a Y-table 52 of an X-Y stage. The Y-table 52 has a plurality of hydrostatic bearings 9-1 attached on surfaces (both left and right side surfaces and a lower surface in FIG. 14A) opposite to a guide surface of an X-table 53. The Y-table 52 is movable in the Y direction (in the left-to-right direction in FIG. 12B), while maintaining a small gap between the guide surface and the opposite surfaces by the action of the hydrostatic bearings 9-1. Further, around the hydrostatic bearings 9-1, a differential pumping mechanism is disposed to prevent a high pressure gas supplied to the hydrostatic bearings 9-1 from leaking into the inside of the vacuum chamber 31. This situation is shown in FIG. 15.

Figure 15:
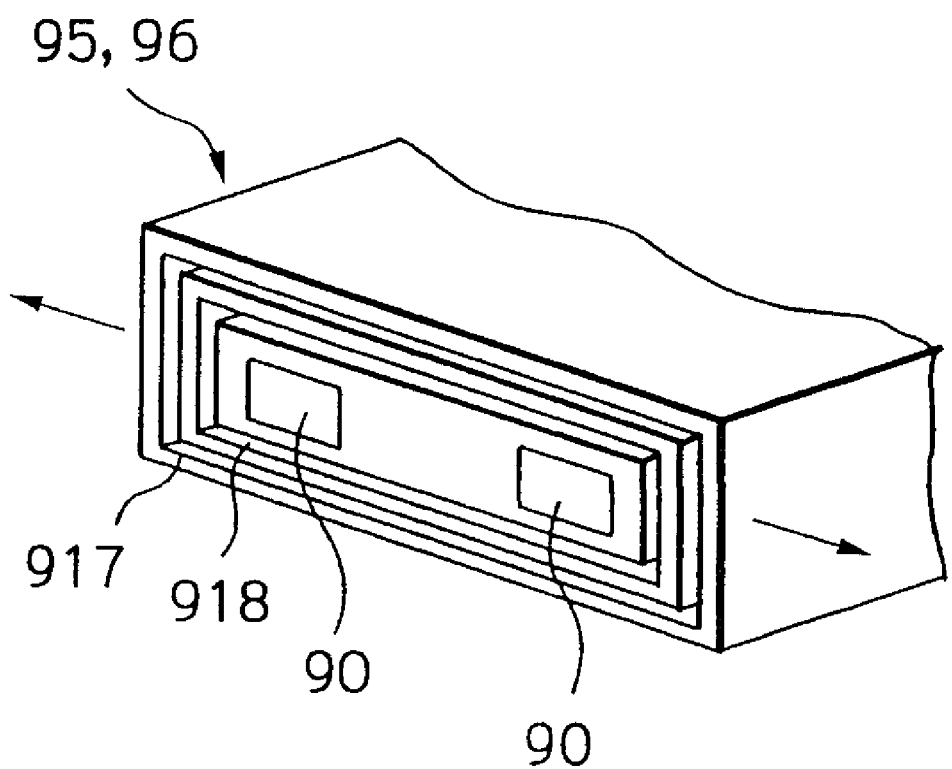
FIG. 15 illustrates the state of the bottom of the X-Y stage indicated in FIG. 14.

As illustrated in FIG. 15, double grooves 18-1 and 17-1 are formed around the hydrostatic bearings 9-1, and these grooves are evacuated to vacuum at all times by a vacuum pipe and a vacuum pump, not shown. With such a structure, the Y-table 52 is supported in a non-contact state in vacuum so that it is freely movable in the Y direction. These double grooves 18-1 and 17-1 are formed to surround the hydrostatic bearings 9-1 of the Y-table 52, on the surface on which the hydrostatic bearings are disposed. Since the hydrostatic bearing may have a known structure, detailed description thereon is omitted.

The X-table 53, which carries the Y-table 52 has a concave shape open directed upwardly, as is apparent from FIG. 14. The X-table 53 is also provided with completely similar hydrostatic bearings and grooves, such that the X-table 53 is supported to a stage stand or fixed table 51 in a non-contact manner, and is freely movable in the X direction.

By combining movements of these Y-table 52 and X-table 53, it is possible to move the wafer W to an arbitrary position in the horizontal direction with respect to the bottom of the column, i.e., the electron beam emitting tip 72 to emit electron beams to a desired position of the wafer W.

In the combination of the stage apparatus 50 and the electron beam emitting tip 72 can be employed in the evaluation system according to the present invention. However, there are problems below.

In the prior combination of the hydrostatic bearings 9-1 and the differential pumping mechanism, the guide surfaces 53a, 51a opposing to the hydrostatic bearings 9-1 reciprocate between a high pressure gas atmosphere around the hydrostatic bearings and a vacuum environment within the working chamber 31 as the X-Y stage is moved. In this event, while the guide surfaces are exposed to the high pressure gas atmosphere, the gas is adsorbed to the guide surfaces, and the adsorbed gas is released as the guide surfaces are exposed to the vacuum environment. Such states are repeated. Therefore, as the X-Y stage is moved, the degree of vacuum within the working chamber 31 is degraded, rising a problem that the aforementioned processing such as exposure, testing and working, by use of the electron beam cannot be stably performed and that the wafer is contaminated.

Figure 16A:
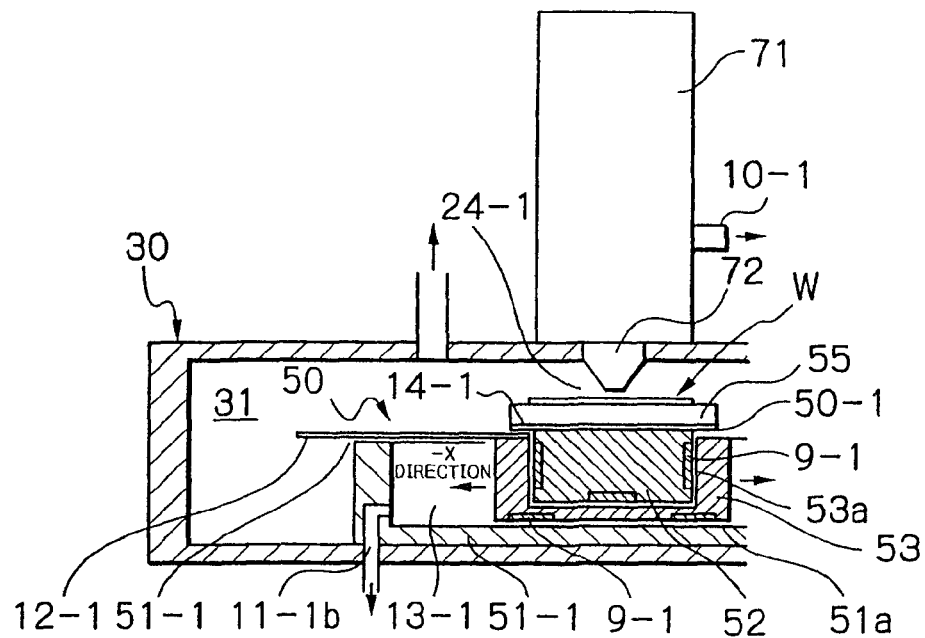
FIG. 16 illustrates a relationship between an X-Y stage and a charged particle beam irradiation means of an electron optical system according to an embodiment of an electron beam apparatus of the present invention.
Figure 16B:
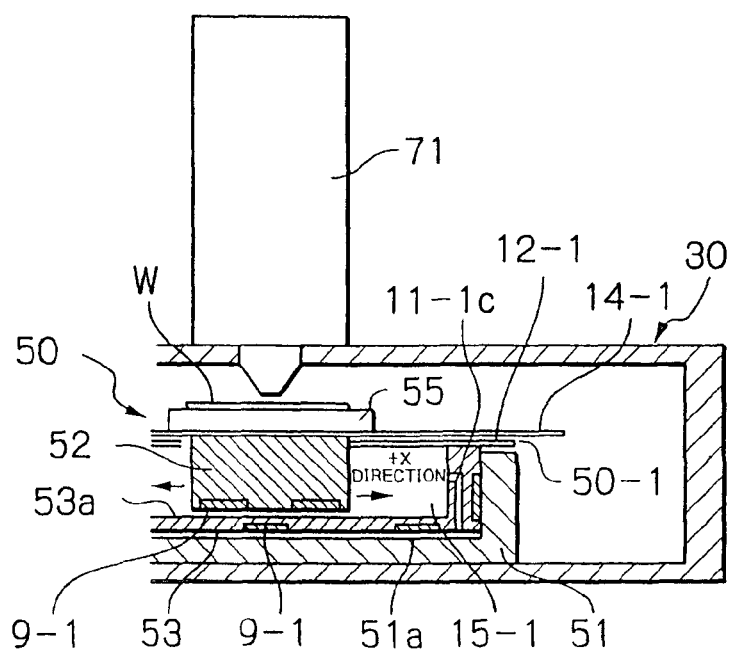

Therefore, an apparatus is required which prevents the degree of vacuum from degrading to permit stable processing such as testing and working by use of an electron beam. FIG. 16 shows an embodiment of the combination of the stage apparatus 50 and the electron beam emitting tip 72 of an electro-optical system 70, which can derive advantages above. In FIG. 16, FIGS. 16A and 16B are front and side views, respectively.

As illustrated in FIG. 16, a partition plate 14-1 largely extending substantially horizontally in the Y directions (in the left and right directions in FIG. 16B) is attached on the top surface of a Y-table 52, such that a reducer 50-1 having a small conductance is formed at all times between the top surface of the X-table 53 and the partition plate 14-1. Also, on the top surface of an X-table 53, a partition plate 12-1 is placed to extend in the ±X directions (in the left and right directions in FIG. 14A), such that a reducer 51-1 is formed at all time between the top surface of a fixed table 51 and the partition plate 12-1. The fixed table 51 is mounted on a bottom wall in a main housing 30 in a conventional manner.

Thus, since the reducers 50-1 and 51-1 are formed at all times when the wafer table or holder 55 is moved to whichever position, so that even if a gas is released from the guide surfaces 53a and 51a while the Y-table 52 and X-table 53 are moved, the movement of the released gas is prevented by the reducers 50-1 and 51-1. Therefore, it is possible to significantly suppress an increase in pressure in a space 24-1 near the wafer irradiated with electron beams.

The side and lower surfaces of the movable section or Y-table 52 and the lower surface of the X-table 53 of the stage apparatus 50 are formed with grooves, around the hydrostatic bearings 9-1, for differential pumping, as illustrated in FIG. 15. Since evacuation to vacuum is performed through these grooves, the released gas from the guide surfaces are mainly pumped by these differential pumping mechanism when the reducers 1550, 1551 are formed. Therefore, the pressures in the spaces 13-1 and 15-1 within the stage apparatus 50 are higher than the pressure within the working chamber 30. Therefore, if locations which are evacuated to vacuum are separately provided, not only the spaces 13-1 and 15-1 are evacuated through the differential pumping grooves 17-1 and 18-1, but also the pressures in the spaces 13-1 and 15-1 can be reduced to further suppress an increase in pressure near the wafer W. Vacuum evacuation passages 11-1b and 11-1c are provided for this purpose. The evacuation passage 11-1b extends through the fixed table 51 and the main housing 30 and communicates with the outside of the housing 30. The evacuation passage 11-1c is formed in the X-table 53 and opened to the lower surface of the X-table.

While the provision of the partition plates 12-1 and 14-1 results in a requirement of increasing the size of the working chamber 30 such that the chamber 30 does not interfere with the partition walls, this aspect can be improved by making the partition plates of a retractile material or in a telescopical structure. In such an improved embodiment, the partition wall is made of rubber or in bellows form, and its end in the moving direction is fixed to the X-table 53 for the partition plate 14-1, and to an inner wall of the housing 8 for the partition plate 12-1, respectively.

Figure 17:
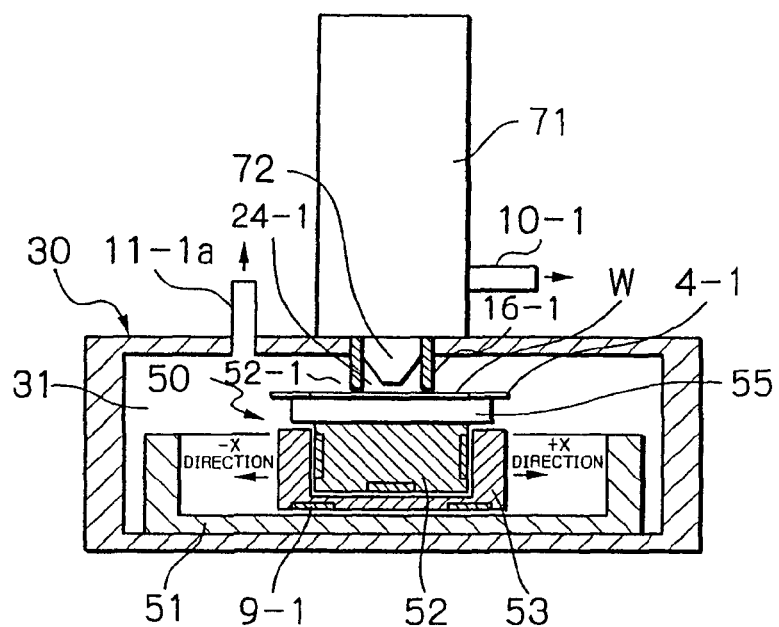
FIG. 17 illustrates a relationship between an X-Y stage and a charged particle beam irradiation means of an electron optical system according to another embodiment of an electron beam apparatus of the present invention.

FIG. 17 illustrates another embodiment of the combination of the stage apparatus 50 and the electron emitting tip 72 of the electro-optical system 70. In the example, a cylindrical partition 16-1 is formed around the bottom of the column 71, i.e., the electron beam emitting tip 72 to provide a reducer between the top surface of the wafer W and the electron beam emitting tip 72. In such a configuration, even if a gas is released from the X-Y stage to cause an increased pressure within the working chamber 31, a pressure difference is produced between the inside of the chamber C and the inside 1524 of the partition, because the inside 24-1 of the partition is partitioned by the partition 16-1 and the gas is pumped through the vacuum pipe 10-1. Therefore, an increased pressure within the space 24-1 in the partition may be suppressed. While a gap between the partition 16-1 and the surface of the wafer W should be settled depending on the pressure maintained within the working chamber 31 and around the emitting tip 72, approximately several tens of μm to several mm are proper. The inside of the partition 16-1 is communicated with the vacuum pipe 10-1 by a conventional method.

Also, since electron beam apparatus may apply a wafer W with a high voltage of approximately several kV, a conductive material placed near the wafer gives rise to a discharge. In this case, the partition 16-1 may be made of an insulating material such as ceramics to prevent a discharge between the wafer W and the partition 16-1.

A ring member 4-1 disposed around the wafer W is a plate-shaped adjusting part fixed to the wafer base or holder 55, which is set at the same level as the wafer such that a small gap 25-1 is formed over the entire periphery of the bottom of the partition 16-1. Therefore, even when electron beams are irradiated to whichever position of the wafer W, the constant small gap 52-1 is formed at all times at the bottom of the partition 16-1, thereby making it possible to stably maintain the pressure in the space 24-1 around the bottom of the column 71.

Figure 18:
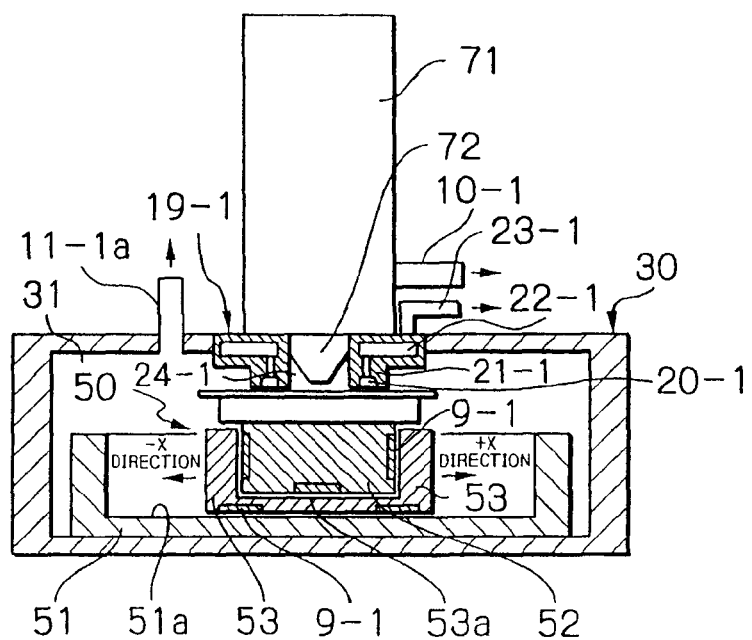
FIG. 18 illustrates a relationship between an X-Y stage and a charged particle beam irradiation means of an electron optical system according to still another embodiment of an electron beam apparatus of the present invention.

FIG. 18 illustrates a still another embodiment of the combination of the stage apparatus 50 and the electron beam emitting tip 72 of the electron beam apparatus. A partition 19-1 containing a differential pumping structure is disposed around an electron beam emitting tip 72 of the column 71. The partition 19-1 has a cylindrical shape, and a circumferential groove 20-1 is formed inside. An pumping passage 21-1 extends upward from the circumferential grove. The pumping passage is connected to a vacuum pipe 23-1 through an internal space 22-1. There is a small gap ranging from several tens of μm to several mm between the lower end of the partition wall 19-1 and the upper surface of the wafer W.

In the configuration shown in FIG. 18, even if a gas is released from the stage apparatus 50 in association with a movement of the X-Y stage to cause an increased pressure within a working chamber 30, and the gas is going to flow into the electron beam emitting tip 72, the partition 19-1 reduces the gap between the wafer W and the tip to make the conductance extremely small. Therefore, the gas is impeded from flowing into the electron beam emitting tip 72 and the amount of flowing gas is reduced. Further, the introduced gas is pumped from the circumferential groove 20-1 to the vacuum pipe 1523, so that substantially no gas flows into the space 24-1 around the electron beam emitting tip 72, thereby making it possible to maintain the pressure around the electron beam emitting tip 72 at a desired high vacuum.

Figure 19:
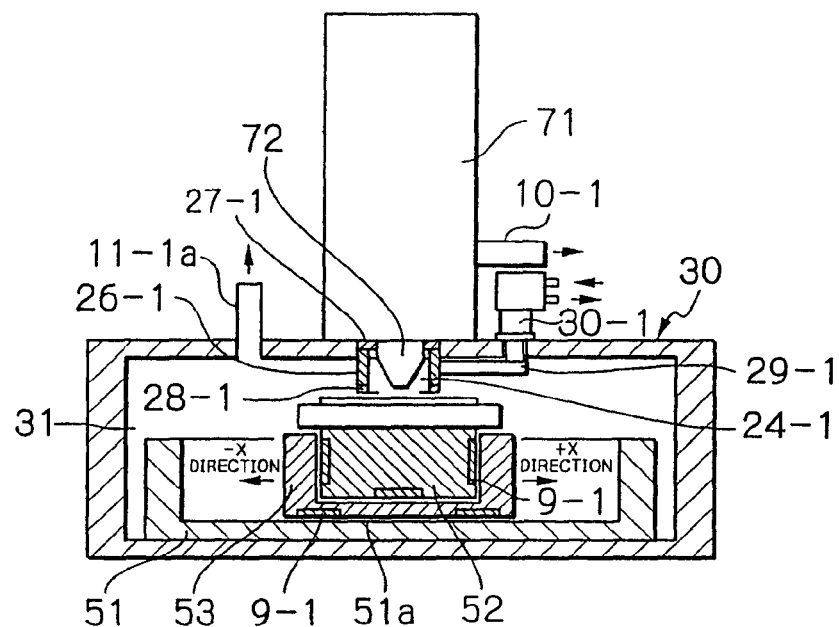
FIG. 19 illustrates a relationship between an X-Y stage and a charged particle beam irradiation means of an electron optical system according to further another embodiment of an electron beam apparatus of the present invention.

FIG. 19 illustrates another embodiment of the combination of the stage apparatus 50 and the electron beam emitting tip 72 of the electro-optical system 70. In this embodiment, a partition 26-1 is formed around the electron beam emitting tip 72 in the working chamber 31 to separate the electron beam emitting tip 72 from the chamber 31. This partition 26-1 is coupled to a freezer 30-1 through a supporting member 29-1 made of a high thermally conductive material such as copper or aluminum, and is cooled at −100° C. to −200° C. A member 27-1 is provided for preventing thermal conduction between the cooled partition 26-1 and the column 71, and is made of a low thermally conductive material such as ceramics resin material. Also, a member 28-1, which is made of a non-insulating material such as ceramics, is formed at a lower end of the partition 26-1 for preventing the wafer W and the partition 26-1 from discharging therebetween.

In the configuration shown in FIG. 19, gas molecules which are going to flow from the working chamber 31 into the electron beam emitting tip 72 are impeded by the partition 26-1 from flowing toward the electron beam emitting tip, and even if the molecules flow, they are frozen and trapped on the surface of the partition 26-1, thereby making it possible to maintain low the pressure in the space around the electron beam emitting tip 72.

As the freezer, a variety of freezers can be used such as a liquid nitrogen based freezer, an He freezer, a pulse tube type freezer, and so on.

Figure 20:
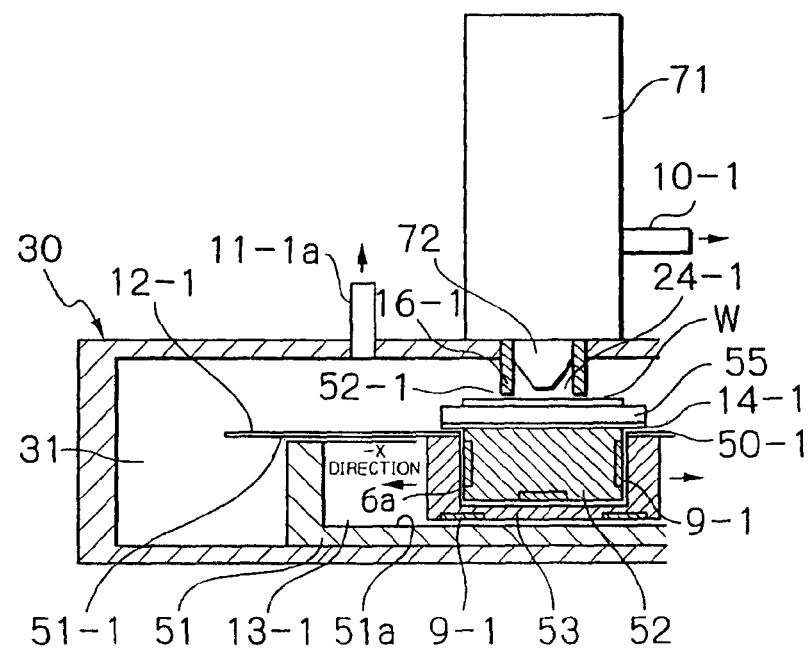
FIG. 20 illustrates a relationship between an X-Y stage and a charged particle beam irradiation means of an electron optical system according to still another embodiment of an electron beam apparatus of the present invention.

FIG. 20 illustrates a further embodiment of the combination of the stage apparatus 50 and the electron beam emitting tip 72 of the electro-optical system 70. Similar to the constitution shown in FIG. 16, a partition plates 12-1, 14-1 are disposed on both movable sections of the X-Y stage or Y and X-tables 52, 53. Therefore, even if the sample base or holder 55 is moved to an arbitrary position, the space 13-1 within the stage apparatus and the inside of the working chamber 31 are partitioned by these partitions through reducers 50-1, 51-1. Further, a partition 16-1 similar to that illustrated in FIG. 17 is formed around the electron beam emitting tip 72 to partition the inside of the working chamber 31 and the space 24-1, in which the electron beam emitting tip 72 is positioned, through a reducer 52-1. Therefore, even if a gas adsorbed on the stage is released into the space 13-1 while the stage is moved, to increase the pressure in this space, an increased pressure in the working chamber 31 is suppressed, and an increased pressure in the space 24-1 is further suppressed. In this way, the pressure in the space 24-1 around the electron beam irradiation tip 71 can be maintained in a low state. In addition, the space 24-1 can be stably maintained at a yet lower pressure, by utilizing the partition 19-1 which contains a differential pumping mechanism, or the partition 26-1 cooled by a freezer which is illustrated in FIG. 40, as the partition 16-1.

In this embodiment with regard to the electron beam emitting tip, the stage apparatus can be accurately positioned in the vacuumed working chamber, and the pressure around the irradiation tip is prevented from increasing, resulting in obtaining a high quality image data.

Figure 21:
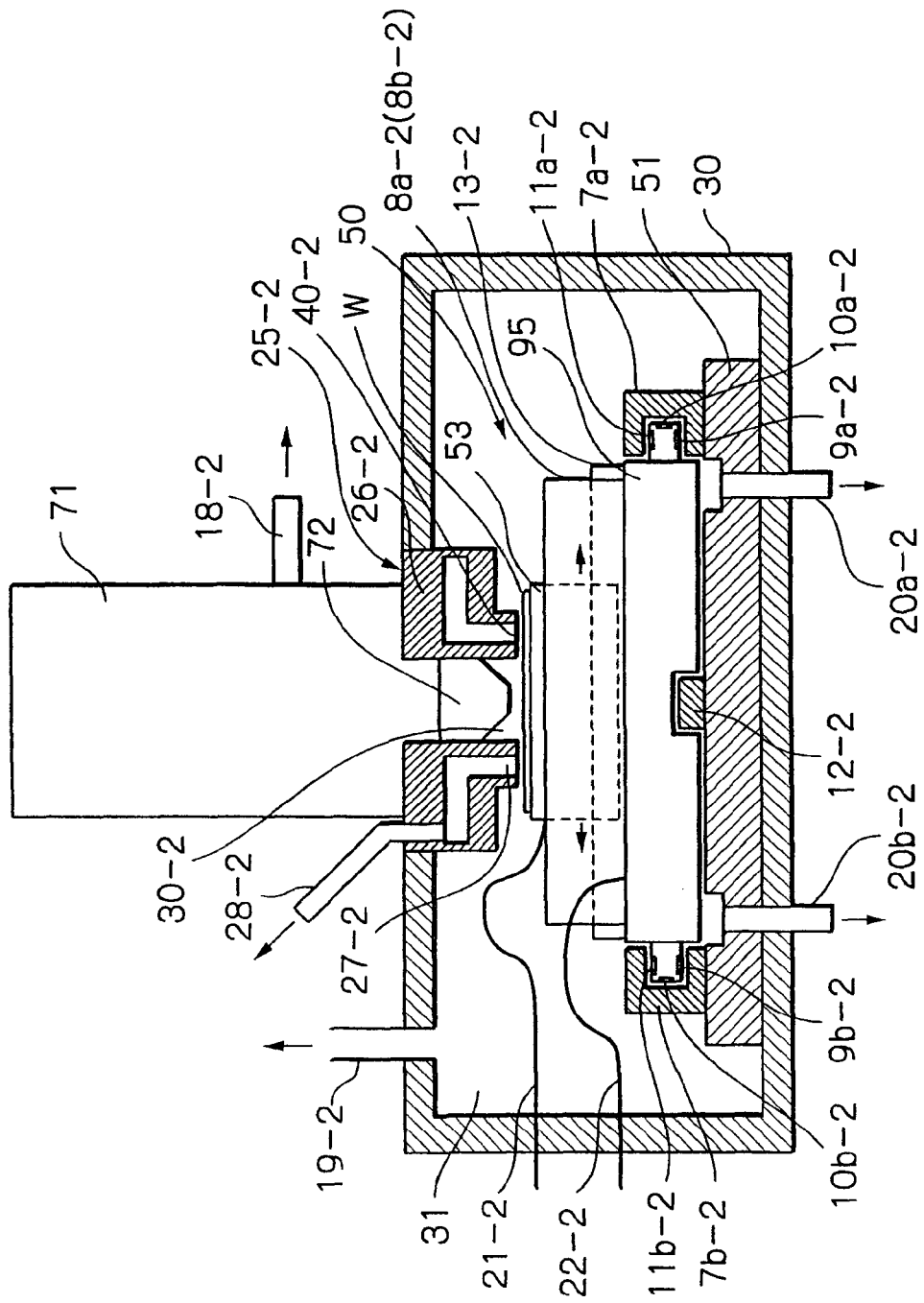
FIG. 21 illustrates a relationship between an X-Y stage and a charged particle beam irradiation means of an electron optical system according to still another embodiment of an electron beam apparatus of the present invention.

FIG. 21 shows a more further embodiment of the combination of the stage apparatus 50 and the electron beam emitting tip 72 of the electro-optical system 70. In this embodiment, a bottom of the column 71, i.e., the electron beam emitting tip 72 is attached to a main housing 30 which defines a working chamber 31. A base or fixed table of the X-Y stage of the stage apparatus 50 is fixed on a bottom wall of the main housing 30, and a Y-table 52 is mounted on the fixed table 51. On both sides of the Y-table 52 (on left and right sides in FIG. 21), protrusions are formed, which are protruding into recessed grooves of a pair of Y direction guides 7a-2 and 7b-2 carried on the fixed table 51 formed in the sides facing the Y-table. The recessed grooves extend in the Y direction (the direction perpendicular to the drawing surface) substantially over the entire length of the Y direction guides. Hydrostatic bearings 11a-2, 9a-2, 11b-2, 9b-2 in a known structure are disposed on the top surface, bottom surface and side surfaces of the protrusions protruding into the recessed grooves, respectively. A high pressure gas is blown off through these hydrostatic bearings to support the Y-table 52 with respect to the Y direction guides 7a-2, 7b-2 in a non-contact manner and to allow the same to smoothly reciprocate in the Y direction. Also, a linear motor 12-2 in a known structure is disposed between the pedestal table 51 and the Y-table 52 to drive the Y-table in the Y direction. The Y-table 52 is supplied with a high pressure gas through a flexible pipe 22-2 for high pressure gas supply, so that the high pressure gas is supplied to the hydrostatic bearings 9a-2 to 11a-2 and 9b-2 to 11b-2 through a gas passage (not shown) formed in the Y-table. The high pressure gas supplied to the hydrostatic bearings blows out into a gap of several microns to several tens of microns formed between opposing guiding surfaces of the Y direction guide to serve to precisely position the Y-table 52 with respect to the guide surfaces in the X direction and Z-direction (upward and downward directions in FIG. 21).

An X-table 53 is carried on the Y-table 52 for movement in the X direction (in the left-to-right direction in FIG. 21). On the Y-table 52, a pair of X direction guides 8a-2, 8b-2 (only 8a-2 is shown) identical in structure to the Y direction guides 7a-2, 7b-2 for the Y-table are disposed with the X-table 53 interposed therebetween. A recessed groove is also formed in the side of the X direction guide facing the X-table 53, and a protrusion is formed in a side portion of the X-table (a side portion facing the X direction guide), protruding into the recessed groove. The recessed groove extends substantially over the entire length of the X direction guide. Hydrostatic bearings (not shown) similar to the hydrostatic bearings 11a-2, 9a-2, 10a-2, 11b-2, 9b-2, 10b-2 are disposed on the top surface, bottom surface and side surfaces of the protrusion of the X-table 53 protruding into the recessed groove in similar positioning. Between the Y-table 52 and the X-table 53, a linear motor 13-2 in a known structure is disposed so that the X-table is driven in the X direction by means of the linear motor. Then, the X-table 53 is supplied with a high pressure gas through a flexible pipe 21-2 to supply the high pressure gas to the hydrostatic bearings. The high pressure gas is blown out from the hydrostatic bearings to the guide surfaces of the X direction guide to highly accurately support the X-table 53 with respect to the Y direction guide in a non-contact manner. The vacuum working chamber 31 is evacuated by vacuum pipes 19-2, 20a-2, 20b-2 connected to a vacuum pump or the like in a conventional structure. The inlet sides (within the working chamber) of the pipes 20a-2, 20b-2 extend through the pedestal or fixed table 51 and are open near a position at which the high pressure gas is pumped from the X-Y stage on the top surface of the table 51, to maximally prevent the pressure within the working chamber 31 from rising due to the high pressure gas blown out from the hydrostatic bearings.

A differential pumping mechanism 25-2 is disposed around the electron beam emitting tip 72, so that the pressure in the electron beam irradiation space 30-2 is held sufficiently low even if the pressure in the working chamber 31 is high. Specifically, an annular member 26-2 of the differential pumping mechanism 25-2 attached around the electron beam emitting tip 72 is positioned with respect to the main housing 30 such that a small gap (from several micron to several hundred microns) 40-2 is formed between the lower surface (the surface opposing the wafer W) and the wafer, and an annular groove 27-2 is formed on the lower surface thereof. The annular groove 27-2 is connected to a vacuum pump or the like, not shown, through an pumping pipe 28-2. Therefore, the small gap 40-2 is evacuated through the annular groove 27-2 and an evacuate port 28-2, so that even if gas molecules attempt to invade from the working chamber 31 into the electron beam irradiating space 30-2 surrounded by the annular member 1626, they are pumped. In this way, the pressure within the electron beam irradiation space 30-2 can be held low to irradiate an electron beam without problem.

The annular groove 27-2 may be in a double structure or in a triple structure depending on the pressure within the chamber or the pressure within the electron beam irradiation space 30-2.

For the high pressure gas supplied to the hydrostatic bearings, dry nitrogen is generally used. However, if possible, a highly pure inert gas is further preferable. This is because if impurities such as moisture and oil components are included in the gas, these impurity molecules will attach on the inner surface of the housing which defines the vacuum chamber, and on the surfaces of components of the stage to deteriorate the degree of vacuum, and will attach on the surface of the sample to deteriorate the degree of vacuum in the electron beam irradiation space.

In the foregoing description, the sample or wafer W is not generally carried directly on the X-table 53, but carried on a wafer base or holder which has functions of removably holding the wafer, and making a slight positional change with respect to the X-Y stage, and so on. However, since the presence or absence of the sample base, and its structure are not related to the gist of the present invention, they are omitted for simplifying the description.

Since the electron beam apparatus described above can use a hydrostatic bearing stage mechanism used in the atmosphere as it is, a highly accurate X-Y stage equivalent to a highly accurate stage for atmosphere used in an exposure apparatus and so on can be implemented in an X-Y stage for an electron beam apparatus substantially at the same cost and in the same size.

The structure and positioning of the static pressure guides and actuators (linear motors) described above are merely embodiments in all sense, and any of static pressure guides and actuators can be applied if it is usable in the atmosphere.

Figure 22:
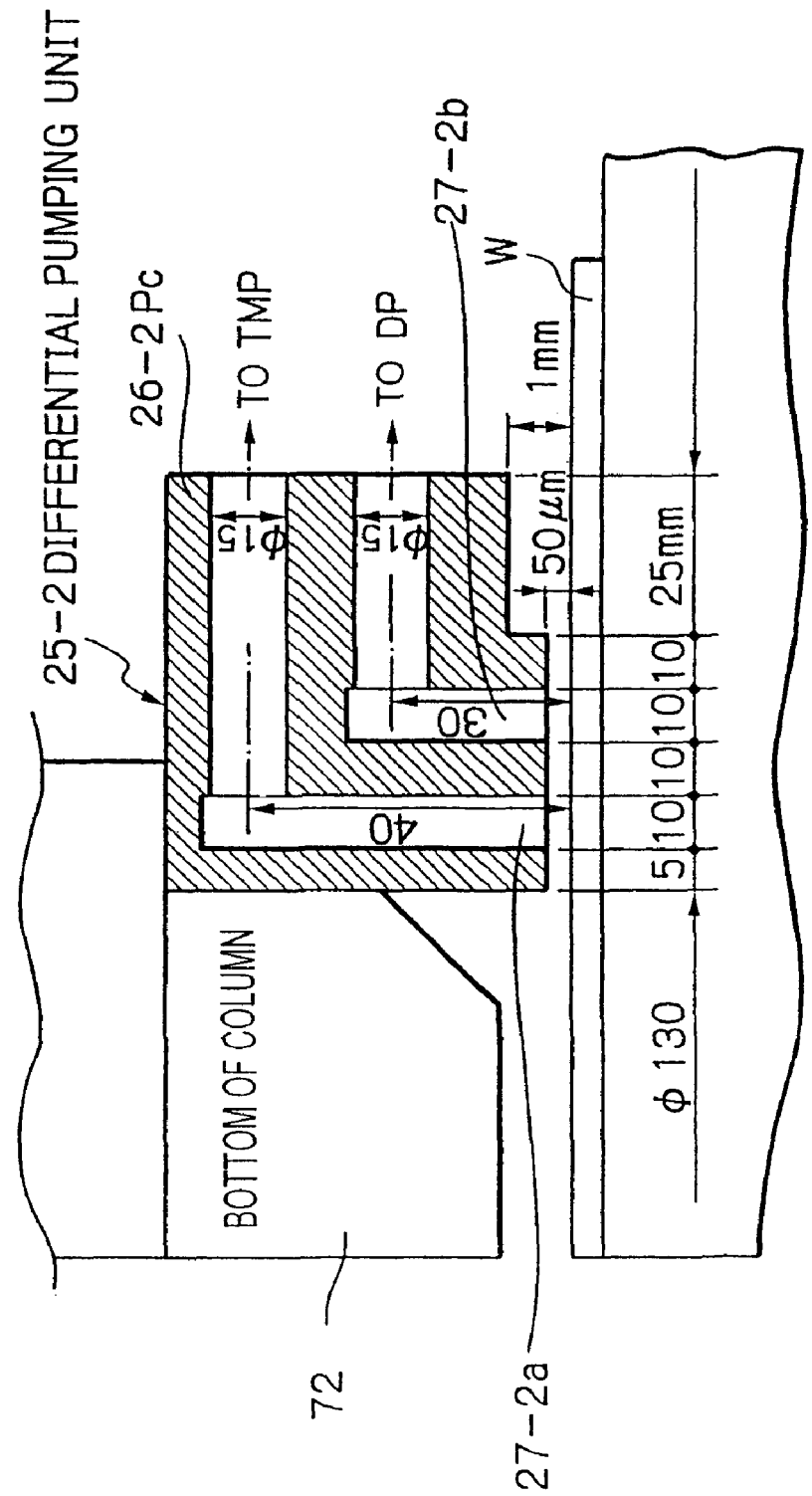
FIG. 22 illustrates an operation emission mechanism installed in the embodiment indicated in FIG. 21.

FIG. 22 shows exemplary values for the sizes of the annular member 26-2 of the differential pumping mechanism, and the annular groove 27-2 formed therein. In this example, the annular groove has a double structure comprised of 27a-2 and 27b-2 which are spaced apart in a radial direction.

A flow rate of the high pressure gas supplied to the hydrostatic bearings is generally at about 20 L/min (converted to the atmospheric pressure). Assuming that the working chamber 31 is evacuated by a dry pump having an pumping speed of 20000 L/min through a vacuum pipe having an inner diameter of 50 mm and a length of 2 m, the pressure in the chamber 31 is approximately 160 Pa (approximately 1.2 Torr). In this event, if the dimensions of the annular member 26-2 of the differential pumping mechanism, annular groove and so on are determined as shown in FIG. 22, the pressure in the electron beam irradiation space 30-2 can be set at $10^{-4}$ Pa ($10^{-6}$ Torr).

Figure 23:
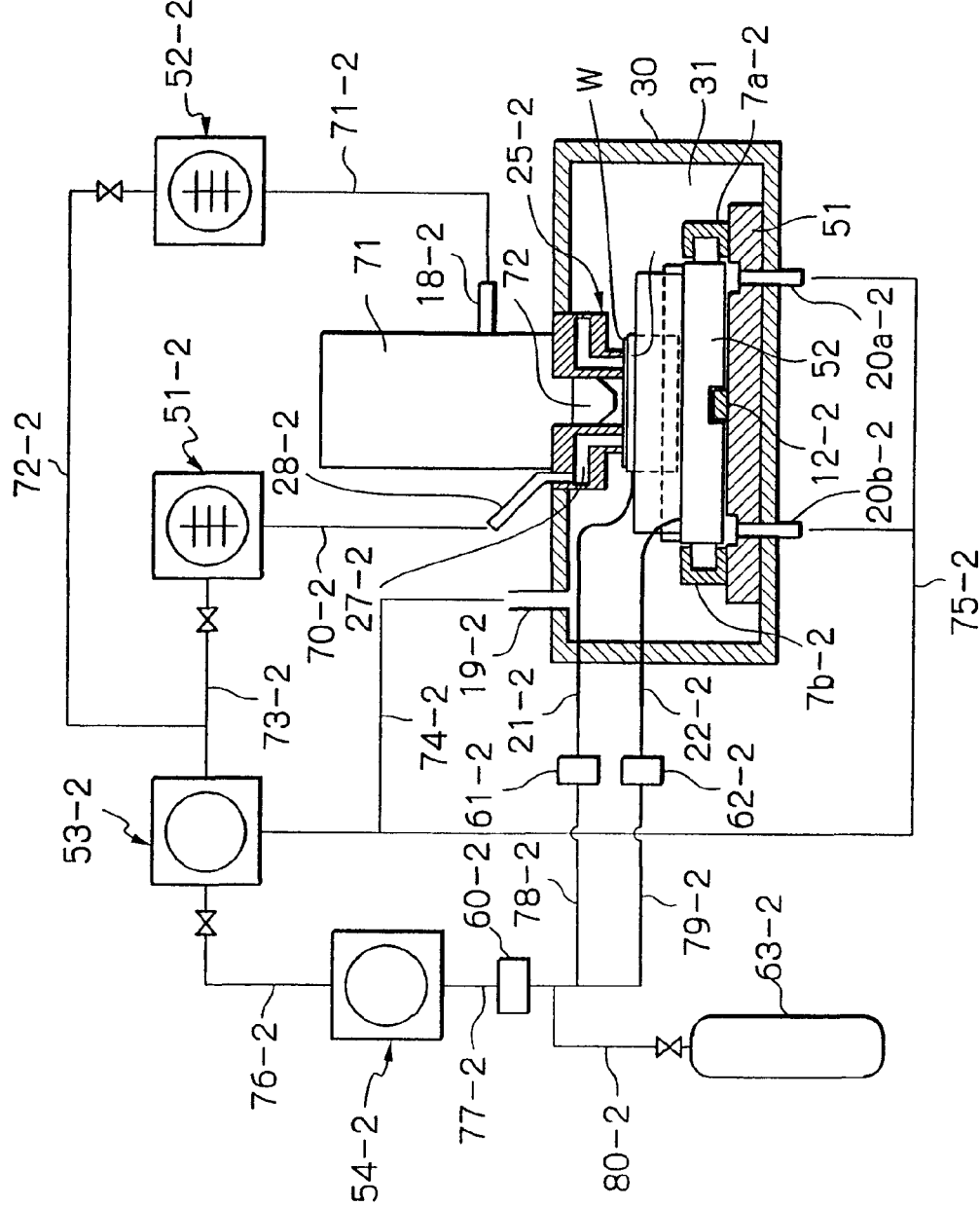
FIG. 23 illustrates a gas circulation piping mechanism installed in the embodiment indicated in FIG. 21.

FIG. 23 illustrates a piping system for the apparatus illustrated in FIG. 22. The working chamber 31 defined is connected to a dry vacuum pump 53-2 through vacuum pipes 74-2, 75-2. Also, the annular grove 27-2 of the differential pumping mechanism 25-2 is connected to a turbo molecular pump 51-2, which is an ultra-high vacuum pump, through a vacuum pipe 70-2 connected to an evacuate port 28-2. Further, the inside of the column 71 is connected to a turbo molecular pump 52-2 through a vacuum pipe 71-2 connected to the evacuate port 18-2. These turbo molecular pumps 51-2, 52-2 are connected to the dry vacuum pump 53-2 through vacuum pipes 72-2, 73-2. (While in FIG. 23, a single dry vacuum pump is in double use for a roughing pump as the turbo molecular pump and a vacuum evacuation pump for the vacuum chamber, it is contemplated that separate dry vacuum pumps may be used for evacuation depending on the flow rate of the high pressure gas supplied to the hydrostatic bearings of the X-Y stage, the volume and inner surface area of the vacuum chamber, and the inner diameter and length of the vacuum pipe.)

The hydrostatic bearing of the X-Y stage are supplied with highly pure inert gas ($N_2$ gas, Ar gas or the like) through the flexible pipes 21-2, 22-2. The gas molecules blown out from the hydrostatic bearings diffuse in the working chamber, and are exhausted by the dry vacuum pump 53-2 through the evacuate ports 19-2, 20a-2, 20b-2. Also, the gas molecules introducing into the differential pumping mechanism and the electron beam irradiation space are sucked from the annular groove 27-2 or the bottom of the column 71, evacuated by the turbo molecular pumps 51-2 and 52-2 through the evacuate ports 28-2 and 18-2, and evacuated by the dry vacuum pump 53-2 after they have been pumped by the turbo molecular pump. In this way, the highly pure inert gas supplied to the hydrostatic bearings is collected and evacuated by the dry vacuum pump.

On the other hand, the dry vacuum pump 53-2 has an evacuate port connected to a compressor 54-2 through a pipe 76-2, while the compressor 54-2 has an evacuate port connected to the flexible pipes 21-2, 22-2 through pipes 77-2, 78-2, 79-2 and regulators 61-2, 62-2. Therefore, the highly pure inert gas exhausted from the dry vacuum pipe 53-2 is again pressurized by the compressor 54-2, regulated to a proper pressure by the regulators 61-2, 62-2, and again supplied to the hydrostatic bearings of the X-Y table.

As described above, the gas supplied to the hydrostatic bearings must be purified as high as possible to maximally exclude moisture and oil components, so that the turbo molecular pumps, dry pump and compressor are required to have structures which prevent moisture and oil components from introducing into gas flow paths. It is also effective to provide a cold trap, a filter or the like (60-2) in the middle of the discharge side pipe 77-2 of the compressor to trap impurities such as moisture and oil components mixed in a circulating gas such that they are not supplied to the hydrostatic bearings.

In this way, since the highly pure inert gas can be circulated for reuse, the highly pure inert gas can be saved. In addition, since the inert gas is not supplied in an uncontrolled manner into a chamber in which the apparatus is installed, the possibility of accidents such as suffocation by the inert gas can be eliminated.

The circulating pipe system is connected to a highly pure inert gas supply system 63-2 which serves to fill the highly pure inert gas into the entire circulating system including the working chamber 31, vacuum pipes 70-2-75-2, and pressurizing pipes 1676-1680, and to supply the shortage if the flow rate of the circulating gas is reduced by some cause.

It is also possible to use a single pump as the dry vacuum pump 53-2 and the compressor 54-2 by providing the dry vacuum pump 53-2 with a function of compressing to the atmospheric pressure or higher. Further, the ultra-high vacuum pump for use in evacuating the column 72 may be implemented by a pump such as an ion pump, a getter pump instead of the turbo molecular pump. However, when such an entrapment vacuum pump is used, a circulating piping system cannot be built in this portion. Also, a dry pump of another configuration such as a diaphragm dry pump may of course be used instead of the dry vacuum pump.

In the constitutions of the electron beam emitting tip and the pumping mechanisms for the space around the emitting tip as described above, the stage apparatus can be accurately positioned in the vacuum working chamber. Further, it is possible to create high quality image data because the pressure around the emitting tip is hardly increased. These constitutions are applicable to embodiments of the electron beam apparatus which will be explained below, as well as the apparatus shown in FIG. 8.

Next, a variety of embodiments of the electron beam apparatus according to the present invention will be described other than the embodiment illustrated in FIG. 8.

Figure 24:
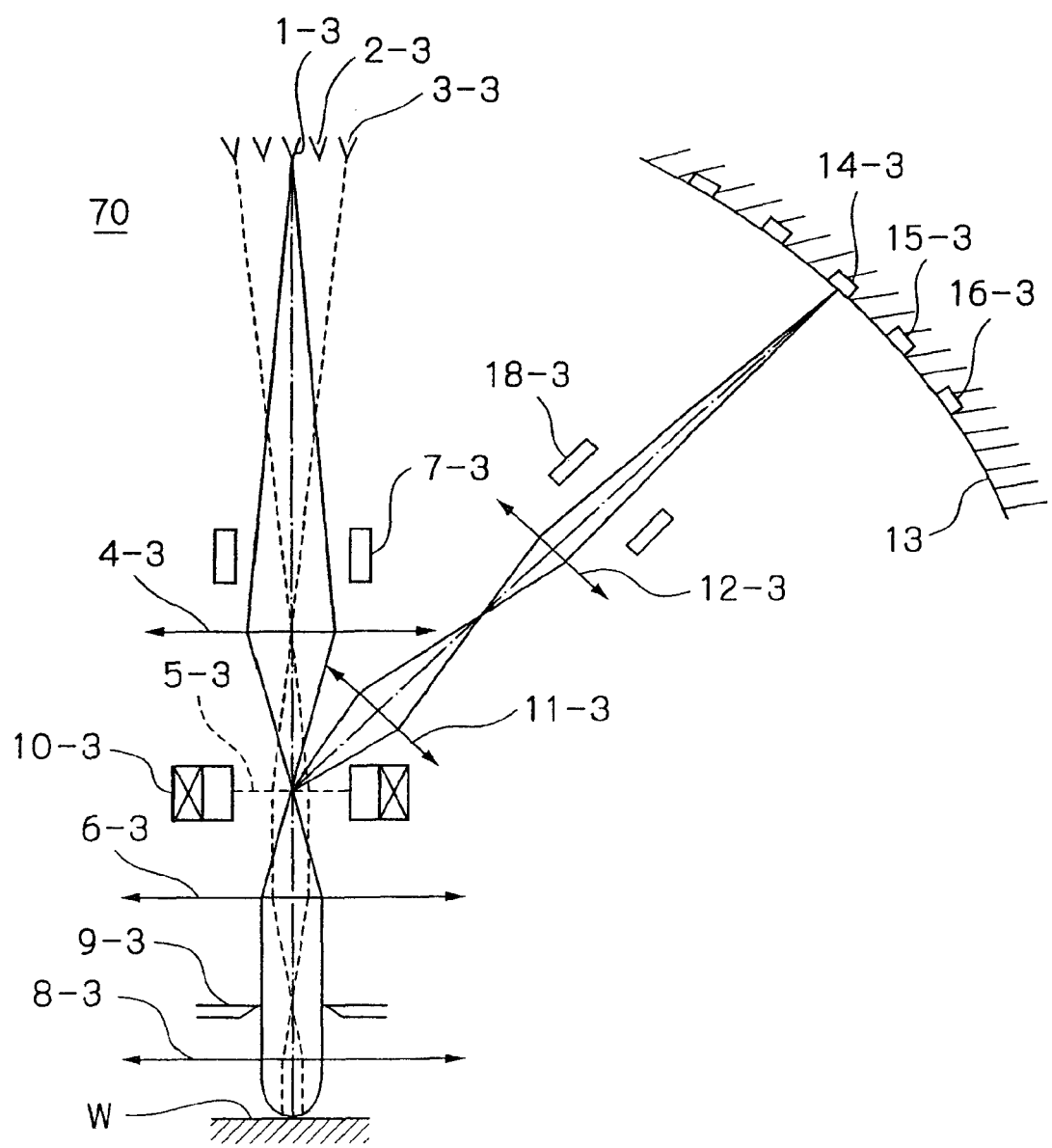
FIG. 24 schematically illustrates an embodiment of an electron optical system contained in an electron beam apparatus of the present invention.

FIG. 24 illustrates an embodiment of an electro-optical system 70 which can be applied to the electron beam apparatus according to the present invention. In this embodiment, an electron gun is constructed to have a plurality of emitters 1-3, 2-3, 3-3, i.e., multiple emitters for emitting multiple beams, and can conduct a desired test even if one of these emitters fails. An electron beam emitted from each emitter is converged by condenser lenses 4-3, 6-3, and forms a cross-over in an aperture 9-3. Then, an image of the primary electron beams or multiple beams, is focused on the surface of a wafer W through an objective lens 8-3.

Secondary electron beams emitted from the wafer W are individually converged by an acceleration electric field created by the objective lens 8-3, and deflected by the ExB separator 10-3 to be separated from the primary optical system. Then, the secondary electron beams are enlarged by enlarging lenses 11-3, 12-3, pass through a multi-aperture plate 13-3 formed with apertures on the same circle, and are detected by detectors 14-3, 15-3, 16-3 to generate electric signals. The generated electric signals are processed in an image processing unit (not shown).

Figure 25:
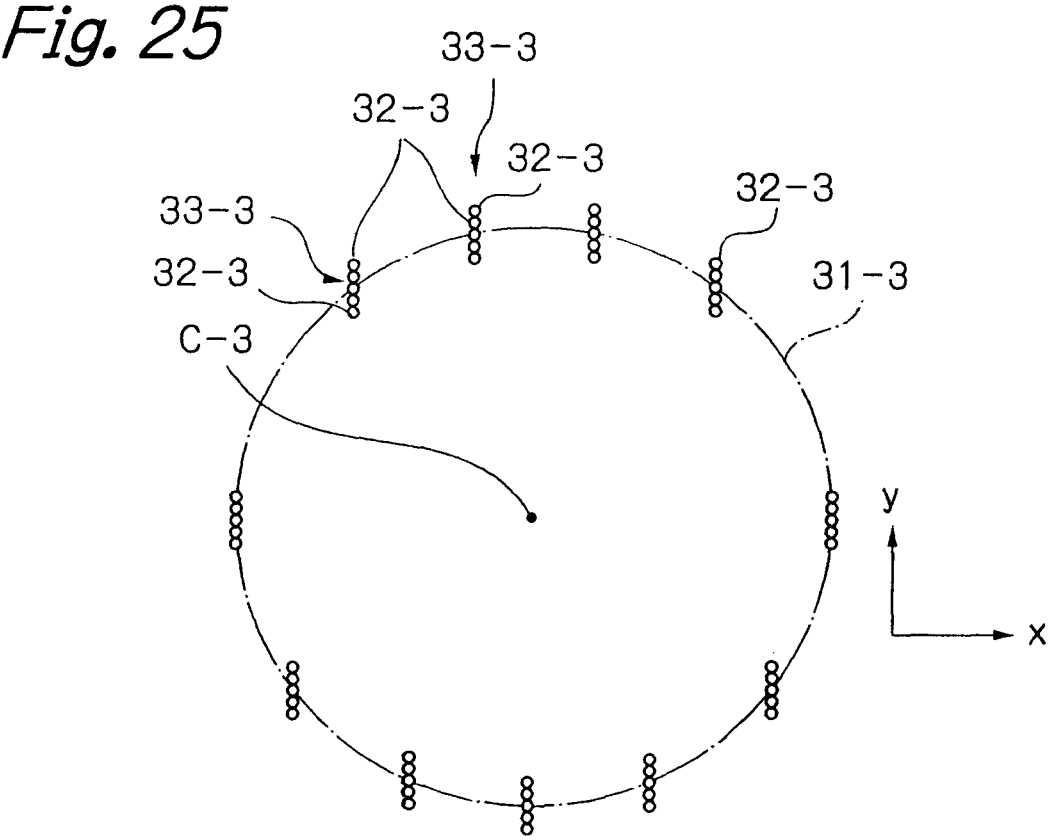
FIG. 25 illustrates an example of an arrangement of emitter chips constituting an electron gun employed in an electron optical system of an electron beam apparatus of the present invention.
Figure 26:
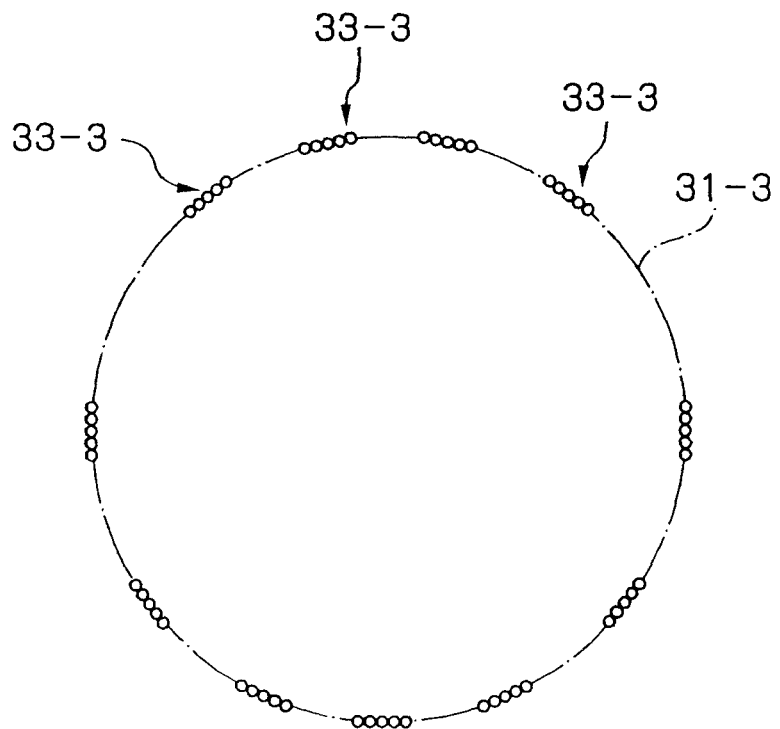
FIG. 26 illustrates another example of an arrangement of emitter chips constituting an electron gun employed in an electron optical system of an electron beam apparatus of the present invention.
Figure 27:
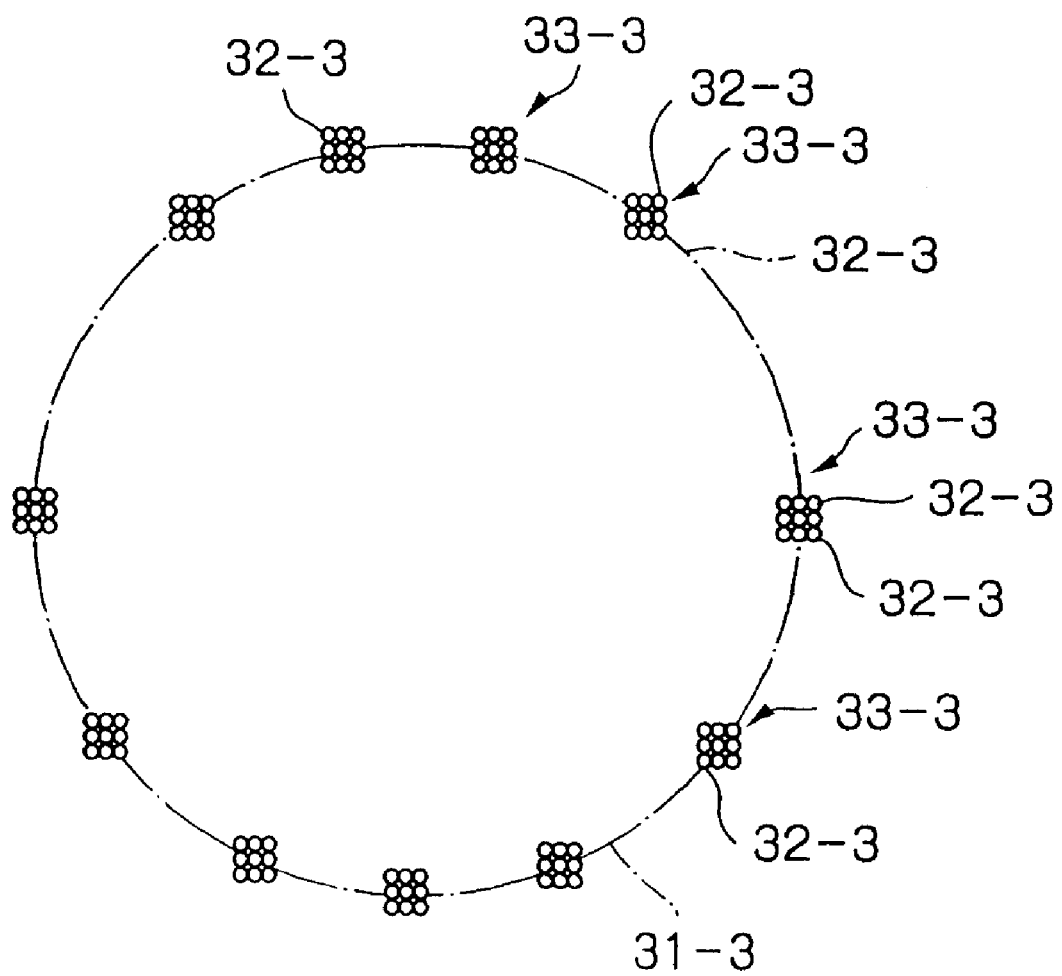
FIG. 27 illustrates still another example of an arrangement of emitter chips constituting an electron gun employed in an electron optical system of an electron beam apparatus of the present invention.

With reference to FIGS. 25 through 27, arrangements of emitter chips, i.e., electron beam emission sources 32-3 of the electron gun will now be described.

In an example illustrated in FIG. 25, the emitter chips 32-3 are linearly arranged in the Y direction to form a plurality of emitter chip groups 33-3. The emitter chip groups 33-3 are positioned on the same circle 31-3 centered at an optical axis C-3, and set such that when they are projected to a line in the X direction (the direction in which the primary electron beams are scanned on the wafer W) orthogonal to the optical axis C-3, the projected images of the emitter chips are spaced substantially at equal intervals in the X direction. This positional relationship is similar to that described above with reference to FIG. 9A. The emitter chips 32-3 in the emitter chip group 33-3 are connected in parallel with power source, so that as one of the emitter chips is arbitrarily selected and only this chip is applied with a voltage, an electron beam can be emitted from the selected emitter chip alone. Since the emitter chip groups 33-3 are spaced from one another as described above, electron beams emitted from emitter chips respectively selected as described above from the emitter chip groups are spaced at equal intervals in the X direction. Therefore, by scanning these electron beams in the X direction only in a spacing between irradiated spots of the electron beams on the surface of the wafer, the wafer is scanned over a width equal to (the spacing between spots)×(the number of emitter chips). Preferably, each of emitter chips is in the shape of cone, quadrangular pyramid, or the like.

In an example of FIG. 26, emitter chip groups 33-3 are comprised of a plurality of emitter chips 32-3 positioned on the same circumference 31-3, and similar to the case of FIG. 26, one arbitrary emitter chip in each emitter chip group can be applied with a voltage. Since the spacing between emitter chips applied with the voltages slightly varies in the X direction depending on the selection of emitter chips, a scanning width must include a margin and be larger than the spacing between the spots described in connection with FIG. 25.

In another example illustrated in FIG. 27, each emitter chip group 33-3 is comprised of emitter chips which are arranged in 3×3 matrix. By arranging them in a matrix, a large margin is not required for the scanning width as compared with the arrangement of the emitter chips illustrated in FIG. 26, and the field curvature can be minimized.

In the electro-optical systems 70 described with reference to FIGS. 24 through 27, the electron gun comprises a plurality of groups of emitter chips, and a voltage is applied to one emitter chip arbitrarily selected from each emitter chip group to generate an electron beam. Therefore, even if any emitter chip fails, another emitter chip in the same group can be used to emit an electron beam, and thus it is possible to avoid a trouble due to a failure of an emitter chip.

Figure 28:
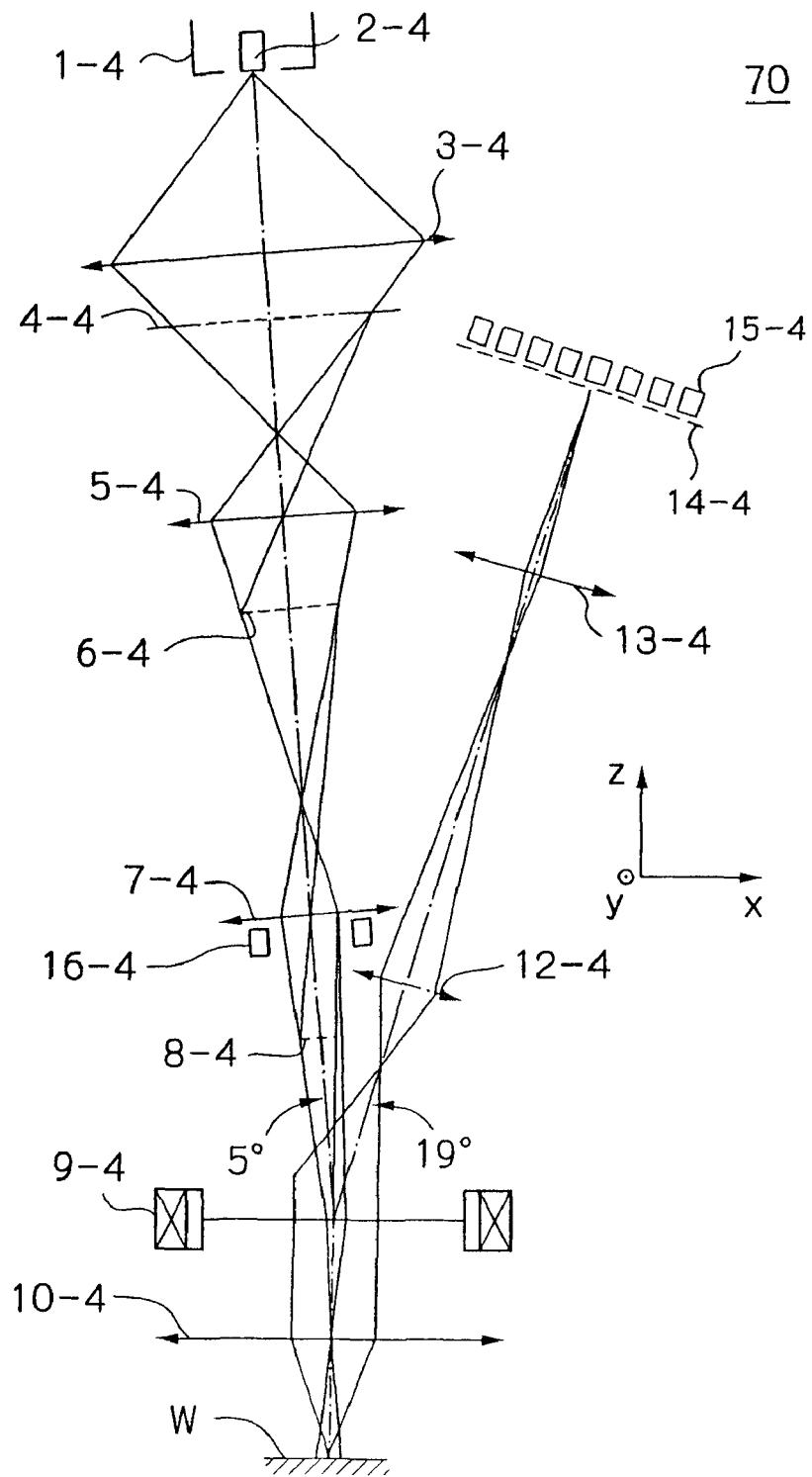
FIG. 28 schematically illustrates another embodiment of an electron optical system contained in an electron beam apparatus of the present invention.

FIG. 28 illustrates another embodiment of the electro-optical system 70 utilized in the electron beam apparatus according to the present invention. In this embodiment, primary electron beams are comprised of multiple beams, and the field curvature aberration, which is the largest one of aberrations of the primary electron beams, can be limited. In this electro-optical system 70, a cathode 2-4 made of an $LaB_6$ single crystal which is processed to be multi-beam emitters, is placed at the center of an electron gun 1-4. An electron beam emitted from the cathode is converged by a condenser lens 3-4 to form a cross-over. A first multi-aperture plate 4-4 is provided between the lens 3-4 and the cross-over, and is positioned such that apertures thereof substantially match locations at which respective beams from the cathodes 2-4 are strong. The beams passing through the multi-aperture plate are demagnified by two stages of reducing lenses 5-4, 7-4, further demagnified by an objective lens 10-4, and focused on a wafer W. In FIG. 28, 6-4 and 8-4 indicate a first and a second reduced image.

Electron beams emitted from the wafer W are converged by an accelerating electric field created by the objective lens 10-4, deflected by an ExB separator 9-4 to be separated from the primary optical system, enlarged by enlarging lenses 12-4, 13-4, and detected by detectors 15-4 after passing through a second multi-aperture plate 14-4 having apertures arranged on the same circle, thereby they are converted to electric signals. The resulting electric signals are processed in an image processing unit (not shown).

The electron gun 1-4 comprises a $LaB_6$ single crystal cathode of a thermal electron emission type. The shape of the cathode 2-4 at a bottom is illustrated in detail in FIG. 29 (front view) and FIG. 30 (side view). The cathode is generally made of an $LaB_6$ single crystal in the shape of a 2 mmϕ cylinder. As illustrated, the bottom is cut at an angle 22-4 of 45°, and an annular protrusion 23-4 having a triangular cross-section is left along the peripheral edge of a bottom surface 24. Then, portions of the annular protrusion are cut off to form a plurality of protrusions in the shape of quadrangular pyramid having an incline 26-4 angled at 45°, i.e., emitter regions 25-4. These emitter regions are set such that when they are projected to a line in the X direction (the direction in which the primary electron beams are scanned on the wafer W) orthogonal to the center line of the bottom surface 24-4 (the center line matches the optical axis of the primary electro-optical system), the projected emitter regions are spaced substantially at equal intervals in the X direction. This positional relationship is similar to that described above in connection with FIG. 9A. To prevent electrons from being emitted from regions between the respective emitter regions and the bottom surface 24-4 inside the emitter regions, a sufficient difference in height is taken between the bottoms of the emitter regions and these portions.

Figure 29:
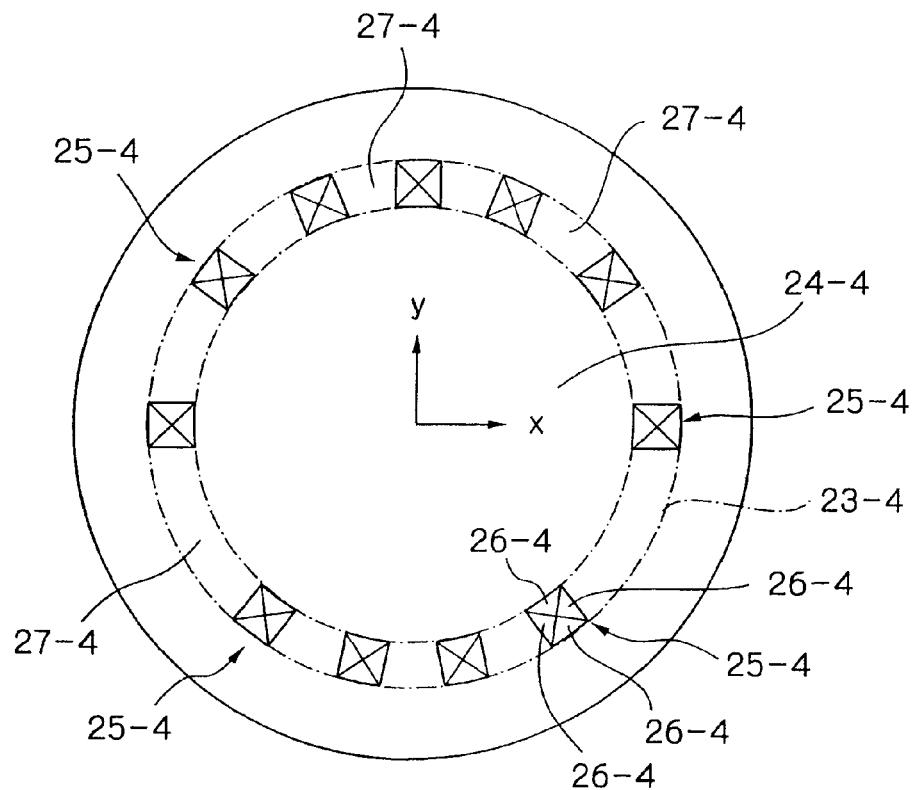
FIG. 29 is a plan view of a cathode tip portion (emitter) of an electron gun applicable to an electron optical system contained in an electron beam apparatus of the present invention.
Figure 30:
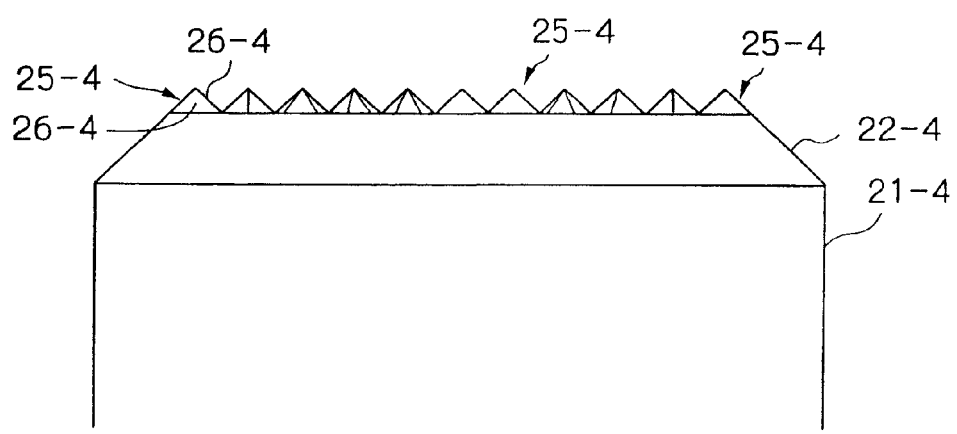
FIG. 30 is a side view of the cathode shown in FIG. 29.

The electron gun having the cathode structure illustrated in FIGS. 29 and 30 not only can be used as the electron gun for the electro-optical system in the third embodiment illustrated in FIG. 28, but also can be used as the electron gun for the electro-optical system in the first embodiment illustrated in FIG. 8. Further, it can be used as an electron gun for other embodiments of the electro-optical system 70 described below.

In the electro-optical system in the electron beam apparatus described with reference to FIGS. 28 through 30, multiple beams can be properly generated by a single electron gun. In addition, since the field curvature can be substantially corrected, a large number of beams can be generated with the same aberration, thereby making it possible to significantly improve the throughput of a testing apparatus.

Figure 31:
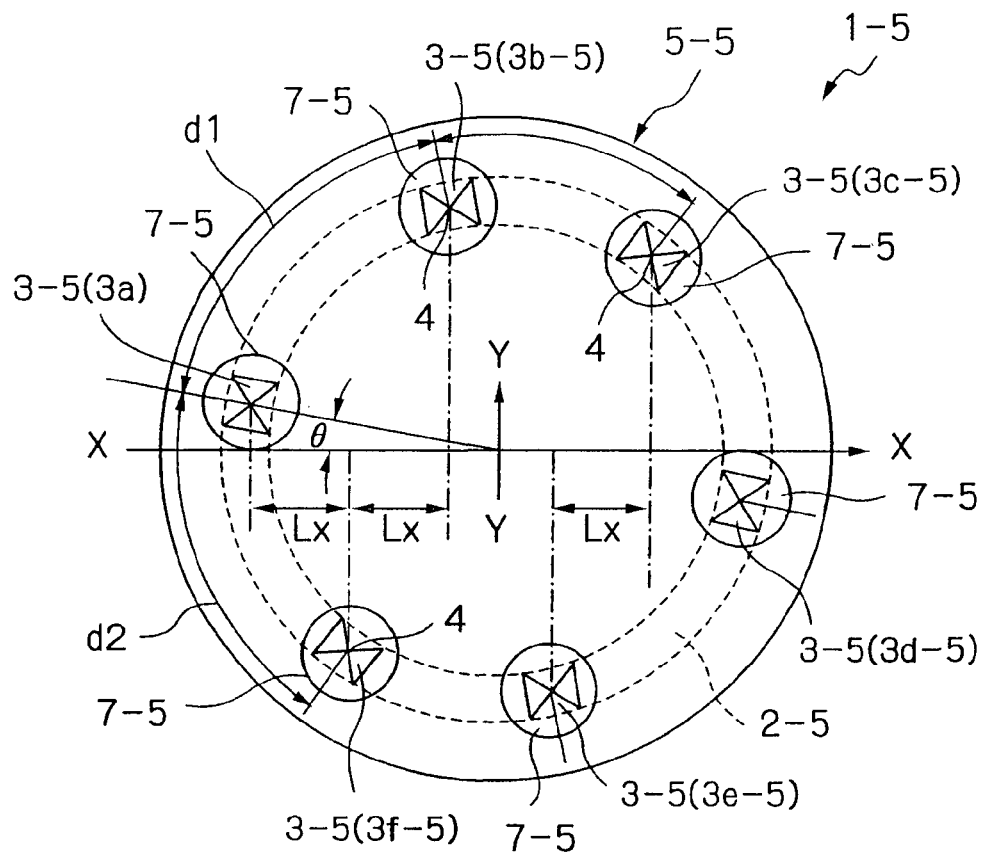
FIG. 31 is a plan view of a cathode tip portion of an electron gun applicable to an electron optical system installed in an electron beam apparatus of the present invention.
Figure 32:
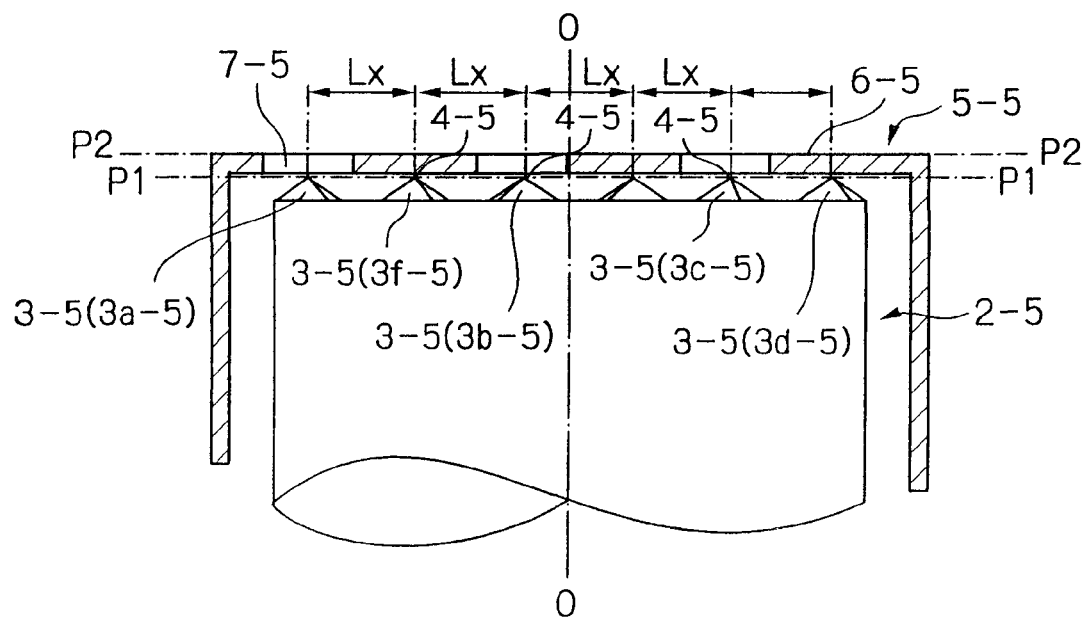
FIG. 32 is a side view illustrating a relationship between an emitter of the cathode shown in FIG. 31 and a Wehnelt.
Figure 33:
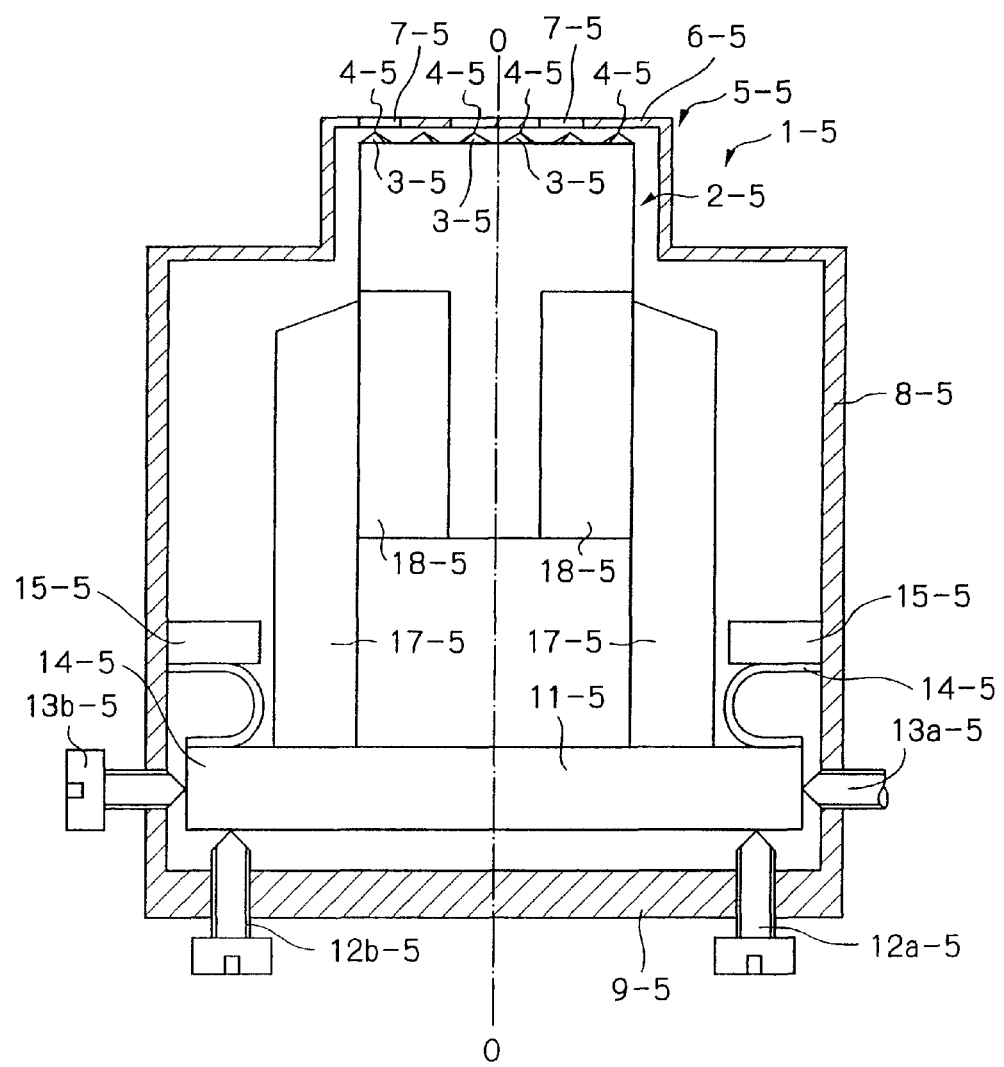
FIG. 33 is a cross section illustrating an alignment mechanism for aligning an emitter of a cathode with an opening of a Wehnelt.

FIGS. 31 through 33 are a plan view and side views (partially cross-sectional views) illustrating another embodiment of an electron gun which can be applied to the electro-optical system 70 in the electron beam apparatus according to the present invention. These drawings illustrate, in enlarged view, the vicinities of a cathode and a Wehnelt which constitute an electron beam emission region of the electron gun. The electron gun of this embodiment can also be used as an electron gun for any embodiment of the electron beam apparatus according to the present invention. The electron gun of this embodiment is capable of generating multiple beams with high performance, and moreover, the cathode of the electron gun can be readily aligned with a control electrode.

As illustrated in FIGS. 31 and 32, an electron gun 1-5 of this embodiment comprises a cylindrical cathode body 2-5, and a control electrode, i.e., a Wehnelt 5-5 arranged to surround a bottom of the cathode body 2-5. The columnar cathode 2-5 has, at the bottom thereof, a plurality of (six in this embodiment) emitters 3-5 which form electron beam emission regions. These emitters 3-5 have sharp peaks 4-5 formed by machining the bottom of the cathode 2-5 into tapered shapes (pyramidal shapes), and emit electron beams from the bottoms. The position of the emitter 3-5 on the bottom of the cathode is previously determined such that the distance Lx between mutually adjacent ones of the positions which are formed by projecting the peaks 4-5 of the respective emitters on the X-axis, is constant. This relationship is similar to that described above with reference to FIG. 9A. Also, the peaks of all the emitters 3-5 are formed to be present on the same plane P1-P1, as illustrated in FIG. 32. Although the two-dimensional interbeam distances, i.e., the two-dimensional distance between the peaks of the emitters 3-5 cannot be made equal to one another, distances d1 and d2 in the circumferential direction between the peak of an emitter 3a-5 and peaks of adjacent emitters 3b-5 and 3f-5 can be made equal to each other by optimally selecting an angle θ formed by a line which connects the bottom of the emitter 3a-5 with an axial line 0-0 of the cathode 2-5, which defines the optical axis of the electron gun 1-5, and the X-axis, as illustrated in FIG. 31. The control electrode, i.e., the Wehnelt electrode 5-5 has a cylindrical end closed by an end wall 6-5, as is apparent from FIG. 32. The end wall 6-5 has through holes or apertures 7-5 positioned correspondingly to the respective emitters 3. The Wehnelt electrode may have a single aperture of such dimensions that surround all the emitters.

The number of electron beam emission regions, i.e., emitters formed at the bottom of the cathode may be an arbitrary plural number equal to or larger than two. The shape of the emitter is not limited to the pyramidal shape illustrated in FIGS. 31 and 32, but may be in an arbitrary shape such as a cone, by way of example, as long as such a shape can emit electron beams from its bottom. The cathode and Wehnelt may be formed of the same materials as those in a conventional electron gun. Further, the size of the openings 7 formed through the Wehnelt can be determined as appropriate.

The throughholes 7-5 need to be correctly positioned with respect to the emitters 3-5. The positioning is performed by an alignment mechanism illustrated in FIG. 33. In FIG. 33, the Wehnelt electrode 5-5 is attached to a bottom of a cylindrical supporting base 8-5. A base plate 11-5, which forms a part of the alignment mechanism, is disposed in the supporting base 8-5. The base plate 11-5 is made of an insulating material, and carried on a plurality (in this embodiment, a total of four, two each on the X and Y-axis lines, though only two on the X-axis are shown in the drawing) of adjustable screws 12a-5, 12b-5 screwed into a bottom plate 9-5 of the supporting base 8-5. Between the base plate 11-5 and a spring receptacle 15-5 fixed on the supporting base 8-5, a spring (a leaf spring in this embodiment) 14-5 is interposed, so that the base plate 11-5 is normally urged by this spring toward the adjustable screws 12a-5, 12b-5. Preferably, the spring and spring receptacle are arranged at positions corresponding to the adjustable screws 12a-5, 12b-5. On the supporting base 8-5, a plurality (in this embodiment, a total of four, two each on the X and Y-axis lines, though only two on the X-axis are shown in the drawing) of adjustable screws 13a-5-8b-5 are screwed into the supporting base 8-5. The adjustable screws 12a-5, 12b-5 can adjust the position of the base plate 11-5 in the vertical direction, while the adjustable screws 13a-5, 13b-5 can adjust the position of the base plate 11-5 in the X and Y directions. The cathode 2-5 is fixed over the base plate 11-5 through a plurality of mounting members 17-5. 18-5 designates a heating pyrolic graphite for heating the cathode.

While in this embodiment, a leaf spring is employed as the spring, a coil spring or another arbitrary elastically deformable elastic material may be used.

In the alignment mechanism illustrated in FIG. 33, the Wehnelt and cathode have been previously machined such that all the emitters 3-5 are simultaneously aligned with all the through holes or apertures 7-5 of the Wehnelt electrode 5-5, by matching a rotating direction (a rotating direction about the axial line 0-0 in FIG. 33), X direction (in the left-to-right direction on the sheet surface in FIG. 33), Y direction (in the direction vertical to the sheet surface in FIG. 33), and inclination of the cathode 2-5 with respect to the Wehnelt electrode 5-5. Considering the alignment in the rotating direction, errors can be limited within a range determined by the accuracy during machining, if the alignment mechanism is manufactured to prevent relative rotation of the cathode 2-5 to the Wehnelt electrode 5-5.

An adjustment in the X direction is made using a pair of the adjustable screws 12a-5 and 12b-5 arranged on the X-axis, and an adjustment in the Y direction is made using a pair of adjustable screws (not shown) positioned on the Y-axis (in FIG. 33, an axial line which intersects the axial line 0-0 and is orthogonal to the sheet surface). When the inclination of the plane P1-P1 (FIG. 32) with the plane on which the apertures exist (here, the plane on which the top surface of the end wall is positioned), i.e., a plane P2-P2 (FIG. 32) is wrong, the distance between the cathode and the Wehnelt in the Z direction (the direction vertical to the sheet surface in FIG. 33) is changed, so that the inclination is adjusted by the adjustable screws 12a-5, 12b-5, and two adjustable screws not shown (or two adjustable screws arranged in the direction vertical to the sheet surface).

According to the electron gun as described above, the relative position of each of the multiple emitters to the each of the apertures of the Wehnelt can be made identical to that of a single beam. Therefore, the intensity of each of the multiple beams can be made substantially similar to that of the single beam.

FIGS. 34 through 38 are diagrams for explaining further embodiments of the electron gun which can be employed in the electro-optical system 70 in the electron beam apparatus according to the present invention. Likewise, the electron gun of this embodiment is applicable as the electron gun for embodiments of the electro-optical system described below, other than the aforementioned embodiments of the electro-optical system 70. The electron gun of this embodiment is capable of emitting multiple beams having a relatively large beam current with small temporal fluctuations.

Figure 34A:
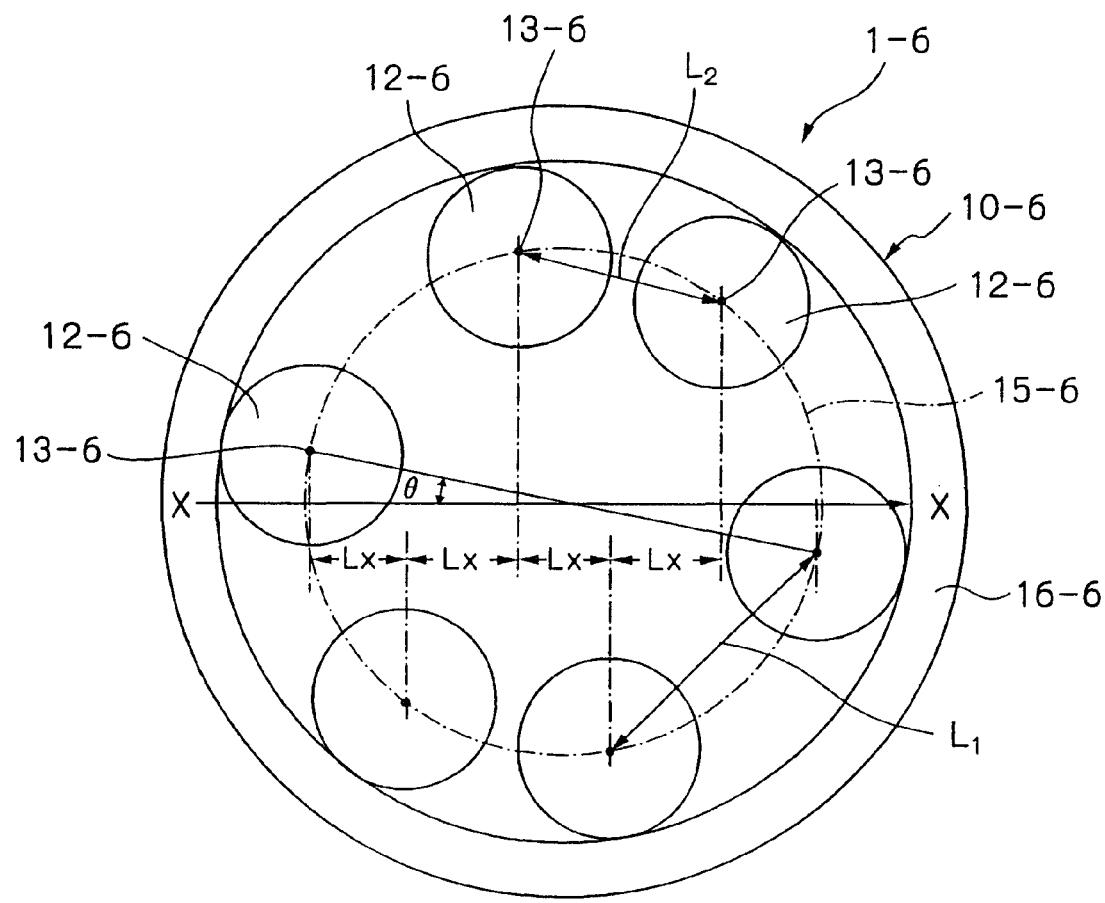
FIG. 34A is a plan view of a cathode tip portion of an electron gun applicable to an electron optical system contained in an electron beam apparatus concerning the present invention.
Figure 34B:
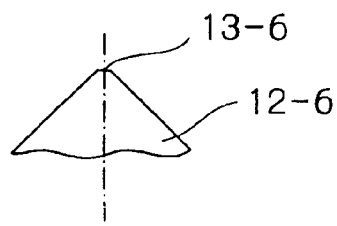
FIG. 34B is a side view of emitters thereof.
Figure 35:
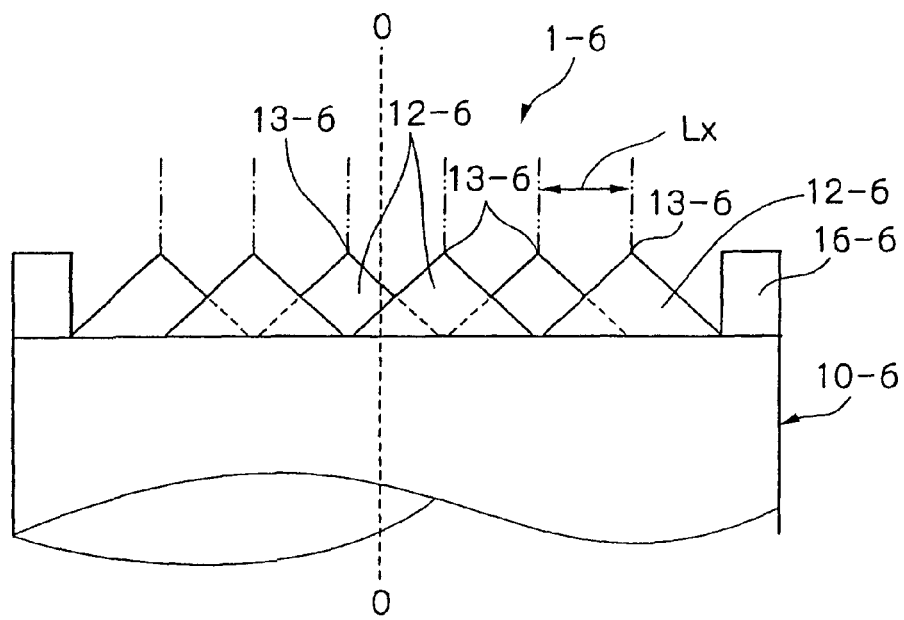
FIG. 35 is a side view of the cathode shown in FIG. 34.
Figure 36A:
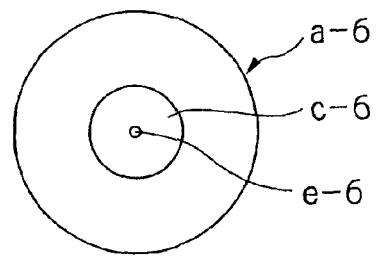
FIGS. 36A and 36B are plan and side views of a machine tool for machining an emitter of the cathode shown in FIGS. 34 and 35.

FIGS. 34A and 35 illustrate a plan view and a side view of a bottom of a cathode 1-6 for use in the electron gun. The cathode 1-6 is formed by machining an $LaB_6$ column 10-6 having an end surface defined by a (100) surface of a single crystal $LaB_6$ and an outer diameter d1. The end surface of this column is mirror polished, and two surfaces perpendicular to the end surface and held by carbon are also polished into parallel plain surfaces. When the $LaB_6$ column 10-6 is machined to form the cathode, a jig borer is used. A tool a-6 made of a grinding stone having the structure shown in FIG. 36 is mounted on the jig borer in place of a drill, and using this tool a-6, the $LaB_6$ column 10-6 is cut to and shaped to form a predetermined number (six in this embodiment) of conical protrusions, i.e., emitters 12-6 are formed on a circle 15-6 centered at an optical axis. Bottoms 13-6 of the emitters 12-6 form emission regions which can emit strong electron beams, as illustrated in FIG. 34B. As can be seen from the structure of the tool a-6 illustrated in FIG. 36 and described later, extremely small plain surfaces (10-50 μmφ) comprised of polished end surfaces of the cylinder are left on the bottom 13-6, without cutting by the tool, and electron beams are emitted from these plain surfaces. The number of the emitters 12-6 is six so that six electron beams can be generated in this embodiment, and the positions of the emitters 12-6 are determined such that spacing distances Lx between adjacent ones of the positions formed by projecting the centers of the respective emitters 12-6, i.e., the bottoms 13-6 onto the X-axis are all equal to one another. This is similar to that described in connection with FIG. 9A. The positions of the emitters can be correctly determined as limited by the accuracy of the jig borer. By optimizing the angle θ formed by the X-axis and a line passing the bottom 13-6 of one emitter 12-6a and the axial line 0-0 of the cathode (FIG. 35), the ratio of a maximum value L1 to the best value L2 of the spacing distance between electron beams is approximated to 1.0. This can be optimized by varying the diameter of the circle centered at the optical axis, and creating a design drawing with the value of the spacing Lx being fixed.

Figure 36B:
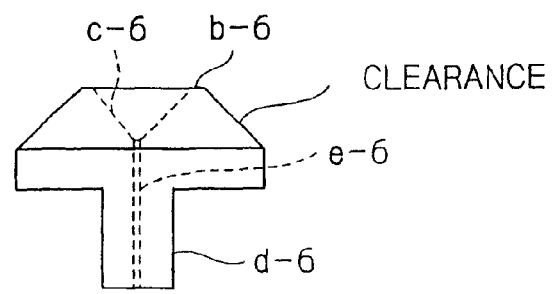

The tool a-6 illustrated in FIG. 36 comprises a mounting portion d-6 of a small diameter, for mounting on the jig borer, on one end side (on the lower side in FIG. 36B) of a columnar grinding stone; and a conical hole c-6 in an end surface d-6 on the other end side. The conical surface having the end surface b-6 and the conical surface constitutes a cutting surface to be used to cut the end surface of the $LaB_6$ column 10-6. The tool a-6 is further formed with an axial hole e-6 which extends from the bottom of the conical hole c-6 in the axial direction of the tool. This hole is provided for confirming through light whether a conical protrusion constituting an emitter is formed at a correct position. In addition, a coolant and an abrasive material may be introduced from this hole. When cut with this tool a-6, small ground plain surfaces are left on the leading surface of the cone, without being cut, due to the existence of the axial hole, as described above. Alternatively, in place of the grinding stone, a cutting tool having diamond grains embedded in a metal may be used.

Figure 37:
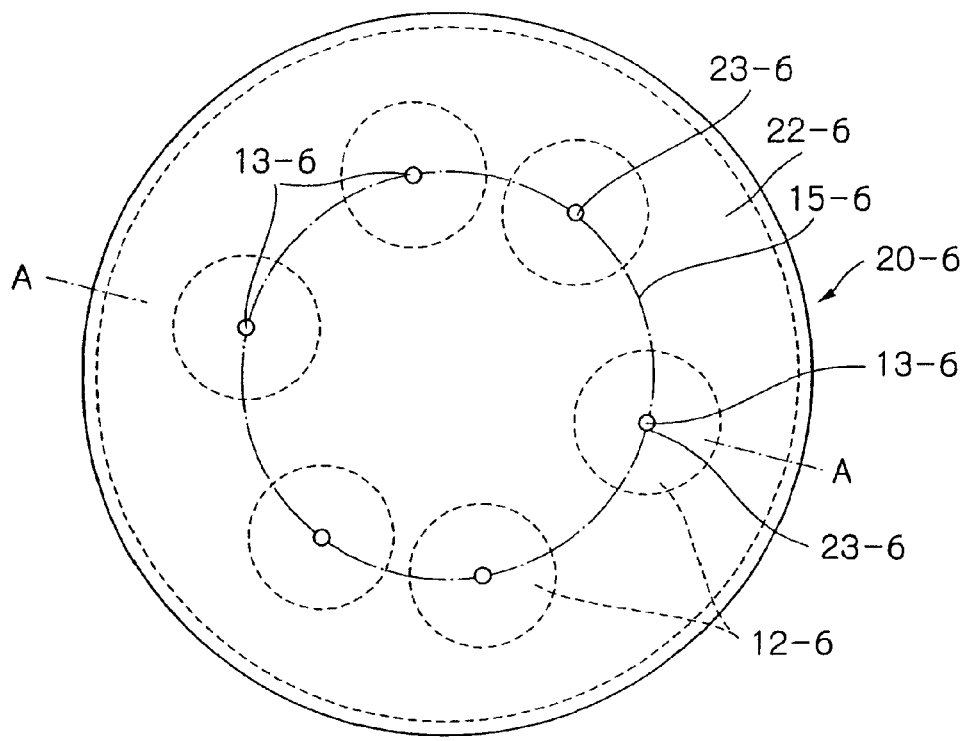
FIG. 37 is a plan view of a Wehnelt constituting, together with the cathode shown in FIG. 34, an electron gun.
Figure 38:
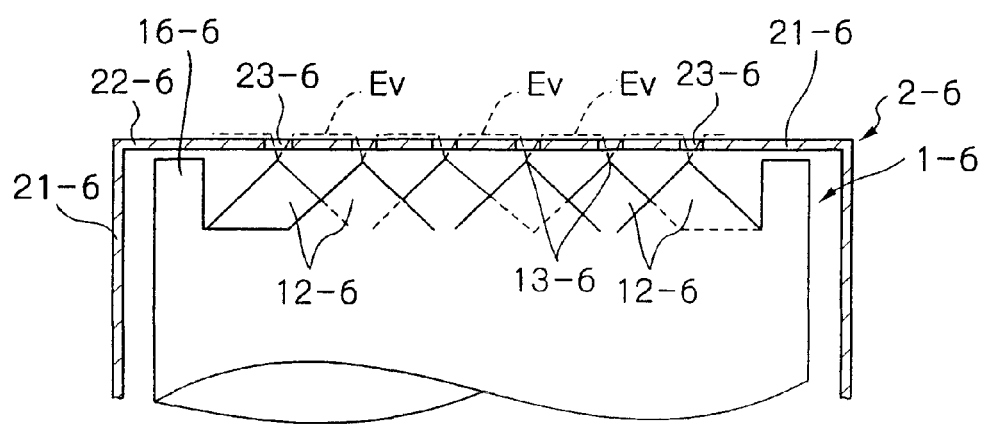
FIG. 38 is a cross sectional view showing the state where the cathode shown in FIG. 34 and the Wehnelt shown in FIG. 37 are combined.

FIGS. 37 and 38 illustrate the structure which is a combination of the cathode 1-6 and Wehnelt 2-6 illustrated in FIGS. 34 and 35. The Wehnelt 2-6 comprises a cylinder section 21-6 surrounding the circumference of the cathode 1-6, and an end wall 22-6 surrounding the end surface. The end wall 22-6 is formed with a plurality (six in this embodiment) of throughholes or apertures 23-6 aligned to the positions of the bottoms 13-6 of the emitters on the cathode. Since the equi-potential surface near the throughholes 23-6 of the Wehnelt 2-6 is recessed toward the emitters at the positions of the holes 23-6, as indicated by a dotted line Ev, electron beams emitted from the emitters are drawn out. Since the end portion of the cathode 1-6 (except for the bottom regions of the emitters) is surrounded by the end wall 22-6 of the Wehnelt 2-6, even if an uncut portion 16-6 exists on the end surface of the cylinder 10-6, no throughhole is formed in the end wall of the Wehnelt corresponding to that position, so that no electron beam will be emitted to the outside. Therefore, the shape of the cathode at a position except for those facing the holes 23-6 may be anyhow.

In essence, it is only required that the $LaB_6$ conical is accurately left as the emitter and the aforementioned extremely small ground plain surfaces (10-50 μmφ) are left on the bottoms of the emitter. Also, cut traces may be left on the inclines of conical emitters. Furthermore, the areas of the plain surfaces at the bottoms of the respective emitters may vary as long as the total area of all (six in this embodiment) the plain surfaces is equal to or less than 100 μm².

While the foregoing embodiment of the electron gun has been described for the emitter the shape of which is conical, the shape of the emitter is not limited to be conical, but may be pyramidal (for example, in the shape of quadrangular pyramid).

In the electron gun described above, since a fine grinding stone is used for grinding and machining, a rigid and fragile crystalline material such as $LaB_6$ can be machined. Also, since the positional accuracy of the emitters is determined by the accuracy of the jig borer, an accuracy of approximately 50 μm can be achieved. Also, since the plain surfaces at the bottoms of the emitters are machined only in the initial mirror polishing, the positions in the optical axis and the surface roughness are held in a high accuracy. Moreover, since the cathode portions other than those facing the throughholes of the Wehnelt may have any shape, the cathode is easy to manufacture.

FIGS. 39 through 42 illustrate other embodiments of an electron gun which is applicable to the electro-optical system 70 comprised in the present invention. Likewise, the electron gun of this embodiment can be used as an electron gun for any electro-optical system 70 in the electron beam apparatus according to the present invention. Also, this embodiment of the electron gun facilitates the manufacturing of a cathode for emitting multiple beams, and is capable of emitting multi-beams without variations in intensity.

Figure 39A:
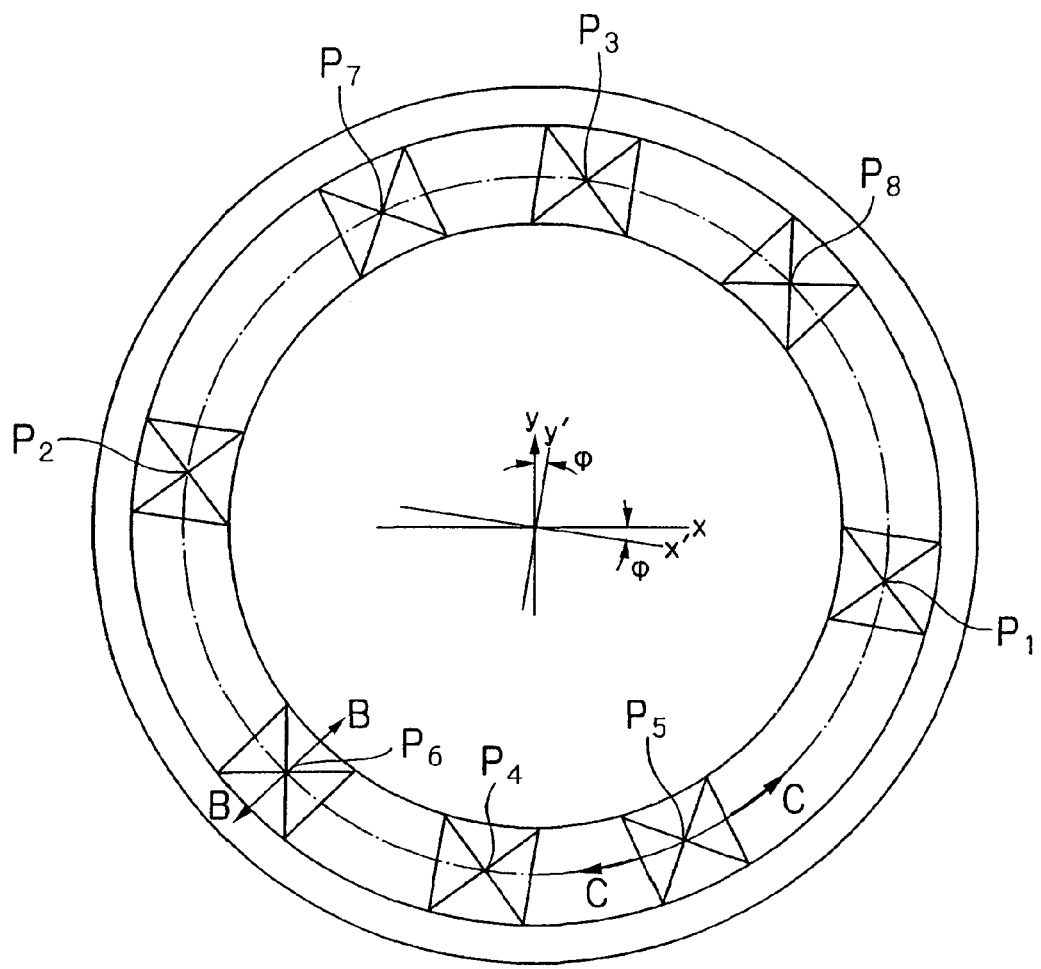
FIG. 39A is a plan view of a cathode tip portion of an electron gun applicable to an electron optical system contained in an electron beam apparatus concerning the present invention.
Figure 39B:
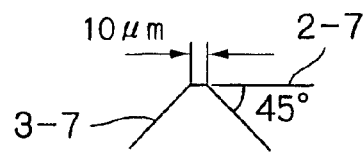
FIGS. 39B and 39C are side views of emitters thereof.
Figure 39C:
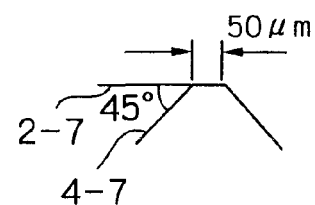

FIG. 39 illustrates the shape of a bottom of a cathode in the electron gun of this embodiment, wherein FIG. 39A is a top plan view, FIG. 39B is a cross-sectional view taken along a line B-B in FIG. 39A, and FIG. 39C is a cross-sectional view taken along a line C-C in FIG. 39A. A method of manufacturing the cathode illustrated in FIG. 39 will be described. First, a Ta (tantalum) single crystal with an end surface having a crystal orientation <310> is used, and one surface thereof is mirror polished to form a mirror surface 2-7 (FIGS. 39B and 39C). Then, two surfaces 1-7 (FIG. 40) exhibiting a good orthogonality to the mirror surface 2-7 are formed, and heated as sandwiched by graphite. Subsequently, both sides of the mirror surface 2-7 are cut at an angle of approximately 45° while leaving a circumference having a width of 10 μm in the radial direction at a position of the mirror surface 2-7 at which a protrusion is formed for the cathode. In this manner, as illustrated in FIG. 39B, a ridge-shaped solid is formed having a mirror surface circumference with a radial width of 10 μm, and two opposing inclines 3-7 with a relative angle, i.e., an apical angle of approximately 90°.

Next, orthogonal X-axis and Y-axis are determined, and directions X' and Y' forming an angle φ to these two axes are determined. The X-axis indicates a direction in which the electron beams are scanned, and the Y-axis indicates the direction orthogonal to that. φ is, for example, 5°. Then, four points P1-P4, crossing in the X' and Y' directions are marked on the circumference of the ridge-shaped solid, and another four points P5-P8 are marked. In this event, the value of the angle φ is determined and points P5-P8 are positioned such that the eight points P1-P8, when projected onto the X-axis, are spaced at equal intervals (similar to the arrangement illustrated in FIG. 9A). Then, eight quadrangular truncated conical protrusions having the points P1-P8 as peaks, and substantially rectangular bases are formed by cutting the ridge-shaped solid (FIG. 39A). The protrusions formed in this event is as shown in FIG. 39C, wherein a top surface has a width of 50 μm in the azimuth direction (circumferential direction), and two inclines 4-7 formed by the new cutting have an angle of approximately 45° to the mirror surface 2-7, therefore, the relative angle, i.e, an apical angle of the two inclines is set to approximately 90°.

In the foregoing manner, eight quadrangular truncated conical protrusions each with a top surface having a rectangular shape of 10 μm×50 μm, which, when projected onto the X-axis, are spaced at equal intervals, are formed as illustrated in FIG. 40.

Since a Ta single crystal is available at a relatively low cost and readily machined, the cathode can be readily manufactured. Though its work function is relatively high, i.e., 4.1 eV, it can be used if the cathode temperature is increased.

Figure 41:
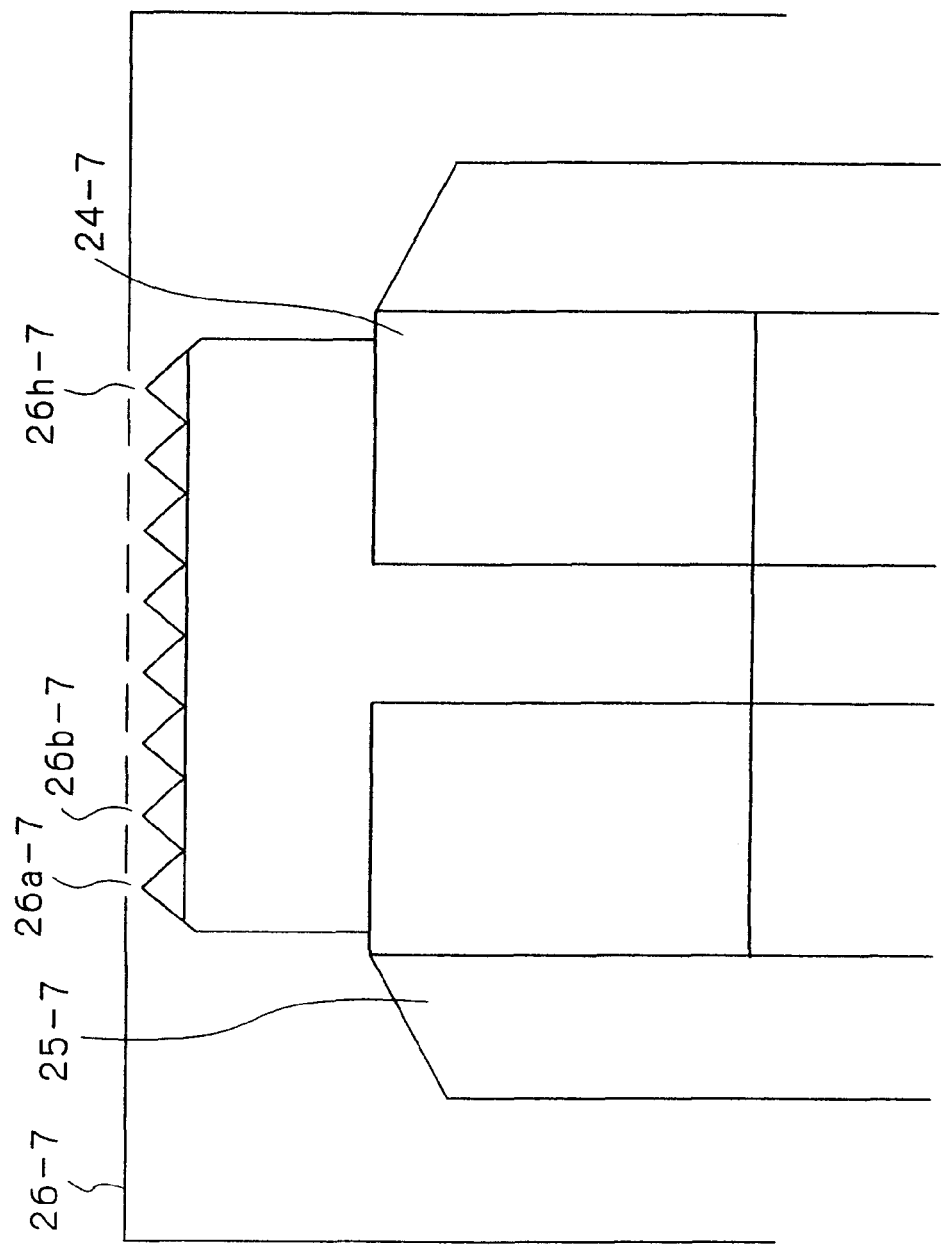
FIG. 41 is a side view of an electron gun in which the cathode shown in FIG. 39 is incorporated.

FIG. 41 illustrates a main portion of an electron gun which comprises such a cathode as illustrated in FIGS. 39 and 40, wherein 24-7 designates graphite; 25-7 a supporting electrode; and 26-7 a Wehnelt electrode. The cathode is sandwiched by the graphite 24-7, and supported by the supporting electrode 25-7. The Wehnelt electrode 26-7 which covers the entire surface of the cathode is formed with eight through-holes 26a-7-26h-7 corresponding to the protrusions on the cathode, and the center of each throughhole is aligned to the center of a corresponding protrusion by adjusting the supporting electrode 25-7 in the X and Y directions.

Further, the parallelism of the surface of the Wehnelt electrode 26-7 to a plane which connects the bottoms of the cathode requires an accuracy. In other word, the distances between the surfaces of the holes of the Wehnelt electrode 26-7 and the cathode in the optical axis direction must be substantially identical for all of the eight protrusions. Therefore, the supporting electrode 25-7 is provided with a device (not shown) for adjusting the inclination of the cathode. Also, for matching absolute values of the distances in the optical axis direction, a device (not shown) is provided for moving the Wehnelt electrode 26-7 in the optical axis direction.

FIG. 42 is a diagram for explaining a further embodiment of the electron gun which can be applied to the electro-optical system 70 in the electron beam apparatus according to the present invention. Likewise, the electron gun of this embodiment can be used as an electron gun for any electro-optical system 70 in the electron beam apparatus according to the present invention. Also, this embodiment facilitates the manufacturing of a cathode for emitting multiple beams, and is capable of emitting multi-beams without variations in intensity. FIG. 42 illustrates only the cathode of the electron gun in this embodiment.

Figure 42A:
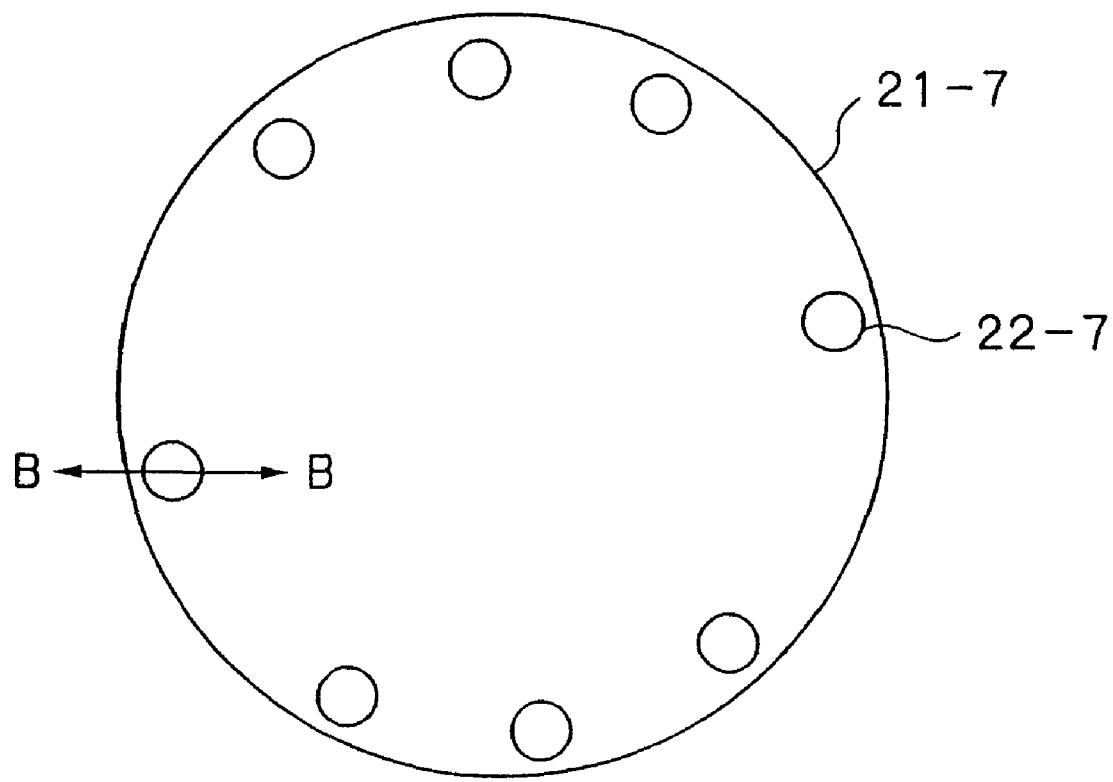
FIG. 42A is a plan view of a cathode tip portion of an electron gun applicable to an electron optical system contained in an electron beam apparatus of the present invention.
Figure 42B:
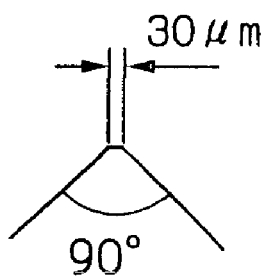
FIG. 42B is a side view of emitters thereof.

FIG. 42A is a plan view of the cathode, and FIG. 42B is a cross-sectional view taken along a line B-B in FIG. 42A. In FIG. 42A, 21-7 designates a column of single crystal Hf (hafnium). The provided column has a crystal orientation of <100> on the end surface, and the surface is machined to leave eight protrusions 22-7 on a circumference of 4 mm diameter, as is the case with FIG. 39. However, in this event, each protrusion 22-7 has a plain portion of approximately 30 μm diameter left on its peak, as illustrated in FIG. 42B, and is in the shape of circular truncated cone having an apical angle of approximately 90°. The plain portion has an end mirror polished before the protrusions are machined, thereby holding the eight plain portions substantially in the same plain shape. Since Hf has a low work function of 3.4 eV, electrons can be emitted at a temperature lower than Ta.

The cathode having the structure illustrated in FIG. 42 is incorporated in the electron gun illustrated in FIG. 41, and the supporting electrode 25-7 is adjusted in the X and Y directions to align the center of each protrusion to the center of a corresponding hole. Also, as described in connection with FIG. 41, the inclination of the cathode is adjusted by the supporting electrode 25-7, and the Wehnelt 26-7 is moved in the optical axis direction for adjustment to match the absolute values of the distances in the optical axis direction.

In the two embodiments of the electron guns described with reference to FIGS. 39 through 42, the cathode is provided with eight protrusions so that eight electron beams can be emitted. However, it goes without saying that an arbitrary number of protrusions can be provided, not limited to eight. Also, the size of the plain surface at the bottom of the protrusion is not limited to the example described above, and may be set to an appropriate size. However, it is preferable to set the diameter to 50 μm or less, or the width in the radial direction to 10 μm or less, and the width in the azimuth direction to 100 μm or less.

In the electron gun described above, when the cathode for emitting multiple beams is formed of single crystal Ta, which facilitates the machining, the cathode is readily manufactured. When the cathode is formed of single crystal Hf, the work function of the cathode can be reduced. Since a single crystal is used, no variations are found in material, so that there is few variations in the intensities of multiple beams.

The materials for the cathode for emitting multiple beams, and the shape of the bottom, so far described, can be applied to a cathode for emitting a single beam.

Figure 43:
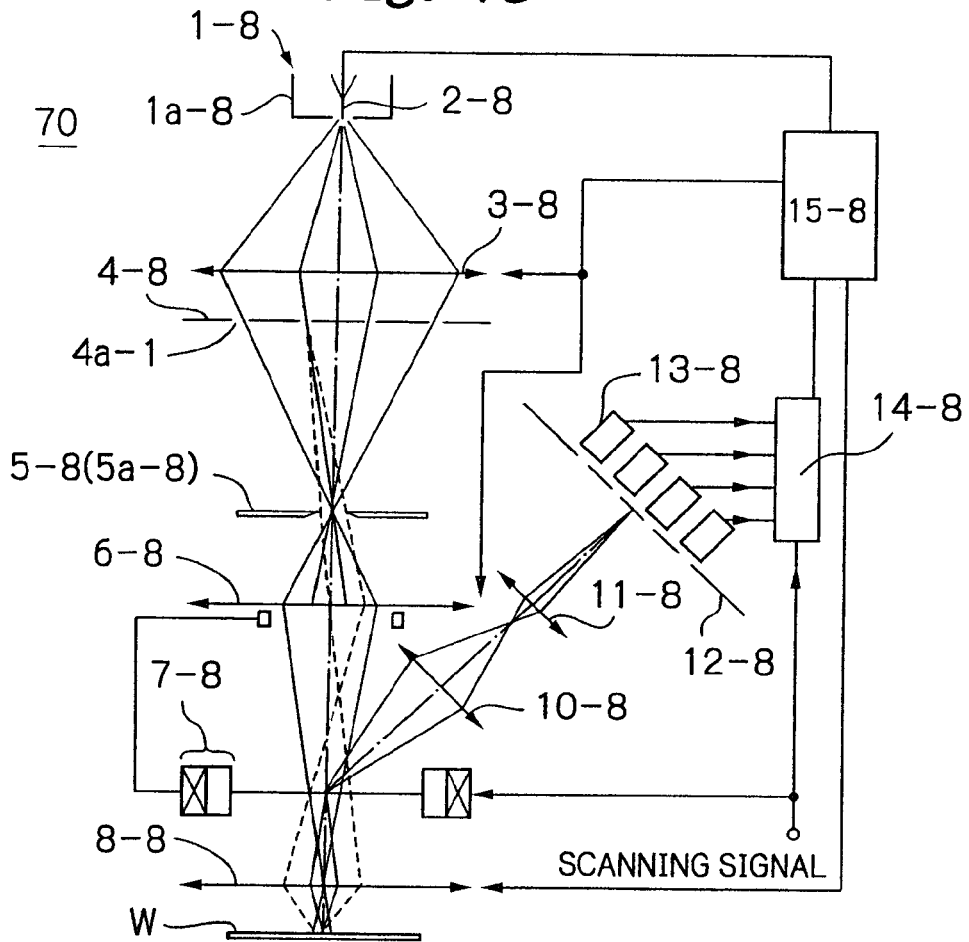
FIG. 43 schematically illustrates another embodiment of an electron beam apparatus of the present invention.

FIG. 43 illustrates another embodiment of the electro-optical system 70 incorporated in the electron beam apparatus according to the present invention, together with a CPU 15-8 which is a control unit therefor. In this embodiment, a Zr-W thermal field emission cathode 2-8 is disposed in a Schottky shield 1a-8 of an electron gun 1-8. This cathode 2-8 has a bottom slightly projected from the Schottky shield 1a-8 to emit an electron beam parallel with the optical axis from the bottom. In the present invention, the cathode 2-8 is projected more downward from the Schottky shield 1a-8 to facilitate the emission of electron beams from four surfaces of <100> in an upper portion of the cathode.

Figure 44:
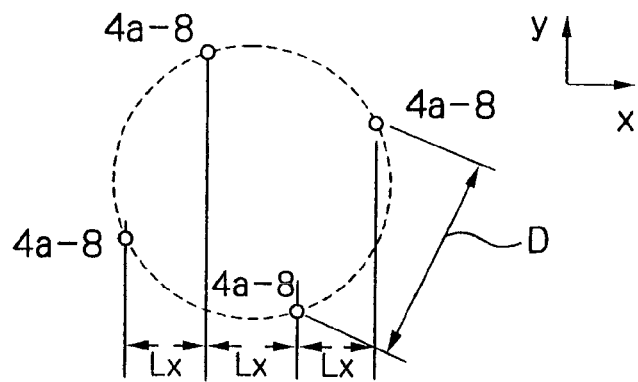
FIG. 44 is a cross section of multi-beam emitted from an electron gun of an electron optical system contained in the electron beam apparatus shown in FIG. 43 on the X-Y plane perpendicular to the optical axis.

The electron beams emitted from the four surfaces in the upper portion of the cathode characteristically is larger (stronger) in luminance than the electron beam emitted from the bottom of the cathode because the surfaces are close to a heating portion. The five electron beams emitted from the four surfaces in the upper portion of the cathode and from the bottom of the cathode are converged by a condenser lens 3-8 to image cross-over on an aperture 5a-8 on an aperture plate 5-8. A first multi-aperture plate 4-8 is placed adjacent to and below the condenser lens 3-8. As illustrated in FIG. 44, the first multi-aperture plate 4-8 has small apertures 4a-8 of 5 μmφ at locations quadrisecting a circumference centered at the optical axis. The small apertures 4a-8 transfer therethrough the four strong electron beams emitted from the four surfaces in the upper portion of the cathode. The first multi-opening plate 4-8 intercepts the electron beam which travels on the optical axis.

As illustrated in FIG. 44, the four small apertures 4a-8 on the first multi-aperture plate 4-8 is set such that distances D between the adjacent small apertures 4a-8 are equal, and when projected in the X direction, three distances Lx between the adjacent small apertures 4a-8 are equal (similar to that in FIG. 9A). The electron beams which have passed the four small apertures 4a-8 are reduced by a reducing lens 6-8 and an objective lens 8-8. In this manner, when a reduction ratio is 1/50, for example, electron beams of 100 nmφ are produced on the surface of a wafer W. When electron beams are spaced at intervals of 100 μm on the surface of the wafer, the distance Lx between the small apertures 4a-8 on the opening plate 4-8 projected in the X direction may be changed to 5 mm.

This reduction ratio of 1/50 can be largely varied by slightly changing the excitation of the reducing lens 6-8 and objective lens 8-8. Secondary electrons generated by the irradiation of the primary electron beams are accelerated by the objective lens 8-8, and enlarged by the enlarging lenses 10-8 and 11-8 and focused on small apertures on a second multi-aperture plate 12-8 for detection.

The secondary electrons traveling near the second multi-aperture plate 12-8 substantially fully pass the small aperture by a convex lens action which is produced by a high voltage applied to a detectors 13-8 and leaking from the small holes, and are detected by the four detectors 13-8 and processed into an image by an image forming unit 14-8. By comparing images of corresponding locations of different chips, defects and the like can be detected.

In the electron beam apparatus illustrated in FIG. 43, in order to prevent the secondary electrons generated by the irradiation of the four primary electrons from cross-talking, the distance D between the adjacent primary electron beams (FIG. 44) may be taken larger than the sum (P+Q) of a blurred beam P converted into a position on the wafer of a secondary optical system and extension Q of back scattered electrons of the primary electron beams. Since the sum (P+Q) varies depending on the energy of the primary electron beams, a large spacing D must be taken between the primary electron beams for entering high energy primary electron beams. For this purpose, the excitation of the reducing lens 6-8 may be adjusted in a direction in which the focal distance becomes longer, by an instruction of the CPU 15-8, to adjust the reduction ratio to approach one. These adjusting parameters are stored in a memory associated with the CPU 15-8, and fetched and used as required for instructions.

The prevention of cross-talk by adjusting the reducing lens can be applied to electro-optical systems in the electron beam apparatus in other embodiments disclosed in the present specifications and their exemplary modifications, not limited to the electron beam apparatus illustrated in FIG. 43.

Figure 45:
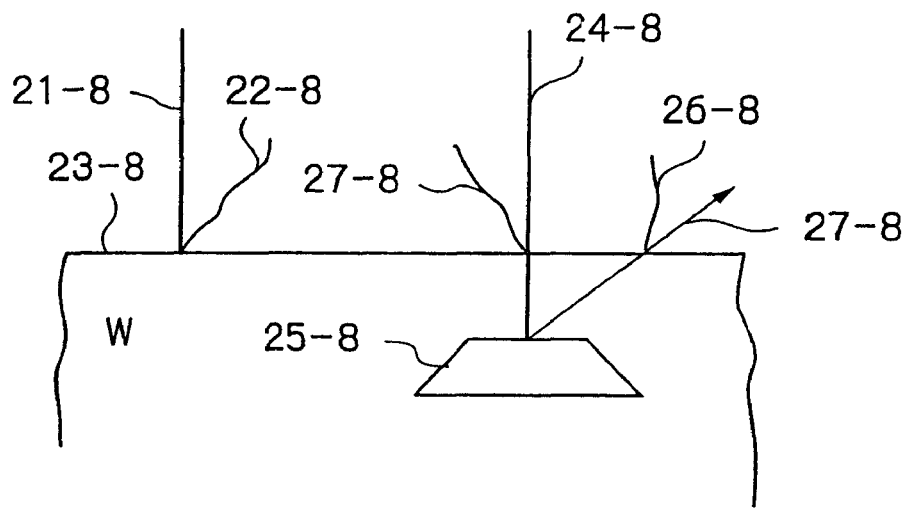
FIG. 45 is an illustration explaining a principle according to which information about a location deeper than the surface of a sample such as a wafer, etc. is obtained.
Figure 46:
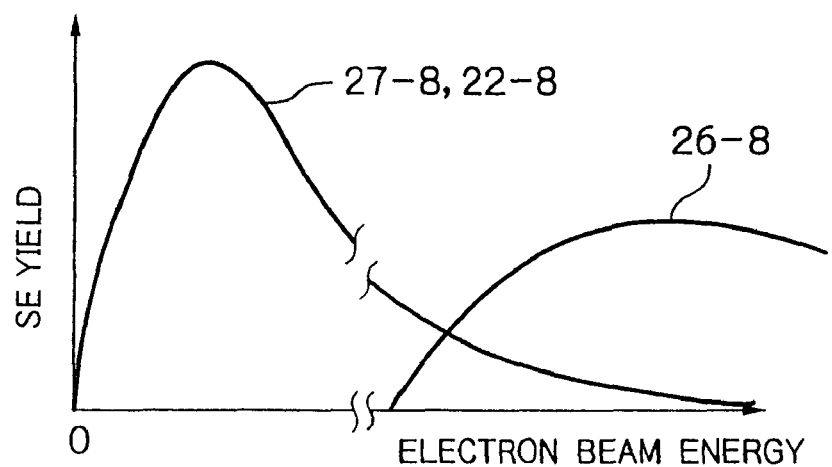
FIG. 46 is a graph representing a relationship between primary electron energy and secondary electron energy generated by the primary electron energy.

FIGS. 45 and 46 are diagrams for explaining the principles of providing information at a location deeper than a surface 23-8 of the wafer W, when image information of the wafer is acquired using the electron beam apparatus according to the present invention. As illustrated in a right-hand region of FIG. 45, when a primary electron beam 24-8 scans a location beneath the surface 23-8 of the wafer W at which a pattern 25-8 of a different material such as tungsten exists, secondary electrons 27-8 are emitted from an incident point on the surface 23-8, and secondary electrons 26-8 are generated when reflected electrons 27-8 of back scattered primary electrons by the pattern 25-8 exit from the surface of the wafer. As illustrated in a left-hand region of FIG. 45, when primary electrons 21-8 scan a location beneath the surface 23-8 at which no pattern exists, secondary electrons 22-8 are emitted from the surface 23-8.

FIG. 46 is a graph showing the amount of generated secondary electrons on the vertical axis, with the horizontal axis representing the energy of the primary electrons. The secondary electrons 22-8 or 27-8 exhibit an intensity distribution which has a peak value in a left-hand portion of the graph in FIG. 46, while the secondary electrons 26-8 exhibit an intensity distribution which has a peak value in a right-hand portion. Therefore, when the secondary electrons 22-8, 27-8 are removed as offsets, the secondary electrons 26-8, i.e., information on layers beneath the surface of the wafer W can only be acquired.

Since the secondary electrons 26-8 emitted from a deep location of the wafer are not generated unless the primary electron beam has a certain level of energy, the energy of the primary electron beam must be increased to approximately 100 kV or higher. The energy of approximately 100 kV is such that the energy still remains when the primary electron beam returns after it has been reflected by a pattern deep beneath the wafer. For acquiring pattern information at a location not deep, the energy of the primary electron beam may be lower. Also, for evaluating the surface of the wafer, approximately 0.5 keV is suitable. In other words, the energy of the primary electrons may be changed as appropriate in a range of 0.5 keV to 100 keV depending on the depth from the surface.

The electron beam apparatus described with reference to FIGS. 43 through 46 can realize a high throughput, and set the energy of the primary electron beams in accordance with particular purposes, so that damages on a sample or a wafer can be minimized.

In a multi-beam based electro-optical system of a conventional electron beam apparatus, multiple beams are incident from an oblique direction to a wafer W, so that a beam spot generated by each beam results in the shape of ellipse which is longer in the beam incident direction, i.e., in a direction in which the beam is projected onto the wafer, thereby giving rise to a problem that a longitudinal resolution is degraded. Also, in an electron beam apparatus which continuously moves a stage, variations in speed are inevitable even if the stage is moved at a constant speed. Since variations in the speed of the stage result in a failure in acquiring pixel data appropriately corresponding to positions on the surface of the wafer, no appropriate evaluations can be achieved. Further, the stage normally includes parts made of metals and the like, and as such a stage is moved, eddy currents are generated in the metal parts by interactions with a magnetic field created by a deflector of the electro-optical system. Since the eddy currents generate magnetic fields, a problem arises in that such magnetic fields change a direction in which electron beams are deflected.

Figure 47:
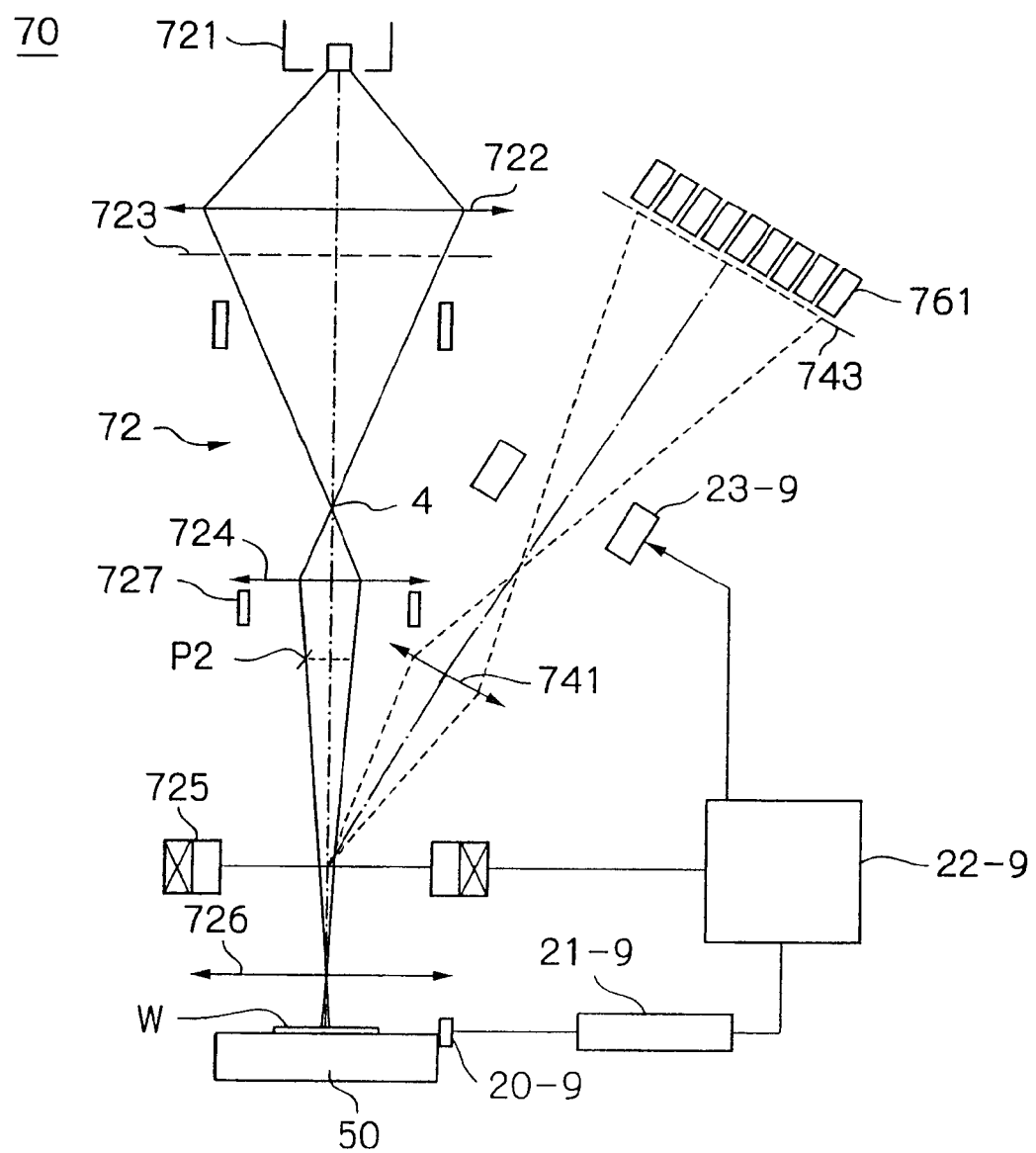
FIG. 47 schematically illustrates another embodiment of an electron beam apparatus of the present invention.

FIG. 47 illustrates an embodiment of the electron beam apparatus according to the present invention which can solve the just before mentioned problems of the prior art example. This embodiment adds a laser mirror 20-9, a laser interferometer system 21-9, a deflection amount correcting circuit 22-9, and a secondary electron deflector 23-9 to the electro-optical system 70 in the electron beam apparatus illustrated in FIG. 8, and removes the enlarging lens 742 in the secondary optical system. Therefore, description on components and operations identical to those of the electron beam apparatus in FIG. 8 is omitted, and operations related to the newly added components will be described.

In FIG. 47, as a Y-table of a stage apparatus 50, on which a wafer W is carried, is continuously moved in the Y direction, the moving speed and current position are detected by the laser mirror 20-9 and the laser interferometer 21-9. While a majority of the stage apparatus 50 is formed of insulating materials such as ceramics, metal materials are used for metal parts such as bearings and coatings on surfaces.

On the other hand, an E×B deflector 725 including an electromagnetic deflector generates a relatively large static magnetic field. Since this static magnetic field extends over the stage apparatus 50, an eddy current is generated when the Y-table is moved at a high speed. Then, a magnetic field is generated by the eddy current, and as a result, primary electron beams and secondary electron beams are undesirably deflected. If the primary electron beams are undesirably deflected, the primary electron beams are irradiated to a location deviated from an intended location. On the other hand, if the secondary electron beams are undesirably deflected, the secondary electron beams cannot be efficiently passed through small apertures of a second multi-aperture plate 743 or are introduced into adjacent openings.

For correcting the deflection of the primary electron beams and secondary electron beams due to the magnetic field generated by the eddy current, the relationship between the stage moving speed and the respective amounts of deflection for the primary electron beams and secondary electron beams has been previously measured through a test in actual use, and the relationship between them has been previously stored in a corrective deflection amount table in the deflection amount correcting circuit 22-9. The deflection amount correcting circuit 22-9 is provided as a part of a control unit 2 (FIG. 1), and searches the corrective deflection amount table for the amounts of deflection to be corrected for the primary electron beams and secondary electron beams based on the moving speed of the Y-table measured by the laser interferometer 21-9, and controls the electrostatic deflectors 725 and 23-9 corresponding thereto to correct the amounts of deflection for the primary electron beams and secondary electron beams. In this manner, since the primary electron beams and secondary electron beams are provided with essential amounts of deflection, they can reach positions intended thereby for irradiation and detection.

Also, when the deflection amount correcting circuit 22-9 detects variations in the stage speed while the Y-table of the stage apparatus 50 is being moved to create image data, the circuit converts that into positional fluctuations and corrects the positional fluctuations. The positional fluctuations are calculated by integrating the variations in speed over time. Also, the positional fluctuations are corrected by inverting the sign of a voltage calculated by dividing the amount of positional fluctuations by a deflection sensitivity and supplying the inverted voltage to electrostatic deflectors (in the E×B deflector 725, and deflector 727) in the primary optical system and the electrostatic deflector 23-9.

Since the electrostatic deflector for correcting the amount of deflection for the primary electron beams is positioned behind the reducing lens 724, a light path to the reducing lens 724 will not be changed even if the amount of deflection is changed, so that the intensity of the primary electron beams will not be changed by the correction. Similarly, since the electrostatic deflector 23-9 for correcting the amount of deflection for the secondary electron beams is positioned behind an enlarging lens 741 in the secondary optical system, blurred secondary electron beams will not be exacerbated even if the correction is made.

The electron beam apparatus illustrated in FIG. 47 can correct undesired deflection for the first and second electron beams caused by the eddy current associated with the movement of the stage, and therefore acquire image data corresponding to appropriate positions of a sample. Also, a correction can be made even if the stage speed varies. Further, the generation of cross-talk can be reduced, even if multiple beams are used, by setting the distance between the adjacent primary electron beams irradiated onto a sample to be larger than the resolution of the secondary optical system.

Figure 48:
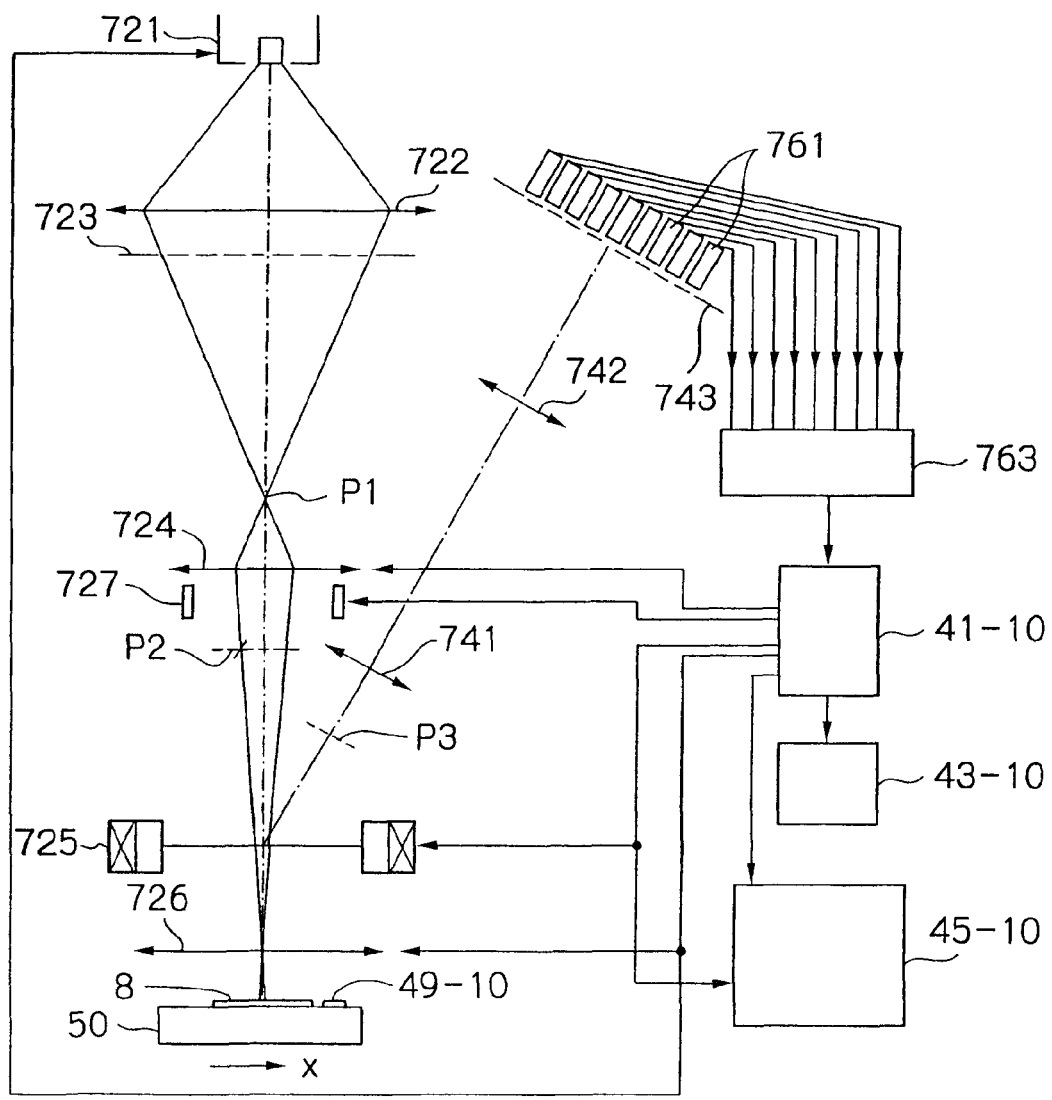
FIG. 48 schematically illustrates still another embodiment of an electron beam apparatus of the present invention.

FIG. 48 illustrates another embodiment of the electron beam apparatus according to the present invention. This embodiment adds a device for adjusting a beam diameter using a standard mark 49-10 to the electro-optical system 70 illustrated in FIG. 8. Therefore, detailed description on components and operations identical to those of the electron beam apparatus in FIG. 8 is omitted.

Specifically, the conventional electron beam apparatus is disadvantageous in requirements of a long time for a test due to an excessively small pixel size depending on objects under testing, and a failure in providing a sufficient resolution due to an excessively large pixel size, on the contrary, since the pixel dimension is not changed even if a fine pattern is tested, a coarse pattern is tested, or a pattern dimension of an object under testing varies. Further, for enlarging a beam diameter, the conventional electron beam apparatus intentionally blurs a beam to enlarge the beam diameter, without utilizing at all the advantage that a beam current is increased as the beam diameter is enlarged, so that the conventional electron beam apparatus is disadvantageous in that the S/N ratio is largely lost when the beam diameter is enlarged. The electron beam apparatus illustrated in FIG. 48 can solve these problems.

In the electron beam apparatus illustrated in FIG. 48, a signal detected in a detector 761 is processed in an image processing unit 763, and stored in an image storage device 43-10 under control of a CPU 41-10 in a control unit 2 (FIG. 1). Then, the detected signal is displayed on a monitor 45-10, and compared with a standard pattern or image data of the same die on a different wafer to perform evaluations such as detection of defects.

As previously described in connection with the electro-optical system 70 in the electron beam apparatus illustrated in FIG. 8, when primary electron beams passing through the respective apertures of the first multi-aperture plate 723 are focused on the surface of a wafer W, and secondary electron beams emitted from the wafer are focused on the detectors 761, it is necessary to pay particular attention to minimize the influence of distortion and field curvature produced in the primary optical system and secondary optical system. Also, as described above, in regard to the relationship between the distances between the adjacent primary electron beams and the secondary optical system, cross-talk between a plurality of beams can be eliminated by spacing the primary electron beams by a distance larger than the aberration of the secondary optical system.

Figures 49A, 49B:
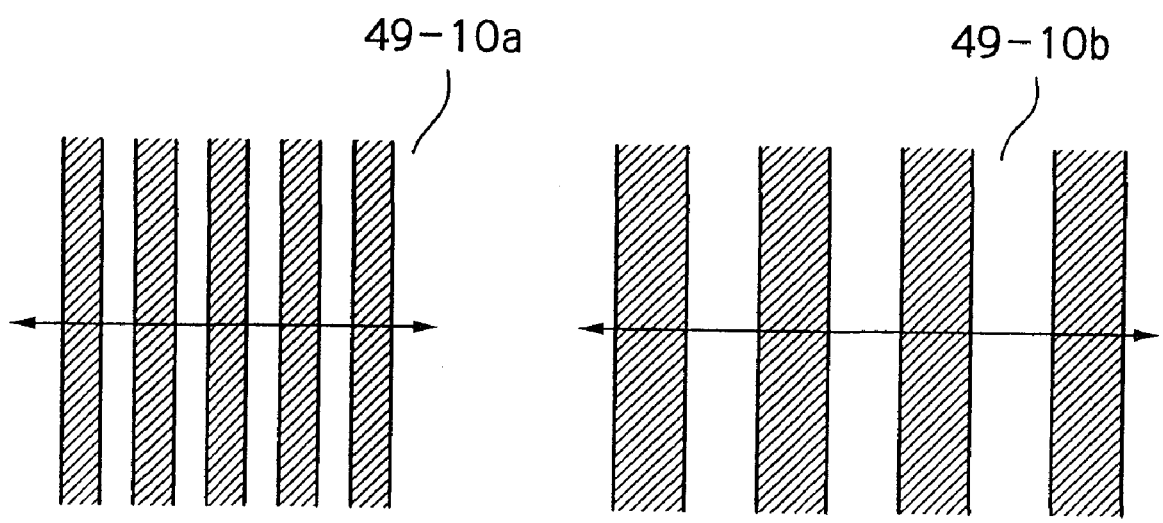
FIG. 49 shows a layout of standard marks mounted on an X-Y stage of the electron beam apparatus shown in FIG. 48.

FIG. 49 illustrates layouts of standard marks 49-10 of a plurality of pattern sizes mounted on the stage apparatus 50. In the figure, 49-10a shows an L&S pattern (line and space pattern) of 0.05 μm, while 49-10b shows an L&S pattern of 0.1 μm. In this manner, several kinds of standard marks corresponding to line widths of patterns under evaluation have been provided on an X-Y stage. FIG. 49 shows only two kinds of representative standard marks.

Before conducting a test or the like, the X-Y stage of the stage apparatus 50 is moved to select a standard mark 49-10 which matches the size of a pattern under detection on a wafer W and aligns the selected standard mark to the optical axis of the primary optical system, and the beam diameter is changed in the following approach to select an optimal beam diameter or a beam current suitable for the dimension of the pattern under detection.

In other words, the beam diameter can be changed by changing the brightness of a beam from an electron gun by changing a bias voltage applied to a Wehnelt of an electron gun 721. As a smaller bias is applied to the Wehnelt, a current of the electron gun is increased to enhance the brightness, resulting in a larger current of the multiple beams. As the beam current of the multiple beams is increased, the beam diameter becomes larger due to a space charge effect.

Also, as another method of changing the beam diameter, a reducing lens 724 and an objective lens 726 are acted as a zoom lens to change the beam dimension. In this case, since the reduction ratio is also adjusted in a direction in which it approaches one to increase the beam current, the beam diameter becomes larger as well. However, in this case, the spacing between beams in the multiple beams also changes in the same proportion, the method of changing the bias applied to the Wehnelt may be employed if the spacing between the beams is not to be changed.

FIG. 50 shows waveforms of signals detected by a detector which is observed by the monitor 45-10 when the standard marks 49-10a, 45-10b are scanned by the multiple beams. FIGS. 50a-1-50a-3 show signals when the standard mark 49-10a is scanned with a variously changed beam dimension, and FIGS. 50b-1-50b-3 show signals when the standard mark 49-10b is scanned with a variously changed beam dimension.

FIGS. 50a-1 shows a signal when the beam diameter is enlarged more than the line width, in which case a beam having a dimension larger than the line width is used for scanning, in spite of a large beam current, so that the contrast S of the signal is not so large, and noise N exhibits a large value due to the large beam current. The S/N ratio is approximately 3.4.

FIGS. 50a-3 shows a signal when the beam diameter is extremely small, in which case although a faithful waveform (near a square wave) is generated, the contrast S of the signal is not large due to the small beam current. Also, the noise N is small corresponding to the beam current which is small, and the S/N ratio is approximately 6.25.

FIGS. 50a-2 shows a signal when the beam diameter is suitable, in which case a blurred beam exhibits an adequate value, the beam current is relatively large, the signal has large contrast S, and the S/N ratio is approximately 12.3.

Whether to select FIG. 50a-2 or 50a-3 may be based on which has a larger (contrast/noise) ratio. In the illustrated example, the beam diameter which results in the pattern shown in FIG. 50a-2 may be selected for the mark 49-10a.

For the mark 49-10b, a similar calibration is made to select a beam dimension or a beam diameter suitable to this line width. In the shown example, the beam diameter which results in the pattern of FIG. 50b-2 may be selected.

In this manner, a beam diameter or a beam current may be selected in accordance with a pattern dimension under estimation such that the S/N ratio of a secondary electron signal detected by the detector is maximized. More specifically, regular standard patterns having different pitches are placed on the X-Y stage. A device is provided for storing signal waveforms generated when the regular standard patterns are scanned. A device for calculating the amplitudes (S) of the signals from the signal waveforms, a device for calculating the amplitude (N) of noise, and a device for calculating the S/N ratio are provided. A plural kinds of beam diameters are set, and a regular pattern having a pitch twice the thinnest line width of a pattern under evaluation is scanned by these beam diameters, and the S/N ratios are calculated to select the beam diameter which exhibits the highest S/N ratio, thereby making it possible to evaluate a high S/N ratio for all patterns under evaluation.

Alternatively, as the regular standard patterns, standard patterns may be found on a wafer under testing for use, instead of those on the X-Y stage, to examine the (signal/noise) ratio for the found patterns in a similar manner. The method according to the present invention does not necessarily require the multiple beams, but can be applied to an evaluation of a pattern when a single beam is used for scanning.

The electron beam apparatus described with reference to FIGS. 48 through 50 can ensure a required S/N ratio even at a higher scanning speed, and also ensure a high S/N ratio even without an averaging process. Also, since the beam diameter or beam current can be selected in accordance with a pattern under evaluation to maximize the S/N ratio, a high throughput can be realized at a high resolution irrespective of the size of a pattern under evaluation.

Figure 51:
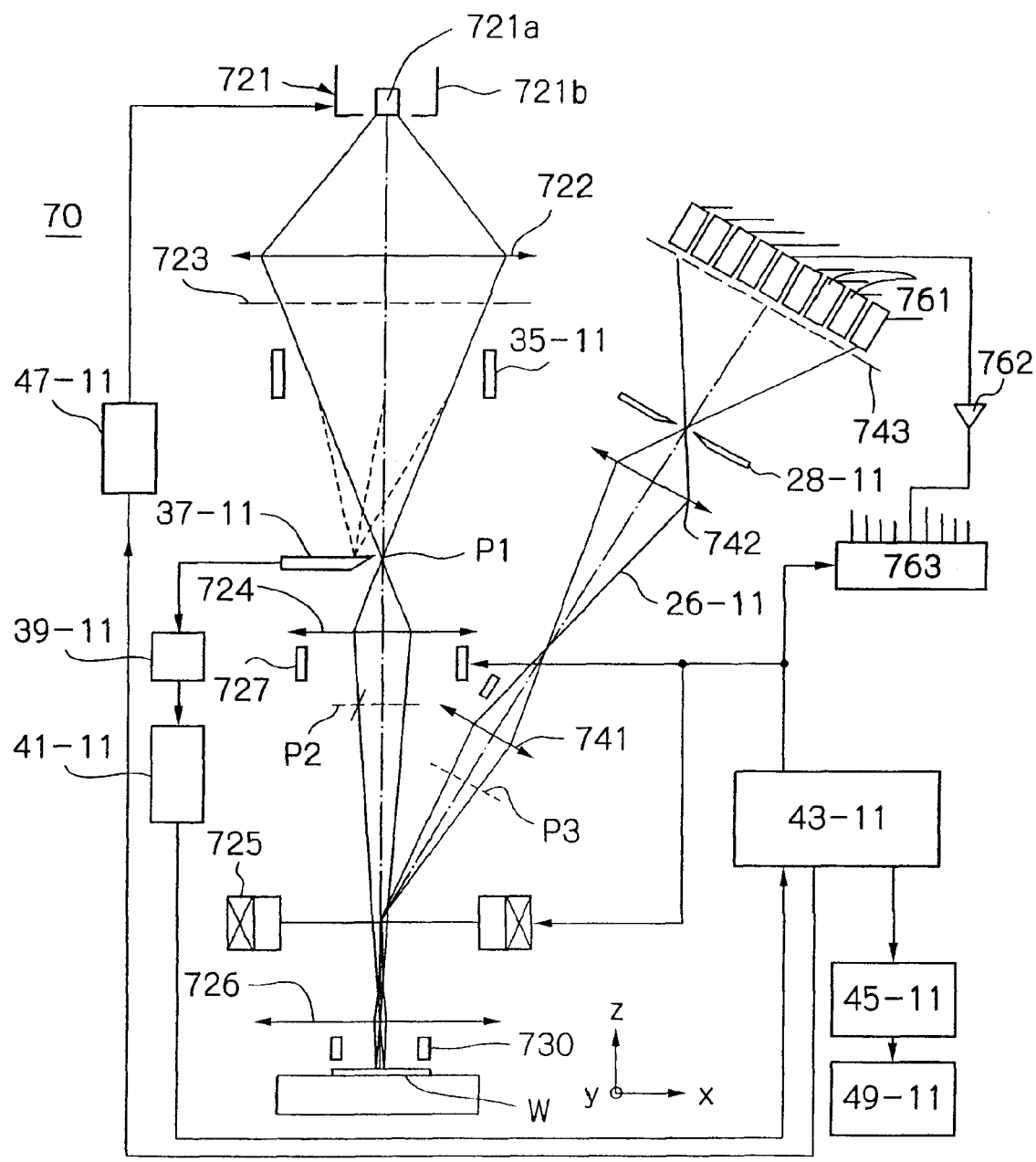
FIG. 51 schematically illustrates further another embodiment of an electron beam apparatus of the present invention.

FIG. 51 illustrates a further embodiment of the electron beam apparatus according to the present invention. This electron beam apparatus employs the electro-optical system in the embodiment illustrated in FIG. 8, and adds a device for preventing excessive irradiation of electron beams. Therefore, description on components and operations identical to those of the electron beam apparatus in the embodiment of FIG. 8 is omitted, and operations related to the newly added components will be described.

In FIG. 51, 26-11 designates trajectories of two secondary electrons positioned on a diameter, out of secondary electrons emitted from points on a circumference irradiated with primary electron beams, which are emitted onto the surface of the wafer W in the vertical direction. An iris 28-11 is provided at a position at which these trajectories intersect the optical axis such that the aberration becomes smaller than a minimum value of beam spacings or distances of the primary electron beams, as converted on the surface of the wafer. Also, in FIG. 51, 730 designates an axially symmetric electrode for measuring a potential of a pattern on the wafer W.

How to control the amount of irradiated primary electron beams will be described. Multiple beams are deflected by a deflector 35-11 at fly-back of scanning, the beams are blocked by a knife edge 37-11 for blanking, a current absorbed by the knife edge is measured by a current meter 39-11, and the amount of irradiation per unit area is calculated by an irradiation amount calculating circuit 41-11. This value is stored in a storage device 45-11 through a CPU 43-11. The irradiation amount calculating circuit 41-11, CPU 43-11, and storage device 45-11 are included in a control unit 2 (FIG. 1).

Further, when the resulting amount of irradiation per unit area increases to a predetermined value, for example, 2 $\mu c/cm^2$ or more, an electron gun control power supply 47-11 is controlled by an instruction from the CPU 43-11 to reduce a voltage applied to a Wehnelt electrode 721b, thereby reducing a beam current and the amount of irradiation. Also, if the amount of irradiation per unit area exceeds, for example, 3 $\mu c/cm^2$ due to a delay in control, irradiation amount data related to the pertinent irradiated region is only output from an output device 49-11, while the evaluation is continued. In this event, the entire surface of the wafer is displayed on a CRT, and a region irradiated with an excessive amount of irradiation is colored, as illustrated in an upper region of FIG. 52, to display for the operator. Further, when the amount of irradiation per unit area exceeds a larger value, for example, 5 $\mu c/cm^2$, the evaluation is once stopped.

Figure 52:
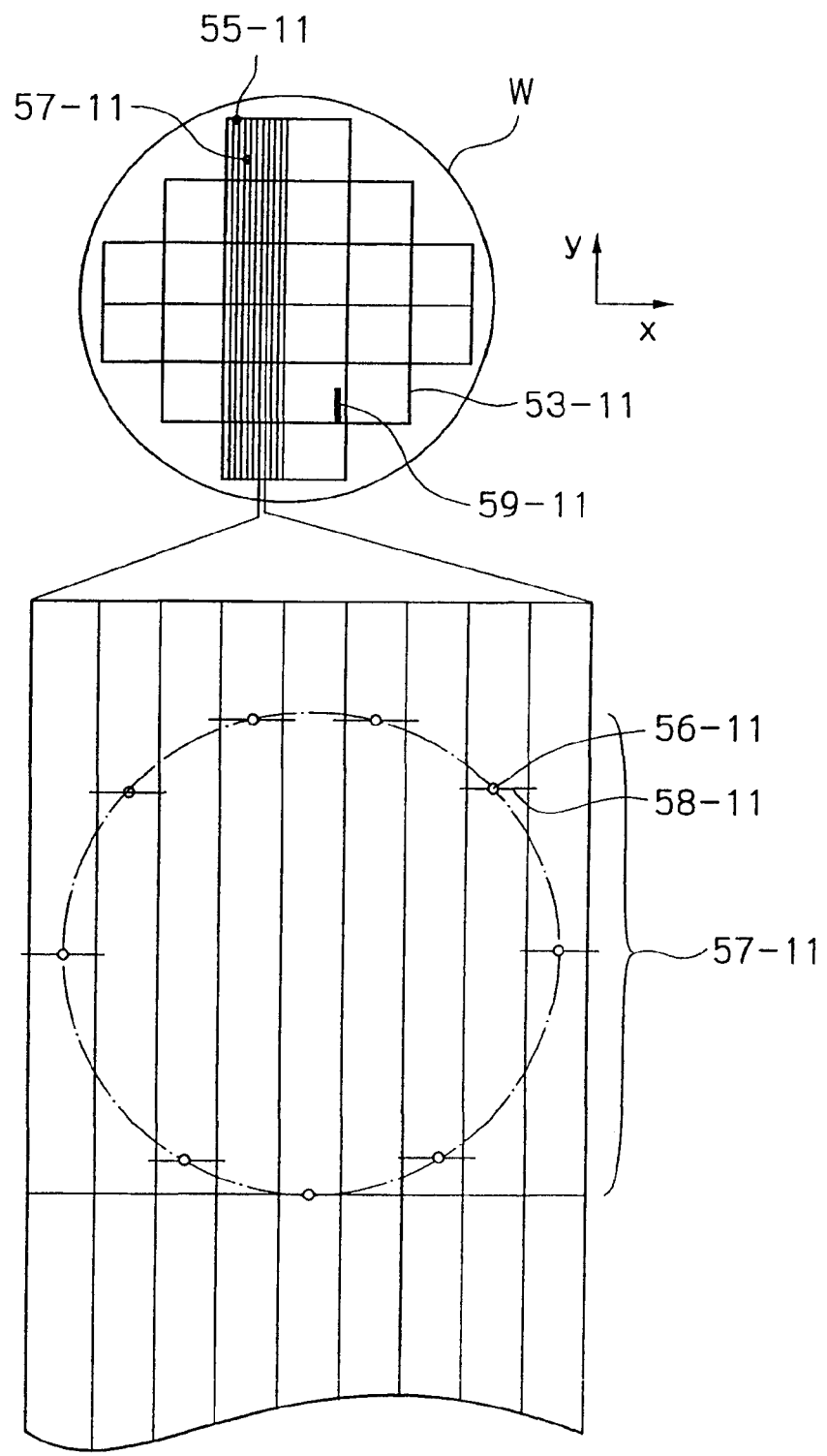
FIG. 52 is an illustration explaining measurement of an amount of radiation by an electron beam apparatus of the present invention.

FIG. 52 is a diagram for explaining how to measure the amount of irradiation to the wafer W. The wafer W is divided into a large number of chips 53-11, each of which is divided into regions 55-11, called a stripe, in parallel with a direction in which the stage is continuously moved (in the Y direction in the illustrated example). Image data is acquired as the stage is moved in stripe widths. An enlarged view of the stripe is shown in a lower region of FIG. 52. Within a stripe 55-11, nine multiple beams 56-11 formed in the primary optical system are arranged in the X direction, for example, at equal intervals of 100 μm. These beams are scanned in the X direction over a width of 102 μm (a range indicated by 58-11 in the figure). A width of 1 μm on each side of 100 μm range is a scanned region which overlap with an adjacent beam or an adjacent stripe.

Viewed at a certain time during acquisition of image data, all of the nine multiple beams 56-11 fall under a region of 900 μm×900 μm square indicated by 57-11. This region is defined as a unit area. If a beam current per unit area becomes abnormally large during acquisition of image data, the output device 49-11 outputs how many times the beam current per unit area of 900 μm×900 μm indicated by 57-11 has increased more than a normal magnitude.

As described above, the beam current is measured by measuring a current absorbed by the knife edge 37-11 in fly-back of scanning. This measurement involves repetitions of periodic image data acquisition and current measurement in such a manner that, for example, after image data is acquired by scanning the beam for 10 μs, the current is measured for 1 μs, and after image data is again acquired for 10 μs, the current is measured for 1 μs. Then, only when the measured current exceeds a predetermined value, this measurement is output as an abnormal current. For example, in FIG. 52, if the beam current exceeds a defined value during acquisition of image data for a solid black region of a chip indicated by 59-11, this region is colored for display on a monitor.

The defined value for the beam current can be determined based on experiment data on the amount of irradiation and breakdown of a gate oxide film, and as a value multiplexed by a sufficiently safety coefficient in an actual integrated circuit or TEG (Test Element Group).

Also, when the beam current per unit area begins to increase from a normal value which is set lower than the defined value, a voltage applied to the Wehnelt electrode 721b of the electron gun in FIG. 51 is increased to reduce an electron gun current to reduce the beam current.

The electron beam apparatus according to this embodiment can adjust a focusing condition and an enlargement ratio of the secondary optical system independently of a lens condition in the primary optical system. Also, since an upper limit is determined for the amount of irradiation to a sample per unit area, the performance and reliability of the sample will not be affected. Furthermore, the beam current can be adjusted with a simple manipulation.

Figure 53:
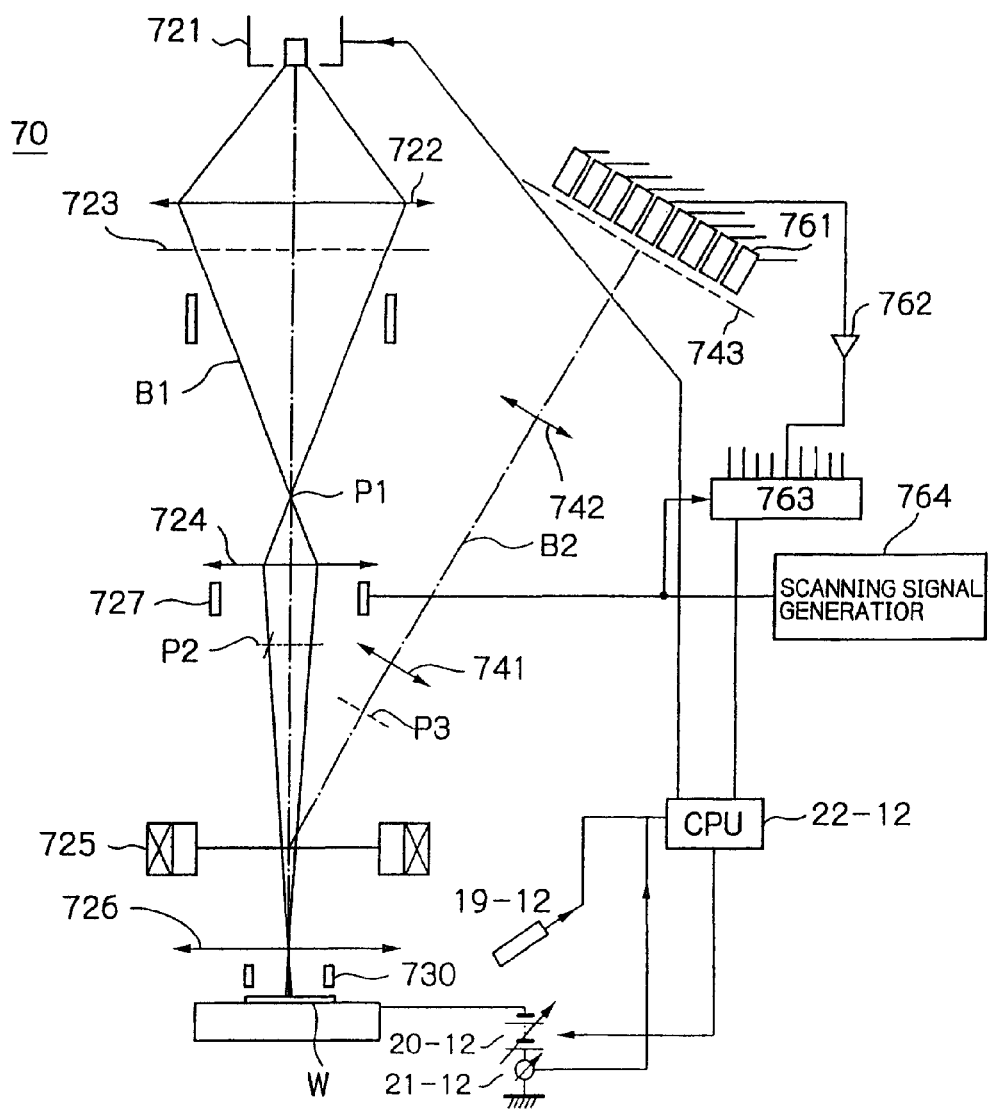
FIG. 53 schematically illustrates still another embodiment of an electron beam apparatus of the present invention.

FIG. 53 illustrates another embodiment of the electron beam apparatus according to the present invention. This electron beam apparatus adds a device for applying a decelerating electric field between an objective lens and a wafer, and a device for preventing a discharge of the wafer to the electron beam apparatus illustrated in FIG. 8. Therefore, description on components and operations identical to those of the electron beam apparatus in FIG. 8 is omitted, and operations related to the newly added components will be described in detail.

It is generally known that a secondary electron detection efficiency is increased by utilizing reduced chromatic and spherical aberrations of primary electron beams by applying a decelerating electric field between an objective lens and a wafer, and accelerating secondary electrons. However, if the sample is a wafer containing vias, attention should be paid. Specifically, when a large decelerating electric field is applied between the objective lens and wafer, and a predetermined value or more of primary electron beams are passed, this will end up on a discharge occurring between a via and the objective lens, possibly damaging device patterns formed on the wafer. There are wafers more susceptible and less susceptible to such a discharge, and the respective wafers are different in the condition under which a discharge occurs (the value of decelerating electric field voltage, and the amount of primary beam current).

In the electro-optical system 70 in the electron beam apparatus illustrated in FIG. 53, an objective lens 726 is implemented as an electrostatic lens, and a positive high voltage is applied to either of electrodes of the lens. On the other hand, the wafer W is applied with a negative high voltage by a voltage source 20-12. In this manner, a decelerating electric field is formed between the objective lens 726 and wafer W.

When the wafer W is formed with vias, primary electron beams incident into a via causes a large amount of secondary electrons to be emitted therefrom since the vias are made of a metal having a high atomic number such as tungsten. Also, there are sharp metal patterns of sub-micron diameters located near vias, so that a larger electric field is locally generated by the decelerating electric field. For these reasons, the wafer formed with vias is quite susceptible to a discharge.

However, a discharge does not immediately occur even if such a condition is fully established. First, a corona discharge occurs, wherein a residual gas locally illuminates in a region in which a large electric field exists, and a transient state called a spark discharge next appears, followed by a transition to an ark discharge. In the present specifications, a period from the corona discharge to the outset of the spark discharge is called "a discharge leader phenomenon". It has been found that an arc discharge can be avoided to prevent the wafer from being broken by reducing the beam current to reduce the primary electron beams to a fixed amount or less, or reducing the decelerating electric field voltage between the objective lens 726 and wafer W, or taking both of these actions at the time of this discharge leader phenomenon.

Also, since wafers more susceptible to a discharge and wafers less susceptible to a discharge differ in the decelerating electric field voltage and the amount of primary electron beams with which a discharge occurs, it is desirable to know limit values for preventing a discharge for each wafer without fixing these values at low levels.

The electron beam apparatus illustrated in FIG. 53 comprises a photo-multiplier tube (PMT) 19-12 and a wafer current meter 21-12 as a detector for detecting a discharge between the wafer W and objective lens 726 or the discharge leading phenomenon to generate a signal. The PMT 19-12 can detect light emission due to a corona discharge and an arc discharge, and the wafer current meter 21-12 can detect an abnormal current at the outset of a corona discharge and an ark discharge.

When the PMT 19-12 detects light emission due to a corona discharge or the wafer current meter 21-12 detects an abnormal current at the time of the discharge leader phenomenon, the information is input to a CPU 22-12 in a control unit 2 (FIG. 1). A voltage of decelerating electric field and a beam current value (corresponding to the amount of primary electron beams) of the electron gun 1 serve as basic data for determining the condition for preventing a discharge. The CPU 22-12, in response to the input indicative of the light emission or abnormal current, or both, conducts a control, i.e., reduces the voltage 20-12 of decelerating electric field, or sends a feedback signal to an electron gun 721 to reduce the beam current to reduce the primary electron beams to a fixed amount or less so as to prevent a discharge. The CPU 22-21 may conduct both of these controls.

While both of the PMT 19-12 and wafer current meter 21-12 are preferably used, one of them may be omitted.

Figure 54:
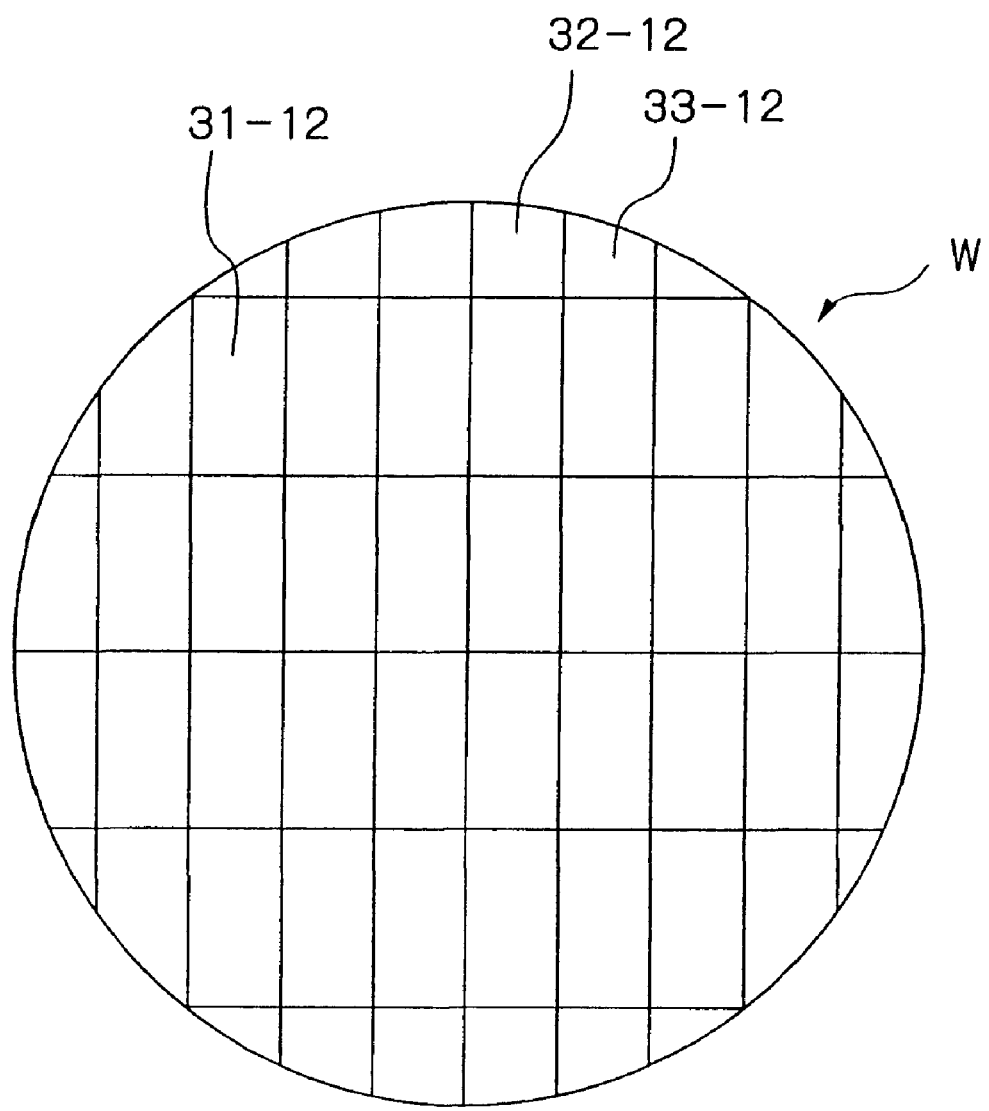
FIG. 54 is a plan view showing an arrangement of devices on a single wafer.

FIG. 54 shows the arrangement of devices on a single wafer W. While a plurality of rectangular chips 31-12 are taken from the circular wafer W, fragmentary chips, which are less than complete chips, exist in peripheral regions, as indicated by reference numerals 32-12, 33-12. These fragmentary chip regions are also subjected to normal lithography and a variety of processes in a manner similar to the region of the complete chips 31-12. On the other hand, since these fragmentary chips are not used as products, these regions may be broken without any problem. Therefore, when the regions of these fragmentary chips 32-12, 33-12 are used to not only detect the discharge leader phenomenon but also detect a discharge phenomenon without fear for breakdown, more correct determination can be made as to the condition for preventing a discharge. In this event, the PMT 19-12 detects light emission due to an arc discharge, while the wafer current meter 21-12 detects an abnormal current at the time of the arc discharge to send a signal to the CPU 22-12. In this manner, the CPU 22-12 can correctly indicate a voltage value for the decelerating electric field and the beam current value (corresponding to the amount of primary electron beams) as limit values at which no discharge occurs.

Since the electron beam apparatus described with reference to FIGS. 53 and 54 can set the limit condition for preventing a discharge in accordance with the discharge characteristics of a sample, the sample can be prevented from a failure.

Figure 55:
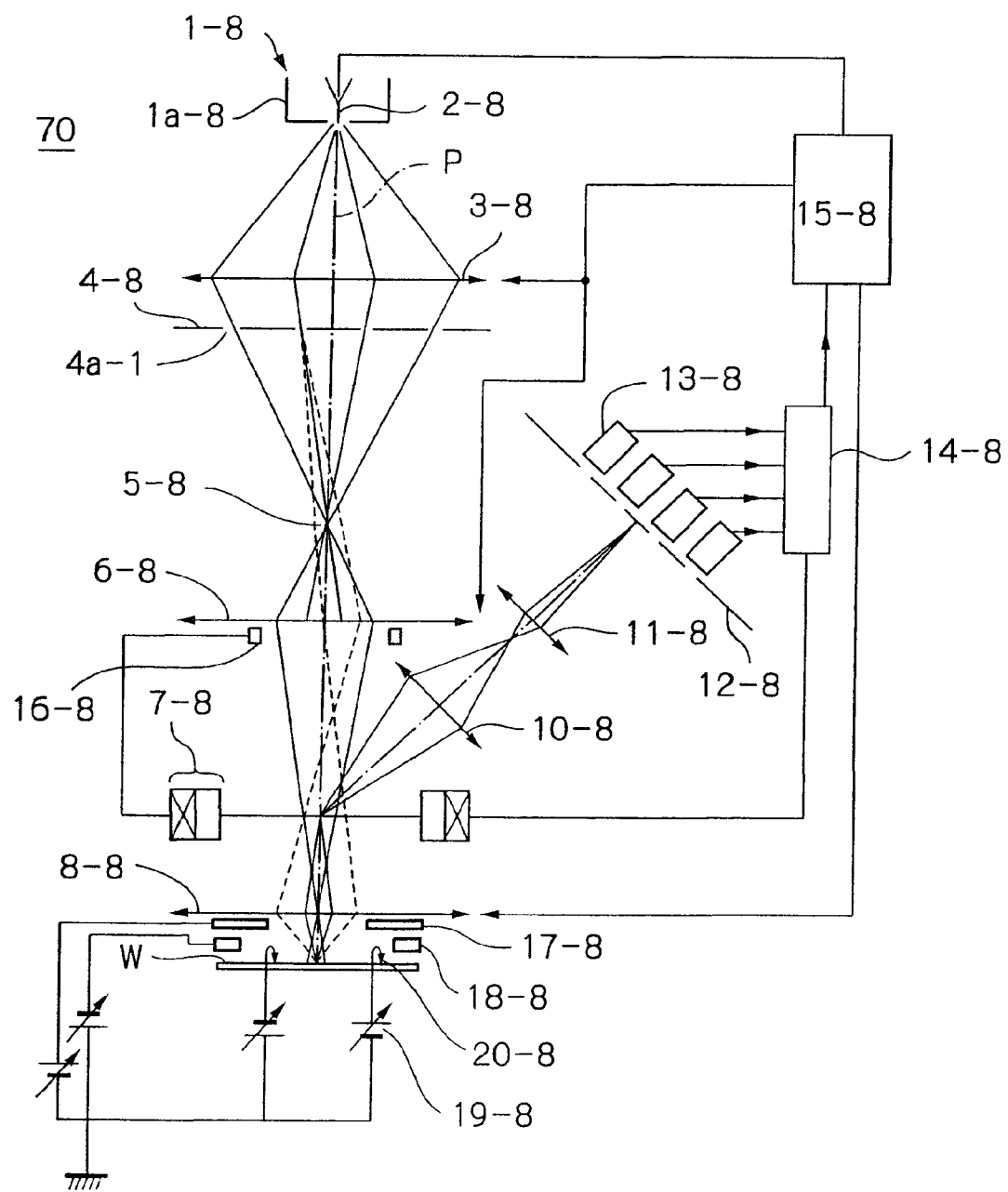
FIG. 55 schematically illustrates still another embodiment of an electron beam apparatus of the present invention.

FIG. 55 illustrates a further embodiment of the electron beam apparatus according to the present invention. In this embodiment, an energy filter device is added to the electron beam apparatus illustrated in FIG. 43. Therefore, description on components and operations identical to those of the electron beam apparatus in FIG. 43 is omitted, and operations related to the newly added components will be described in detail.

In the electro-optical system 70 in the electron beam apparatus illustrated in FIG. 55, electron beams emitted from four locations on the surface of a wafer W irradiated with four primary electron beams are drawn by a positive voltage applied to one electrode 17-8 which forms part of an objective lens 8-8. The wafer W is applied with a lower voltage by an electrode 18-1, which is axially symmetrically disposed on the near side of the electrode 17-8 from the wafer W, to filter the drawn secondary electron beams. Specifically, it is determined whether the secondary electron beams pass the objective lens, or is returned to the wafer W, depending on whether they can pass over a potential barrier on the axis created by the electrode 18-8 which acts as an energy filter.

Out of the secondary electrons emitted from the surface of the wafer W, those emitted from a pattern having a low voltage pass the barrier created by the electrode 18-8, whereas those emitted from a pattern having a high voltage cannot pass the electrode 18-8. From this difference, it is possible to measure a potential of a pattern on the wafer irradiated with the primary electron beams.

Alternatively, instead of applying a charge by irradiation of electron beams, the wafer W may be applied with a predetermined voltage by a power supply 19-8 through a connector 20-8 to measure a voltage or a current of a circuit pattern on the wafer W, thereby determining disconnection and short-circuit of the circuit pattern. In this event, since a time for applying a charge can be saved, a high throughput can be provided.

Since the electron beam apparatus illustrated in FIG. 55 can select whether a potential is applied to a wiring pattern on a sample or wafer from a connector or from electron beams, an increased degree of freedom can be attained for measurements. Also, since the energy filter (i.e., the electrode 18-8) is an axially symmetric electrode and has a large hole near the optical axis, distortion and aberration of blur will not occur, which would otherwise be experienced when a mesh electrode was used, when the primary electron beams are scanned.

Figure 56:
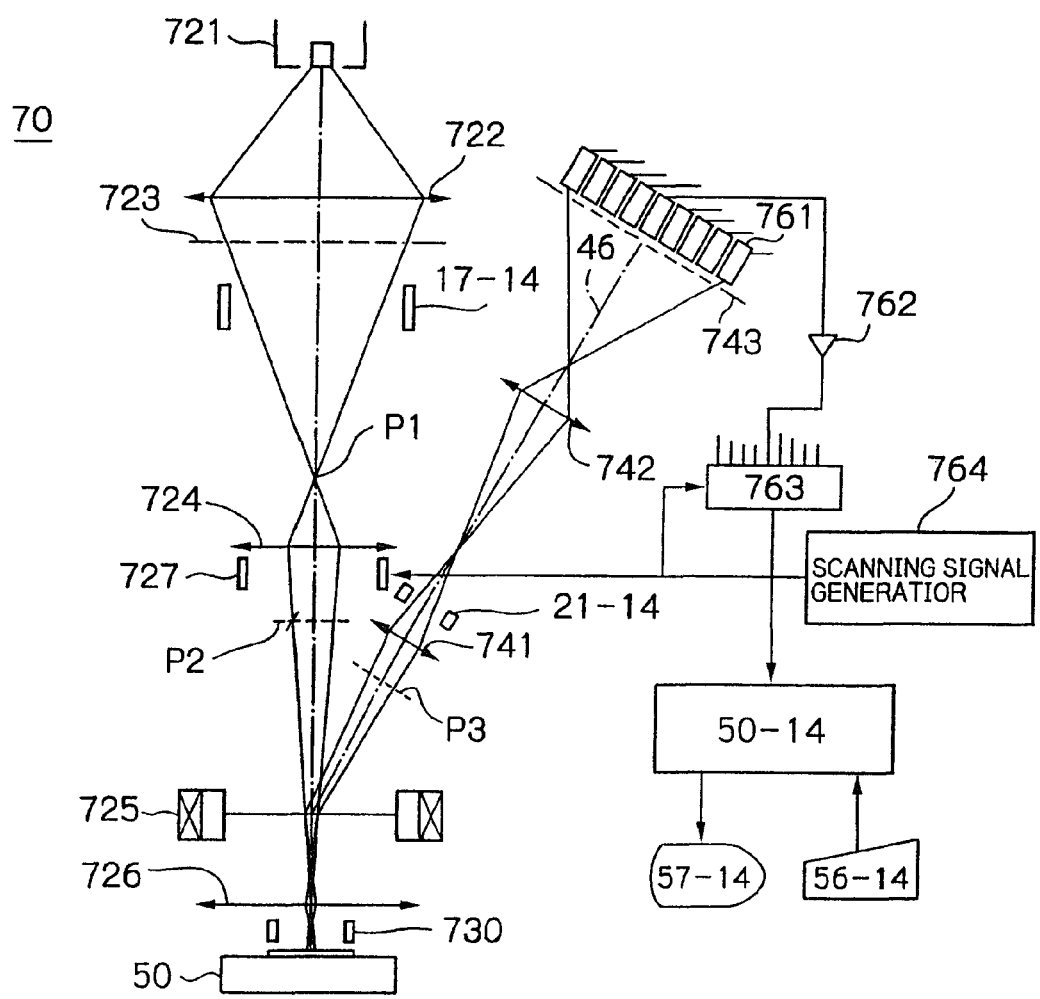
FIG. 56 schematically illustrates further another embodiment of an electron beam apparatus of the present invention.

FIG. 56 illustrates another embodiment of the electron beam apparatus according to the present invention. This embodiment provides an electrostatic deflector 21-14 between the two enlarging lenses 741, 742 in the secondary optical system of the electron beam apparatus illustrated in FIG. 8, and permits an alignment in the enlarging lens 742 by the electrostatic deflector 21-14.

In connection with the electron beam apparatus illustrated in FIG. 56, processing involved in a defect test of a wafer W will be described. It goes without saying that the processing involved in the defect test according to the present invention, described below, can be applied to the electron beam apparatus which uses an electro-optical system of an arbitrary embodiment according to the present invention.

First, before describing the processing involved in the defect test according to the present invention, processing involved in a conventional defect test will be described. Conventionally, the following method has been prevalent.

On a wafer formed with a large number of the same type of dies in design, secondary electron images are compared between the dies. For example, if a secondary electron image of a die detected first is not similar to a secondary electron image of another die detected at the second time (i.e., a difference between the secondary electron images is larger than a reference value), the second die is determined to have a defect if an image of a different die detected at the third time is identical or similar to the first image (i.e., a difference between the secondary electron images is smaller than the reference value).

A similar method can be applied to a mask or a wafer which is formed with two or more type of chips. In this event, secondary electron images are compared for the same corresponding locations on these chips. If a difference is found at the same location as a result of a comparison of one chip with the other, it can be determined that either one is defective.

Also, it is possible to eventually determine whether any chip is defective from a comparison with the same location on the remaining chip.

However, there are several objects under testing which cannot be supported by the conventional defect testing apparatus as follows:

(i) When a mask is to be tested, the mask cannot be tested for defects unless two or more chips are formed on the same substrate. On the other hand, such two-take masks tend to be reduced in future.

(ii) When a test is desired for checking whether or not a correction for a proximity effect was appropriate in a transfer from a mask to a wafer, the detection of defects becomes difficult. This is because even if a corrective effect is inappropriate, similar distortion appears with good reproductivity between adjacent dies, and the presence or absence of defects cannot be determined in a die-to-die relative comparison.

(iii) When it is desired to remove the presence or absence of a problem inherent to a transfer device from a mask to a wafer, for example, connections of stripes overlapping at all times, and the presence or absence of a certain problem on the reproductivity such as a rotation error remaining in a boundary between main fields, it is difficult to detect such defects. This is due to similar reasons to those of the problem (ii).

In a defect testing station according to the present invention, as described below, a defect testing method and apparatus, capable of conducting a defect test based on a relative comparison between different locations in a logically identical form, can detect defects in regions under testing in which the defect test is impossible or difficult with such a relative comparison.

Figure 57:
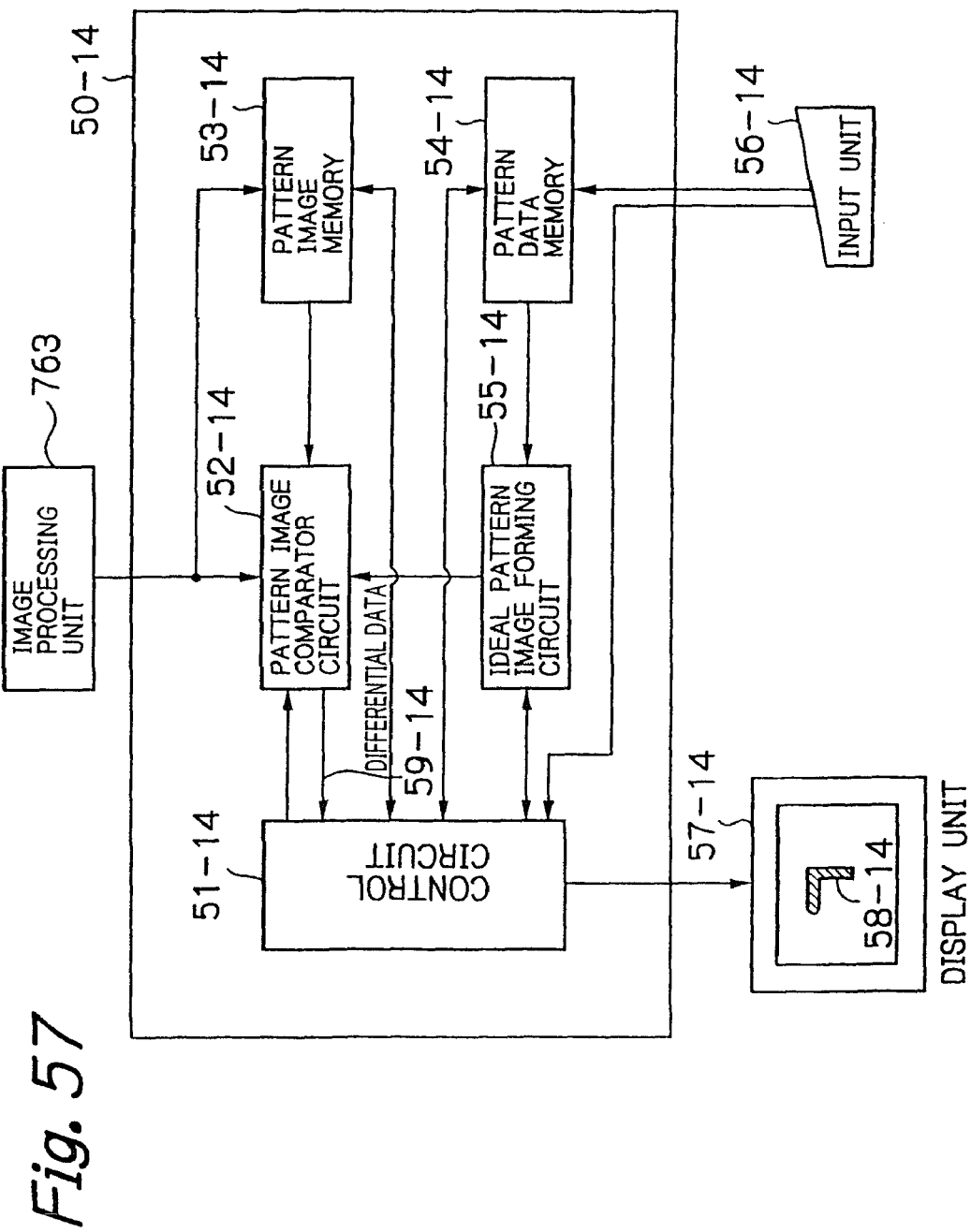
FIG. 57 is a functional block diagram indicating a defect detection means (evaluation means) of the electron beam apparatus shown in FIG. 56.

In FIG. 56, the image processing unit 763 generates a pattern image on the surface of a wafer W based on electric signals from the detectors 761, as described above, and the generated pattern image is supplied to a defect detector 50-14. Functional blocks of the defect detector 50-14 is illustrated in FIG. 57. As illustrated in FIG. 57, the defect detector 50-14 includes a control circuit 51-14 for controlling/managing respective components to determine defects on the wafer W; a pattern image comparator circuit 52-14 for executing a comparison based on secondary electron pattern images; a pattern image memory 53-14 for storing the secondary electron pattern images; a pattern data memory 54-14 for storing pattern data which is logical data of patterns formed on the wafer W; and a logical pattern image forming circuit 55-14 for forming logical pattern images to be compared with an actual secondary electron pattern image.

The pattern image comparator circuit 52-14 has a first mode for comparing secondary electron pattern images at the same locations (for example, dies when a wafer is concerned) on the wafer W in design; and a second mode for comparing an actual secondary electron pattern image at a particular location on the wafer W with a logical pattern image corresponding to that location. The pattern image comparator circuit 52-14 outputs differential data 59-14 indicative of a difference between two images which are compared to the control circuit 51-14. Since the compared images are more similar as the value of the differential data 59-14 is smaller, the control circuit 51-14 can determine matching or unmatching of the two images based on this differential data 59-14. The secondary electron pattern image used by the pattern image comparator circuit 52-14 may be one directly sent from the image processing unit 14-14, or one stored in the pattern image memory 53-14. These pattern images can be arbitrarily switched in a preferred manner.

A display unit 57-14 is connected to the control circuit 51-14 for displaying results of comparisons and determinations, and the like. The display unit 57-14 may be comprised of a CRT, a liquid crystal display, or the like, and can display a defect pattern 58-14, secondary electron pattern images, the number of defective locations, and the like.

The pattern data stored in the pattern data memory 54-14 includes, for example, mask pattern information and the like which is provided from an input unit 56-14 installed outside. This input unit 56-14 can enter instructions of the operator to the defect tester 50-14, and be implemented by a computer which has installed therein software capable of creating pattern data.

Next, the flow of processing involved in the defect detection will be described along a flow chart of FIG. 58. First, a secondary electron image pattern at a location under testing on a wafer W is acquired (step S300). Details on this step will be described later. Next, it is determined whether the wafer W is a wafer or a mask (step S302). When it is a wafer, it is determined whether or not the location under testing is highly susceptible to distortion in pattern formation due to distortion in a transfer optical system in a transfer from a mask to the wafer or due to charge-up when a pattern is formed (a first factor) (step S304). Such a location has been previously mapped in a memory of the control circuit 51-14, or acquired from information from the input unit 56-14.

If the location under testing is highly susceptible to distortion in pattern formation due to the first factor (affirmative determination at step S304), the pattern image comparator circuit 52 compares the secondary electron image pattern at the location under testing with a logical pattern corresponding to that location (second mode) (step S310). After the comparison, differential data 59-14 between both patterns is output to the control circuit 51-14.

If the location under testing is not susceptible to distortion in pattern formation due to the first factor (negative determination at step S304), the flow proceeds to the next determination step S306. In this step, it is determined whether the location under testing is highly susceptible to distortion in pattern formation due to a proximity effect or an incorrect correction for the proximity effect in a transfer from the mask to the wafer, or a defective stripe connection or a defective field connection (second factor) (step S306).

If the location under testing is highly susceptible to the distortion in pattern formation due to the second factor (affirmative determination at step S306), the pattern image comparator circuit 52-14 compares the secondary electron image pattern of the location under testing with the logical pattern corresponding to that location (second mode) in a similar manner (step S310).

If the location under testing is not susceptible to the distortion in pattern formation due to any of the first and second factors (negative determination at step S306), the logically identical locations are compared with each other (first mode) (step S312). As described above, this is a step for comparing the secondary electron image pattern of the location under testing with a secondary electron image pattern at a location, which is a location different from the location of interest, but is formed with a logically identical pattern, to output differential data between the two. With a wafer, a die-to-die comparison is mainly performed in many cases.

On the other hand, if the wafer W is determined to be a mask at step S302, it is determined whether or not this mask is a two-take mask on which two or more of the same type of chips are formed (step S308). With a two-take mask (affirmative determination at step S308), logically identical locations are compared with each other over two or more of identically formed chips (step S312). If the mask is not a two-take mask (negative determination at step S308), it is compared with a logical pattern image (step S310).

After the comparisons as described above, the control circuit 51-14 determines the presence or absence of defects based on the calculated differential data 59-14 (step S314). In a comparison with a logical pattern image, "not defective" is determined when the value of the differential data 59-14 falls within a predetermined threshold value, and "defective" is determined when it exceeds the threshold value.

Figure 59A:
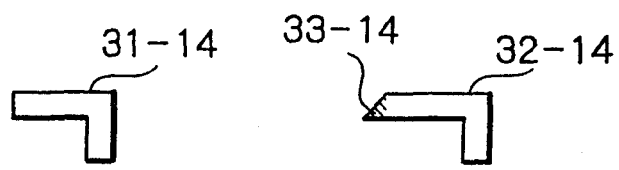
FIG. 59 is an illustration explaining defect detection by means of comparison between dies, measurement of a line width, measurement of voltage contrast in the defect detection process described in FIG. 58.

A determination method for use with the comparison of logically identical locations with each other proceeds as follows. For example, FIG. 59A shows an image 31-14 of a die detected at the first time and an image 32-14 of another die detected at the second time. If it is determined that the die image 31-14 is dissimilar to the die image 32-14 (i.e., the differential data value exceeds the threshold value), and an image of a different die detected at the third time is identical or similar to the first image 31-14 (i.e., the differential data value is equal to or less than the threshold value), it is determined that the second die image 32-14 is defective. When using a more sophisticated comparison and matching algorithm, it is also possible to detect a defective portion 33-14 in the second die image 32-14.

When determining to be defective as a result of the defect determination (affirmative determination at step S316), information on defects is displayed on the display unit 57-14 (step S318). For example, there may be the presence or absence of defects, the number of defects, information on defective locations (positions), and the like. Also, for example, a defective pattern image such as the second die image 32-14 in FIG. 59A may be displayed. In this event, a defective portion may be marked.

Next, it is determined whether or not the wafer W has been tested over the entire region under testing (step S320). When the test is not completed (negative determination at step S320), the flow returns to step S300, from which similar processing is repeated for the remaining region under testing. When the test is completed (affirmative determination at step S320), the defect test processing is terminated.

In the foregoing manner, for testing a wafer for defects in this embodiment, a comparison is first performed on a die-to-die basis for testing (step S312), and then the die is compared with a logical pattern image for a location at which no defect can be detected by such a comparison due to similar defects occurring in the dies (step S310). Since such defects appear in all dies in a distorted region of interest with good reproductivity, it is sufficient to test only one die for the defects in the distorted region at step S310. In the flow chart of FIG. 58, such locations at which reproducible defects may be present are determined at steps S304 and 306.

Further, this embodiment can implement a defect detection for a mask irrespective of whether or not it is a two-take mask.

Figure 58:
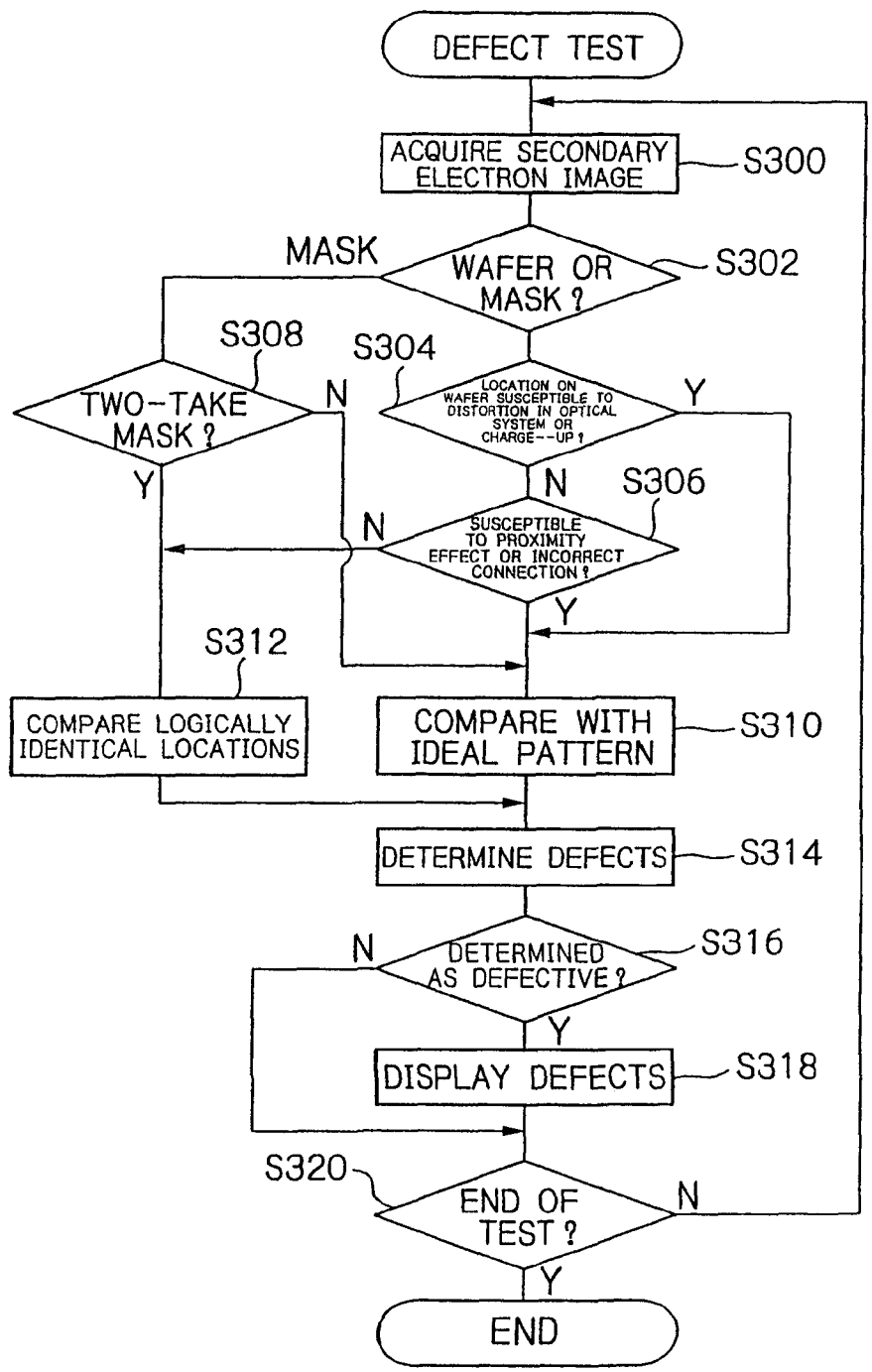
FIG. 58 is a flow chart that depicts the process of detecting defects conducted in an electron beam apparatus concerning the present invention.

Since the secondary electron acquisition process at step S300 in FIG. 58 is similar to the description made in connection with the first embodiment in FIG. 8, description thereon is omitted.

The defect detector 50-14 can also conduct the following defect test.

Figure 59B:
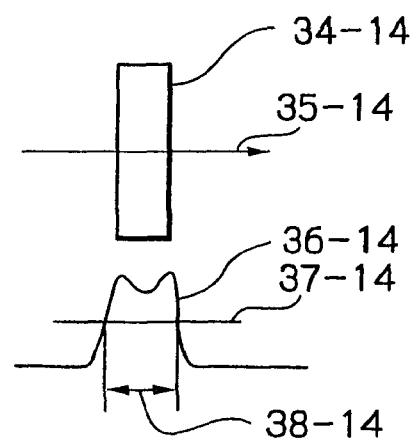

FIG. 59B shows an example of measuring a line width of a pattern formed on a wafer. An actual pattern 34-14 on the wafer is scanned in a direction 35-14 to generate actual secondary electrons, the intensity signal of which is indicated by 36-14. A width 38-14 of a portion in which this signal continuously exceeds a threshold level 37-14 previously determined through calibration can be measured as the line width of the pattern 34-14. If the line width measured in this manner does not fall under a predetermined range, it can be determined that the pattern is defective.

Figure 59C:
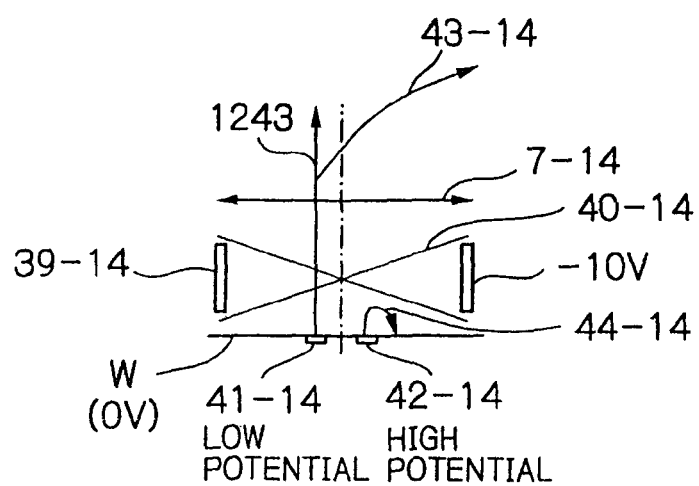

A line width measuring method in FIG. 59C can also be applied to a measurement of an alignment accuracy between respective layers when a wafer W is formed of a plurality of layers. For example, a second alignment pattern formed in the second layer lithography has been previously formed near a first alignment pattern formed in the first layer lithography. The alignment accuracy between the two layers can be determined by measuring the spacing between the two patterns by applying the method in FIG. 59B, and comparing the measured value with a design value. Of course, this method can be applied as well to a wafer formed of three or more layers. In this event, the alignment accuracy can be measured with a minimum amount of scanning if the spacing between first and second alignment patterns is chosen to be substantially equal to a spacing between adjacent beams of a plurality of primary electron beams in the electro-optical system 70.

FIG. 59C shows an example of measuring a potential contrast of a pattern formed on a wafer. In the electro-optical system 70 illustrated in FIG. 56, an axially symmetric electrode 730 is provided between the objective lens 726 and wafer W, and is applied, for example, with a potential of −10V with respect to a potential of 0 V on the wafer. An equi-potential surface at −2 V in this event has a shape as indicated by 40-14 in FIG. 59(c). Assume herein that patterns 41-14 and 42-14 formed on the wafer are at potentials of −4 V and 0 V, respectively. In this event, secondary electrons emitted from the pattern 41-14 have an upward speed corresponding to the motion energy of 2 eV on the equi-potential surface 40-14 at −2V, so that they pass over this potential barrier 40-14, exit the electrode 730 as indicated by a trajectory 43-14, and are detected by the detectors 761. On the other hand, secondary electrons emitted from the pattern 42-14 cannot pass over the potential barrier at −2 V, and are driven back to the surface of the wafer as indicated by a trajectory 44-14, so that they are not detected. As such, a detected image of the pattern 41-14 is bright, while a detected image of the pattern 42-14 is dark. Consequently, a potential contrast can be acquired for the region under testing on the wafer W. The potential of a pattern can be measured from a detected image if the brightness and potential of the detected image have been previously calibrated. Then, a defective portion of the pattern can be detected by evaluating this potential distribution.

In FIG. 56, a blanking deflector 17-14 is provided to deflect primary electron beams to a knife edge shaped beam stopper (not shown) positioned near a cross-over P1 at a predetermined period to repetitively pass the beams only for a short time period and block the beams for the remaining time period, thereby making it possible to create a bundle of beams having a short pulse width. When such beams having a short pulse width are used to measure a potential on a wafer and the like, the operation of a device can be analyzed at a high temporal resolution. In other words, this defect test can be used as a so-called EB tester.

As described above, since the defect test can alternately compare images of different locations in a logically identical form on a sample or compare a logical standard image with an actually generated image, the test can be conducted with a high accuracy and a high throughput irrespective of whether or not potential defects are reproducible. Also, since reproducible defects and non-reproducible defects can be tested with the same apparatus, a foot print of a clean room can be reduced.

Referring to FIGS. 60 through 66, description will be made on the processing for preventing a degraded accuracy for the defect detection even when a misregistration occurs between an image of secondary electron beams acquired by scanning primary electron beams over a region under testing on the surface of a wafer and a previously provided reference image during the defect test processing. Such misregistration constitutes a particularly grave problem when a region irradiated with the primary electron beams deviates from a wafer W to cause a portion of a test pattern to be lost in a detected image of secondary electron beams. This problem cannot be accommodated simply by optimizing a matching region within the detected image. Moreover, this is regarded as a critical disadvantage particularly in a test of highly defined patterns.

Figure 60:
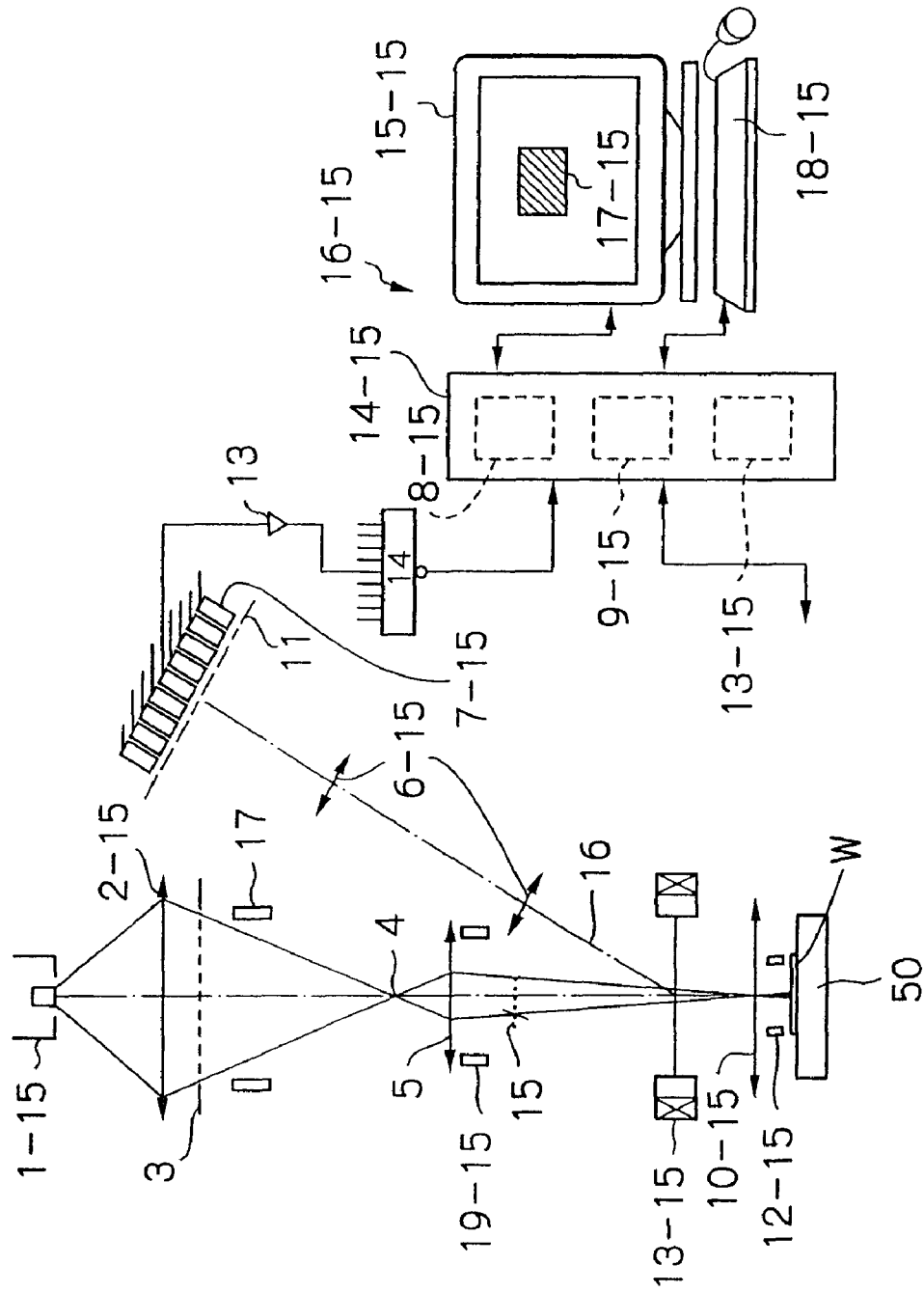
FIG. 60 schematically illustrates still another embodiment of an electron beam apparatus concerning the present invention.

FIG. 60 illustrates a defect detecting apparatus which employs the multi-beam based electro-optical system 70 in the electron beam apparatus illustrated in FIG. 8. This defect testing apparatus is comprised of an electron gun 1-15 for emitting primary electron beams; an electrostatic lens 2-15 for deflecting and reshaping the emitted primary electron beams; an E×B deflector 3-15 for directing the reshaped primary electron beams through a field in which an electric field E is orthogonal to a magnetic field B and substantially perpendicular to a wafer W; an objective lens 10-15 for focusing the primary electron beams on the wafer W; a stage apparatus 50 movable in a horizontal plane with the wafer W carried thereon; an electrostatic lens 6-15 for enlarging secondary electron beams emitted from the wafer W by the irradiation of the primary electron beams; detectors 7-15 for detecting an enlarge image as a secondary electron image of the wafer W; and a controller 16-15 for controlling the entire apparatus and for forming an image from a secondary electron signal detected by the detectors 7 to detect defects on the wafer W based on the image. The controller 16-15 is included in a control unit 2 (FIG. 1). While images based on scattered electrons and reflected electrons, not limited to the secondary electrons, can be acquired as the electron image, described herein is a secondary electron image selected as the electron image.

An axially symmetric electrode 12-15 is additionally interposed between the objective lens 10-15 and wafer W. A control power supply is connected to this axially symmetric electrode 12-15 for controlling a filtering effect of secondary electrons.

The detector 7-15 may be in an arbitrary configuration as long as it can convert secondary electron beams enlarged by the electrostatic lens 6-15 to a signal which can be subsequently processed.

As illustrated in FIG. 60, the controller 6-15 may be implemented by a general-purpose personal computer or the like. This computer comprises a controller body 14-15 for executing a variety of controls and operational processing in accordance with a predetermined program; a monitor 15-15 for displaying results of processing performed by the body 14-15; and an input unit 18-15 such as a keyboard, a mouse and the like for the operator to enter instructions. Of course, the controller 16-15 may be implemented by hardware dedicated to a defect testing apparatus, or a workstation or the like.

The controller body 14-15 is comprised of CPU, RAM, ROM, hard disk, a variety of control boards such as a video board, and the like, not shown. On a memory such as RAM or hard disk, a secondary electron image storage region 8-15 is allocated for storing electric signals received from the detectors 7-15, i.e., digital image data on a secondary electron image of the wafer W. Also, on the hard disk, a reference image storage unit 13-15 exists for previously storing defect-free reference image data on the wafer. The hard disk further stores a defect detection program 9-15, other than a control program for controlling the entire defect testing apparatus, for reading the secondary electron image data from the storage region 8-15 to automatically detect defects on the wafer W in accordance with a predetermined algorithm based on the image data. As described later in greater detail, the defect detection program 9-15 has a function of matching a reference image read from the reference image storage unit 13-15 with an actually detected secondary electron beam image to automatically detect a defective portion, and display an alarm for the operator when determining defective. In this event, the secondary electron image 17-15 may be displayed on the monitor 15-15 for warning.

Figure 61:
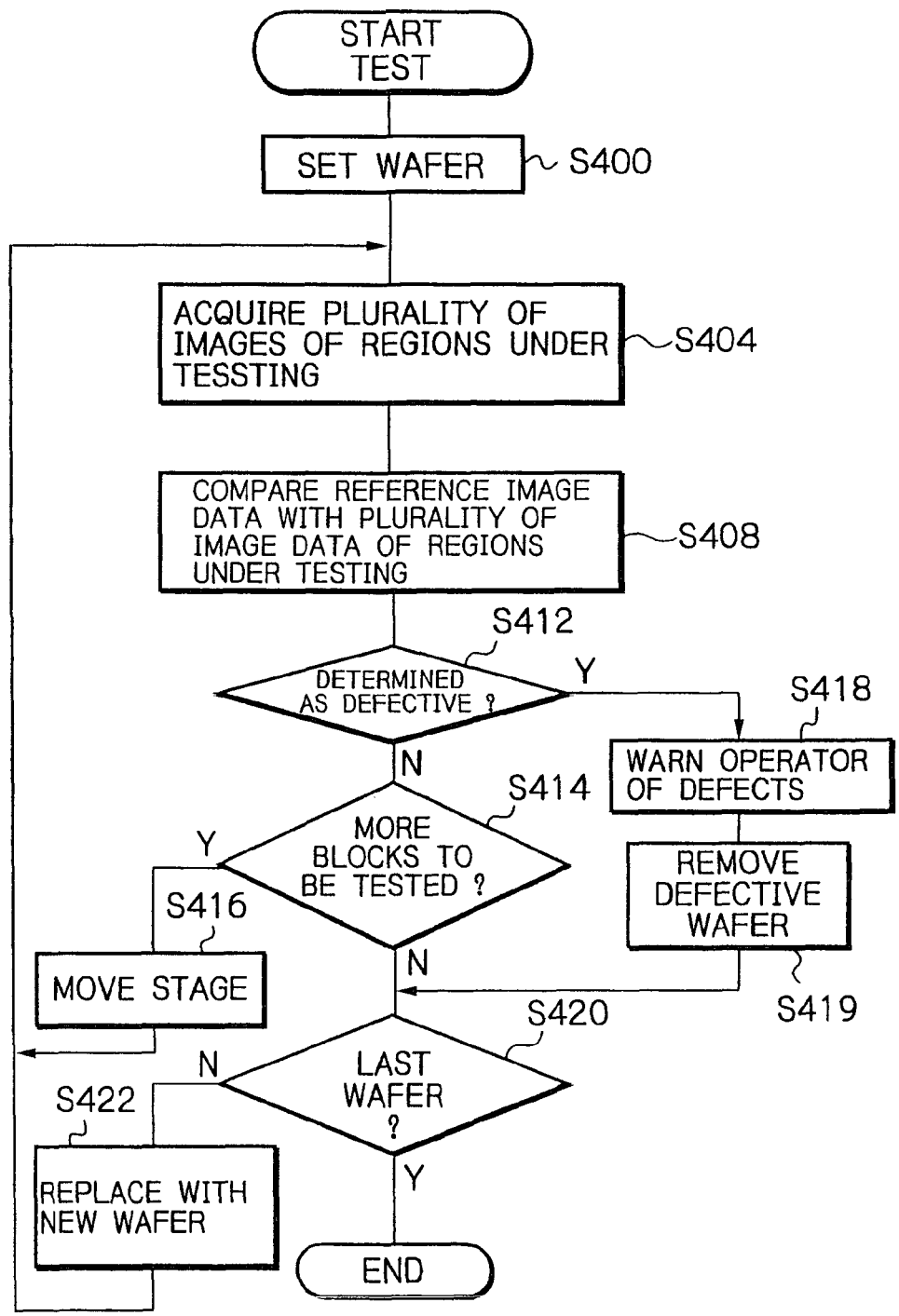
FIG. 61 is a flow chart depicting a main routine in the case of wafer inspection conducted by means of the electron beam apparatus shown in FIG. 60.

In the defect test processing, as illustrated in the flow of a main routine in FIG. 61, a wafer W under testing is first set on the stage apparatus 50 (step S400). This may be performed, as previously illustrated in FIG. 1, by automatically setting a large number of wafers W stored in a loader one by one onto the stage apparatus 50.

Figure 62:
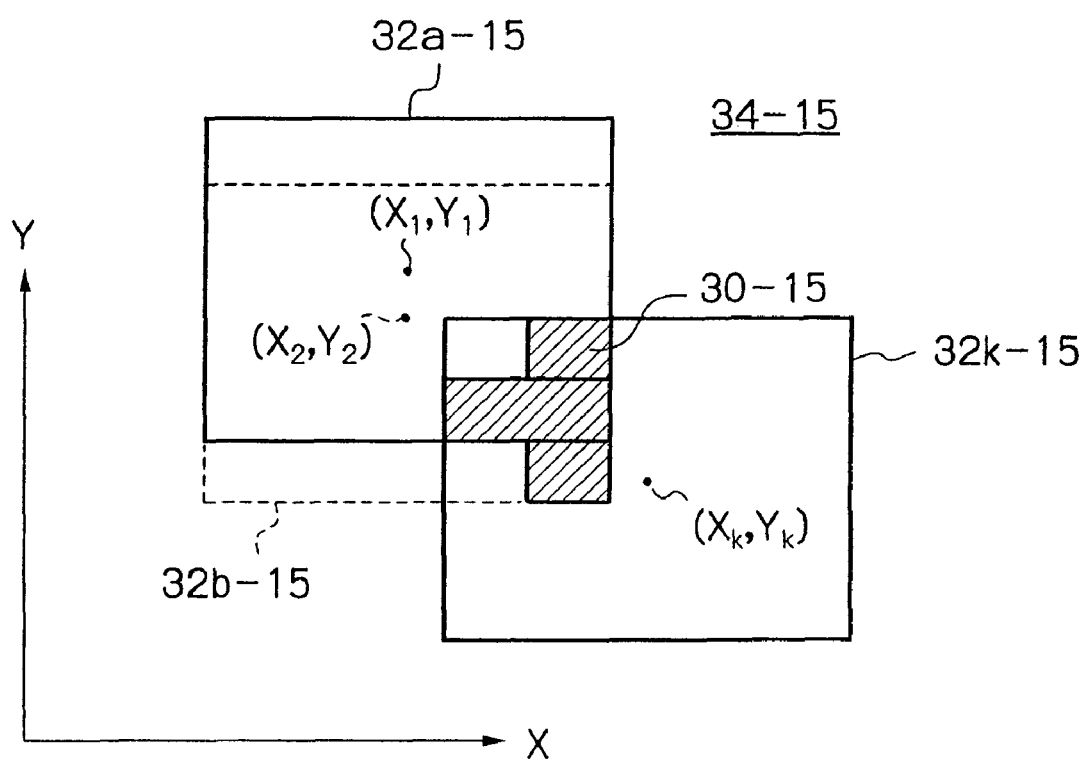
FIG. 62 is a conceptual diagram of a plurality of regions to be inspected, which are staggered and partially overlapped on a wafer.
Figure 63:
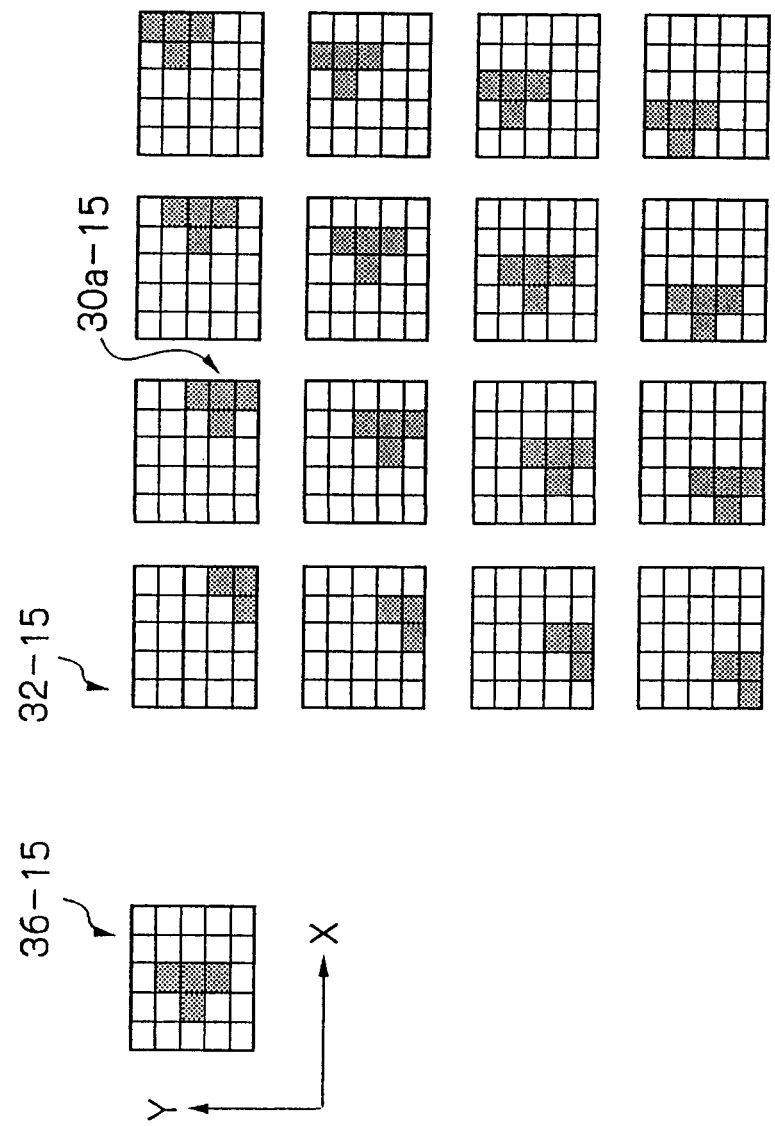
FIG. 63 illustrates a plurality of images to be inspected, which are obtained by an electron beam apparatus concerning the present invention, and a referential image.

Next, the defect testing apparatus acquires each of images of a plurality of regions under testing displaced from one another, while partially overlapping on an X-Y plane on the surface of the wafer W (step S404). As illustrated in FIG. 62, a plurality of regions under testing to be acquired refer to rectangular regions indicated by reference numerals 32-15a, 32-15b, . . . , 32-15k, . . . , for example, on a surface 34-15 under testing of the wafer W, which, as appreciated, are displaced, while partially overlapping one another, around a test pattern 30-15 of the wafer. For example, as illustrated in FIG. 63, assume that 25 images 32-15 (images under testing) of regions under testing have been acquired. In the image illustrated in FIG. 63, a square cell corresponds to one pixel (or a block unit larger than a pixel), and solid black cells of them correspond to image portions of patterns on the wafer. Details on this step S404 will be described later in connection to a flowchart of FIG. 64.

Next, image data on a plurality of regions under testing acquired at step S404 is compared on a one-by-one basis with reference image data stored in the storage unit 13-15 (step S408 in FIG. 61) to determine whether or not defects are present on the surface of the wafer W under testing, which are included in the plurality of regions under testing. This step involves so-called matching between image data, details of which will be described later in connection with a flow chart of FIG. 65.

If it is determined from the result of comparison at step S408 that defects are present on the surface of the wafer W under testing, which are included in the plurality of regions under testing (affirmative determination at step S412), the operator is warned of the existence of the defects (step S418). As a warning method, for example, a message notifying the existence of the defects may be displayed on the monitor 15-15, and simultaneously, an enlarged image 17-15 of the pattern in which the defects exist may be displayed. Such a defective wafer may be immediately removed from a wafer chamber for storage in a different storage location from defect-free wafers W (step S419).

If it is determined from the result of comparison at step S408 that the wafer W is free of defects (negative determination at step S412), it is determined whether or not a region to be tested still remains on the wafer currently under testing (step S414). When a region to be tested still remains (affirmative determination at step S414), the stage 50 is driven to move the wafer W such that another region to be next tested enters a primary electron beam irradiated region (step S416). Then, the flow returns to step 404 to repeat similar processing for the other region.

When no region to be tested remains (negative determination at step S414), or after the defective wafer removing step (step S419), it is determined whether or not the wafer W currently under testing is the last wafer, i.e., whether or not any untested wafer still remains in the loader (step S420). When it is not the last wafer (negative determination at step S420), the tested wafer is stored in a predetermined storage location, and a new untested wafer is set instead on the stage apparatus 50 (step S422). Subsequently, the flow returns to step S404 to repeat similar processing on the new wafer. When it is the last wafer (affirmative determination at step S420), the tested wafer is stored in the predetermined storage location, followed by termination of the entire flow.

Figure 64:
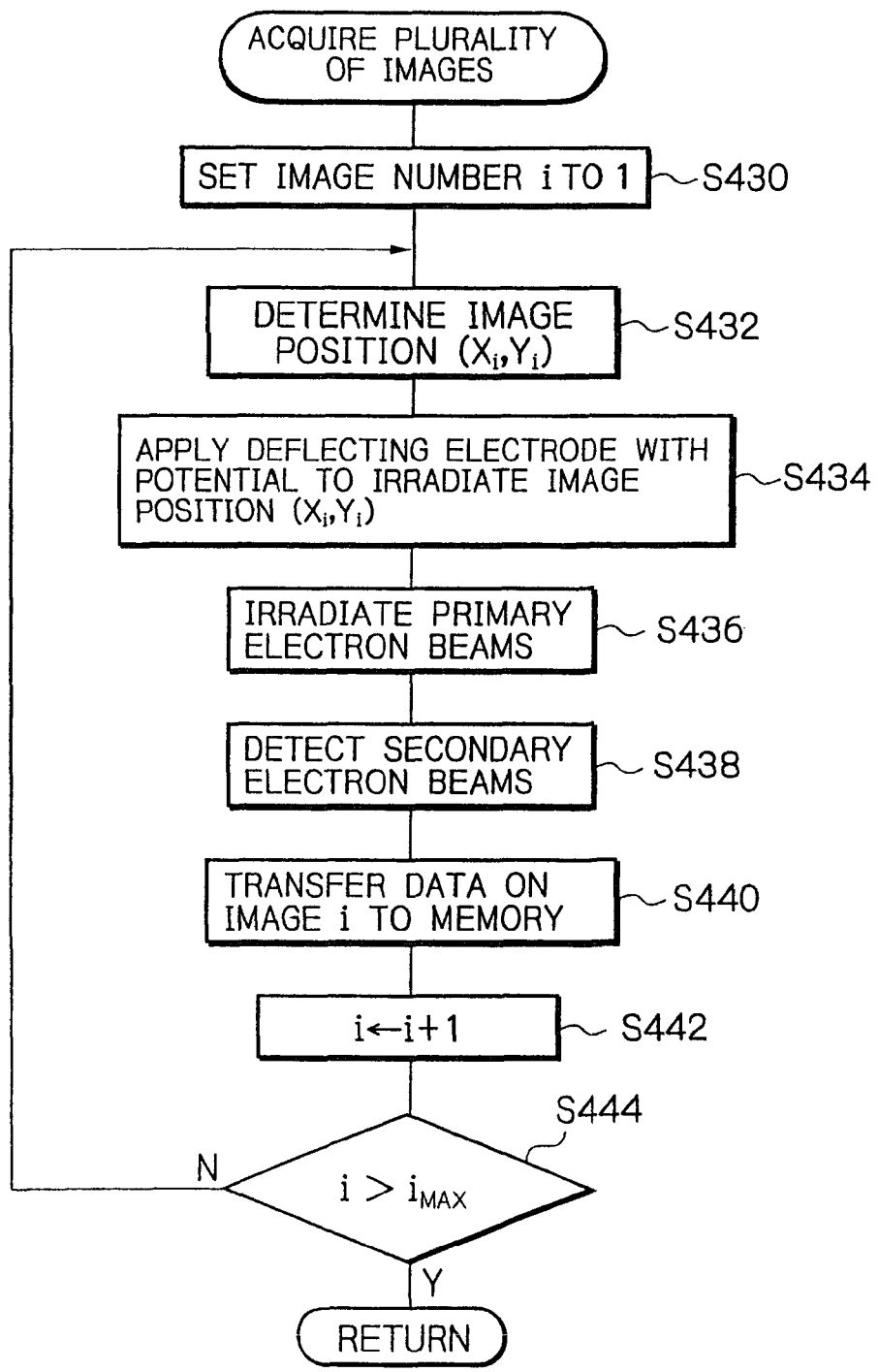
FIG. 64 is a flow chart that depicts the process of obtaining data about an image to be inspected, which is a sub-routine of the main routine indicated in FIG. 61.

Next, the flow of processing at step S404 will be described along the flow chart of FIG. 64. In FIG. 64, an image number i is first set to an initial value "1" (step S430). This image number is an identification number sequentially given to each of a plurality of images of regions under testing. Next, an image position $(X_i, Y_i)$ is determined for the region under testing having the image number i set thereto (step S432). This image position is defined as a particular position within the region for defining the region under testing, for example, the center position within the region. At the current time, since i=1, image position is $(X_1, Y_1)$, which corresponds, for example, to the center position of a region 32a under testing shown in FIG. 62. The image positions have been previously determined for all image regions under testing, and stored, for example, on the hard disk of the controller 16-15, and read at step S432.

Next, the controller 16-15 applies potentials to deflecting electrodes 19-15 and 3-15 such that primary electron beams passing through a deflecting electrode 13-15 in FIG. 60 are irradiated to the image region under testing at the image position $(X_i, Y_i)$ determined at step S432 (step S434 in FIG. 64). Then, primary electron beams, emitted from the electron gun 1-15, pass the electrostatic lens 2-15, E×B deflector 3-15 and objective lens 10-15, and is irradiated to the surface of the set wafer W (step S436). In this event, the primary electron beams are deflected by an electric field crated by the deflecting electrodes 19-15 and 3-15 and irradiated over the entire image region under testing at the image position $(X_i, Y_i)$ on the tested surface 34-15 (FIG. 62) of the wafer W. When the image number i=1, the region under testing is indicated by 32a-15.

Secondary electrons and/or reflected electrons (hereinafter referred only to the "secondary electrons") are emitted from the region under testing irradiated with the primary electron beams. Then, the generated secondary electron beams are focused on the detector 7-15 at a predetermined magnification by the electrostatic lens 6-15 in the enlarging projection system. The detector 7-15 detects the focused secondary electron beams, converts the secondary electron beams to an electric signal, i.e., digital image data for each detected device, and outputs the electric signal (step S438). Subsequently, the digital image data of the detected image number i is transferred to the secondary electron image storage region 8-15 (step S440).

Next, the image number i is incremented by one (step S442), and it is determined whether or not the incremented image number (i+1) exceeds a constant value $i_{MAX}$ (step S444). This $i_{MAX}$ indicates the number of images under testing to be acquired, and is "25" in the aforementioned example in FIG. 63.

When the image number i does not exceed the constant value $i_{MAX}$ (negative determination at step S444), the flow again returns to step S332 to again determine an image position $(X_{i+1}, Y_{i+1})$ for the incremented image number (i+1). This image position is away from the image position $(X_i, Y_i)$ determined in the preceding routine by a predetermined distance $(\Delta X_i, \Delta Y_i)$ in the X direction and/or Y direction. In the example of FIG. 62, the region under testing is located at the position $(X_2, Y_2)$ displaced from $(X_1, Y_1)$ only in the Y direction, and is a square region 32b-15 indicated by a broken line. The value of $(\Delta X_i, \Delta Y_i)$ (i=1, 2, ..., $i_{MAX}$) can be determined as appropriate from data which empirically indicates how long a pattern 30-15 on the surface under testing 34-15 of the wafer W deviates from the field of view of the detector 7-15, and the number and area of regions under testing.

Then, the processing at steps S432-442 is sequentially repeated for the regions under testing at $i_{MAX}$ locations. As illustrated in FIG. 62, these regions under testing are shifted in position, while partially overlapping, on the surface under testing 34-15, such that an image position $(X_k, Y_k)$ after times of movements reaches an image region 32k-15 under testing. In this manner, 25 pieces of image data under testing, illustrated in FIG. 63, are fetched in the image storage region 8-15. It is understood that the plurality of acquired images 32-15 representing the regions under testing (images under testing) partially or completely cover the image 30a-15 of the pattern 30-15 on the surface under testing 34-15 of the wafer W, as illustrated in FIG. 63.

When the incremented image number i exceeds IMAX (affirmative determination at step S444), the flow returns from this subroutine to the comparison step (step S408) in the main routine of FIG. 61.

The image data transferred to the memory at step S440 is comprised of the intensity value (so-called solid data) of the secondary electrons for each pixel detected by the detector 7-15. The image data can be stored in the storage region 8-15 after subjected to a variety of operational processing for matching with a reference image at a later comparison step (step S408 in FIG. 61). Such operational processing may include normalization for unifying the size and/or concentration of image data to the size and/or concentration of reference image data, processing for removing isolated pixel groups which include a predetermined number of pixels or less, regarded as noise, and the like. Further, rather than simple solid data, the image data may have been compressed or converted to a feature matrix which comprises features extracted from a detected pattern to such an extent that the detection accuracy is not degraded for a high definition pattern. Such a feature matrix may be, for example, an m×n feature matrix which comprises as each matrix element the total sum (or normalized value derived by dividing the total sum value by the total number of pixels in the entire region under testing) of secondary electron intensity values of pixels included in each of m×n blocks (m<M, n<N) divided from a two-dimensional region under testing comprised of M×N pixels. In this event, the reference image data is also stored in the same representation as that. The image data herein referred to in the embodiments of the present invention includes image data, the features of which are extracted by an arbitrary algorithm in this manner, not to mention simple solid data.

Figure 65:
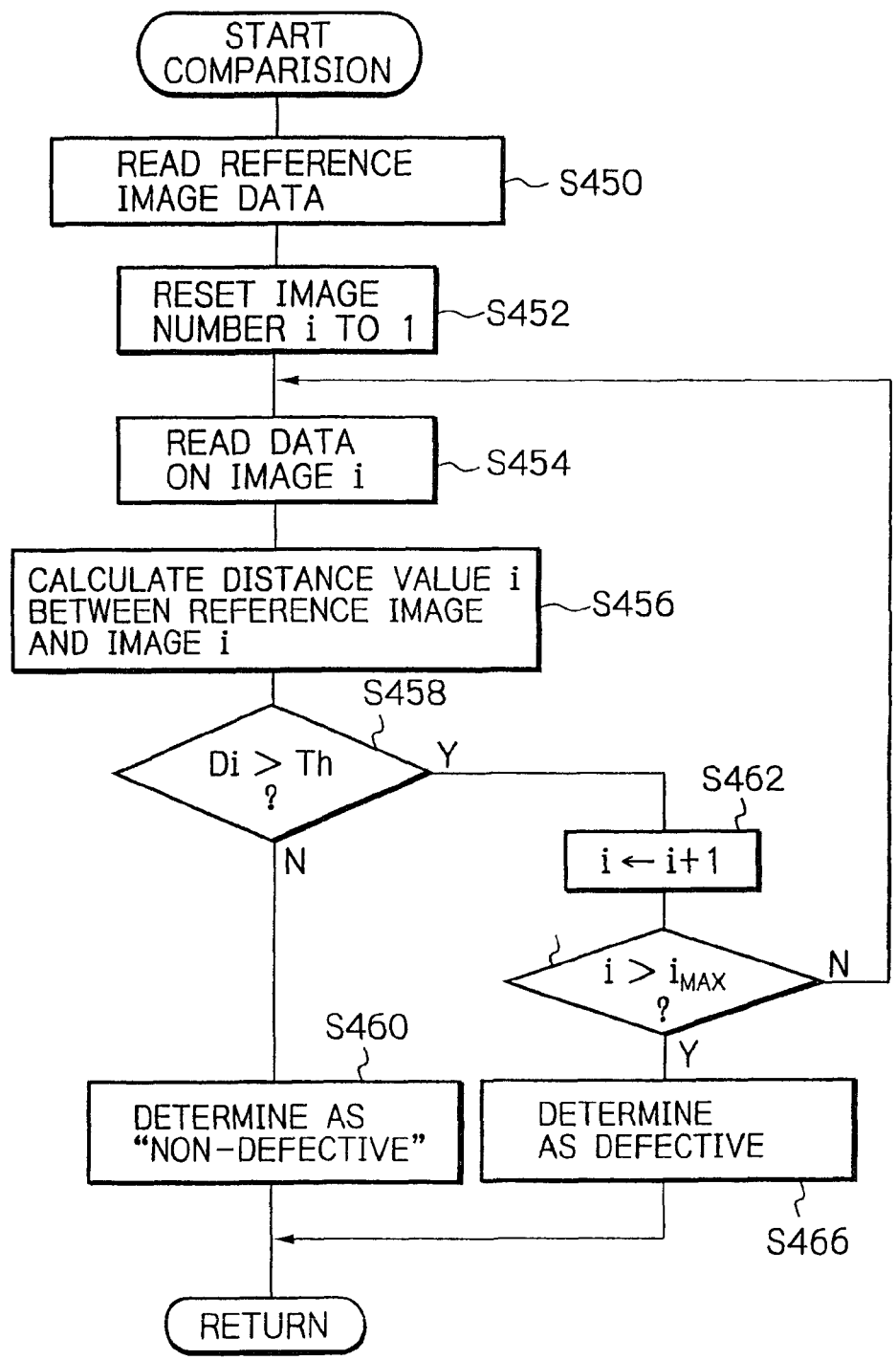
FIG. 65 is a flow chart depicting a comparison process, which is a sub-routine of the main routine indicated in FIG. 61.

Next, the flow of processing at step S408 will be described along the flow chart of FIG. 65. First, the CPU of the controller 16-15 reads reference image data from the reference image storage unit 13-15 into a working memory such as RAM (step S450). This reference image is indicated by reference numeral 36-15 in FIG. 63. Then, the image number i is reset to "1" (step S452), and image data under testing having the image number i is read from the storage region 8-15 into the working memory (step S454).

Next, the read reference image data is matched to the data on the image i to calculate a distance value $D_i$ between the two data (step S456). This distance value $D_i$ represents a similarity between the reference image and the image i under testing, and shows that a difference between the reference image and image under testing is larger as the distance value is larger. Any amount may be employed as the distance value $D_i$ as long as it represents the similarity. For example, when image data is comprised of M×N pixels, the secondary electron intensity (or feature amount) of each pixel is regarded as each position vector component of an M×N-dimensional space, and the Euclidean distance between a reference image vector and an image i vector on the M×N-th dimensional space, or a correlation coefficient may be calculated. Of course, a distance other than the Euclidean distance, for example, a so-called urban land distance and the like may be calculated. Further, when the number of pixels is large, the amount of calculations becomes immense, so that the distance value between image data represented by an m×n feature vector may be calculated, as described above.

Next, it is determined whether or not the calculated distance value $D_i$ is smaller than a predetermined threshold value Th (step S458). This threshold value Th is experimentally found as the basis for determining sufficient matching between the reference image and image under testing. When the distance value $D_i$ is smaller than the predetermined threshold value Th (affirmative determination at step S458), the surface under testing 34-15 of the wafer W is determined as "non defective" (step S460), followed by the subroutine returning to the main routine. Specifically, if any of images under testing substantially matches the reference image, the surface under testing is determined as "non defective." Since all images under testing need not undergo the matching in this manner, fast determination is possible. In the example of FIG. 63, it can be seen that images under testing at the third row, third column do not shift in position from the reference image and substantially match the same.

When the distance value $D_i$ is equal to or larger than the predetermined threshold Th (negative determination at step S458), the image number i is incremented by one (step S462), and it is determined whether or not the incremented image number (i+1) exceeds the constant value $i_{MAX}$ (step S464).

When the image number i does not exceed the constant value $i_{MAX}$ (negative determination at step S464), the flow returns again to step S354, where image data is read for the incremented image number (i+1), and similar processing is repeated. On the other hand, when the image number i exceeds the constant value $i_{MAX}$ (affirmative determination at step S464), the surface under testing 34-15 of the wafer W is determined as "defective" (step S466), followed by the flow returning from this subroutine. Specifically, when none of the images under testing substantially matches the reference image, the surface under testing 34-15 of the wafer W is determined as "defective."

While FIG. 60 shows an example in which the electro-optical system of the first embodiment is used to conduct a defect test, it goes without saying that a mapping type electron beam apparatus in other embodiments may be utilized, not limited to the scanning type first embodiment.

In this event, the image position $(X_i, Y_i)$ at step S432 in FIG. 64 corresponds to the center position of a two-dimensional image which is a combination of a plurality of line images acquired by scanning multiple beams. This image position $(X_i, Y_i)$ is sequentially changed in subsequent steps by changing an offset voltage of the deflector 727 (FIG. 8), by way of example. The deflector 727 changes a voltage around a set offset voltage to perform normal line scanning. Of course, a deflection device different to from the deflector 727 may be provided to change the image position $(X_i, Y_i)$.

As described above, since a plurality of images of regions under testing mutually displaced while partially overlapping on a sample are acquired and compared with a reference image to detect defects, it is possible to prevent a degraded test accuracy due to the positions of the images under testing and the reference image.

Figure 66:
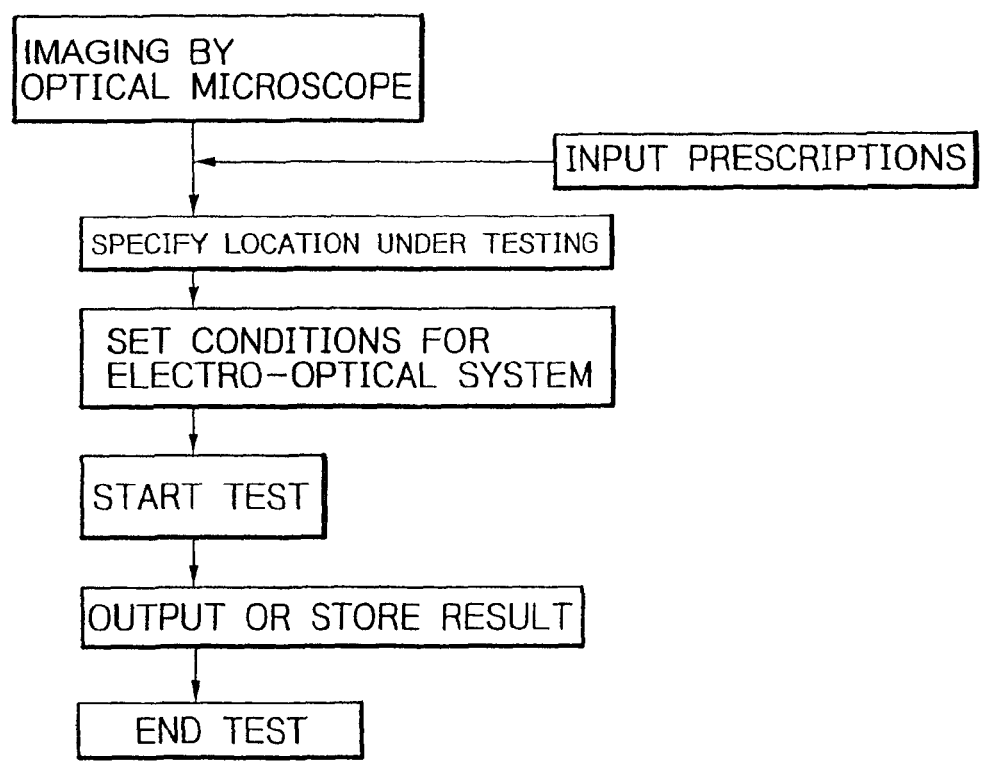
FIG. 66 is a flow chart that depicts the process of inspection (evaluation) concerning the present invention.

As previously described in connection with FIG. 1, a wafer to be tested is carried by an atmospheric conveyance system and a vacuum conveyance system, aligned on a high precision X-Y stage, and then fixed by an electrostatic chuck mechanism or the like, followed by a defect test and the like in accordance with a procedure of FIG. 66. As illustrated in FIG. 66, first, an optical microscope is used to confirm the positions of respective dies and detect the heights of respective locations as required, to store data. The optical microscope is also used to acquire optical microscopic images of sites at which defects and the like are preferably monitored for comparison with electron beam images, and the like. Next, the apparatus is applied with information on prescriptions in accordance with the type of wafer (after which process, whether the size of the wafer is 20 cm or 30 cm, and the like). Subsequently, after specifying locations to be tested, setting the electro-optical system, and setting testing conditions and the like, the wafer is tested for defects in real time while images are acquired. A high-speed information processing system comprising algorithms conducts the test through comparison of cells, comparison of dies and the like, and outputs the result of test to a CRT or the like, and stores the result in a storage device, as required. Defects include particle defects, abnormal shape (pattern defect), electric defects (disconnected wires, vias and the like, defective conduction, and the like), and the like. The information processing system is capable of automatically distinguishing such defects from one another, classifying the defects by size, and sorting out killer defects (grave defects which disable the use of a chip, and the like) in real time. The detection of electric defects can be achieved by detecting abnormal contrast. For example, irradiation of an electron beam (approximately 500 eV) to a defectively conducting location can result in distinction from normal locations because such location is generally charged in positive to cause lower contrast. An electron irradiating apparatus used herein refers typically to a low-potential energy electron beam irradiator (generation of thermal electron, UV/photoelectron) provided separately from an electron beam irradiating apparatus for testing in order to emphasize the contrast by potential difference. Before irradiating a region under testing with an electron beam for testing, this low-potential energy electron beam is generated for irradiation. For an image projection system which can positively charge an object under testing simply by irradiating the electron beam for testing, the low-potential electron beam irradiator need not be provided in separation depending on a particular use. Defects can also be detected from a difference in contrast (caused by a difference in the ease of flow in the forward direction and opposite direction of a device) by applying a wafer with a positive or negative potential with respect to a reference potential. This can be utilized in a line width measuring apparatus and an aligner.

As the electro-optical system 70 operates, floating target substances are attracted to a high voltage region due to a mutual proximity effect (charging of particles near the surface), so that organic materials are deposited on a variety of electrodes used for forming and deflecting electron beams. Since insulating materials gradually deposited on surfaces due to charging in this manner adversely affect the formation of electron beams and the deflecting mechanism, the deposited insulating materials must be removed on a periodic basis. The periodic removal of insulating materials can be carried out by utilizing electrodes near regions on which insulating materials are deposited to create a plasma of hydrogen, oxygen or fluorine, and a compound including them, such as HF, $O_2$, $H_2O$, $C_MF_M$ in vacuum, maintaining a plasma potential within the space at a potential at which sputter is generated on the surfaces of the electrodes (several kV, for example, 20-50 kV), and removing only organic substances through oxidization, hydronization or fluorination.

Next, explanation will be made on a method of manufacturing semiconductor devices which includes procedures for evaluating the semiconductor wafers in the middle of a manufacturing process or after the process using the electron beam apparatus of the present invention.

Figure 67:
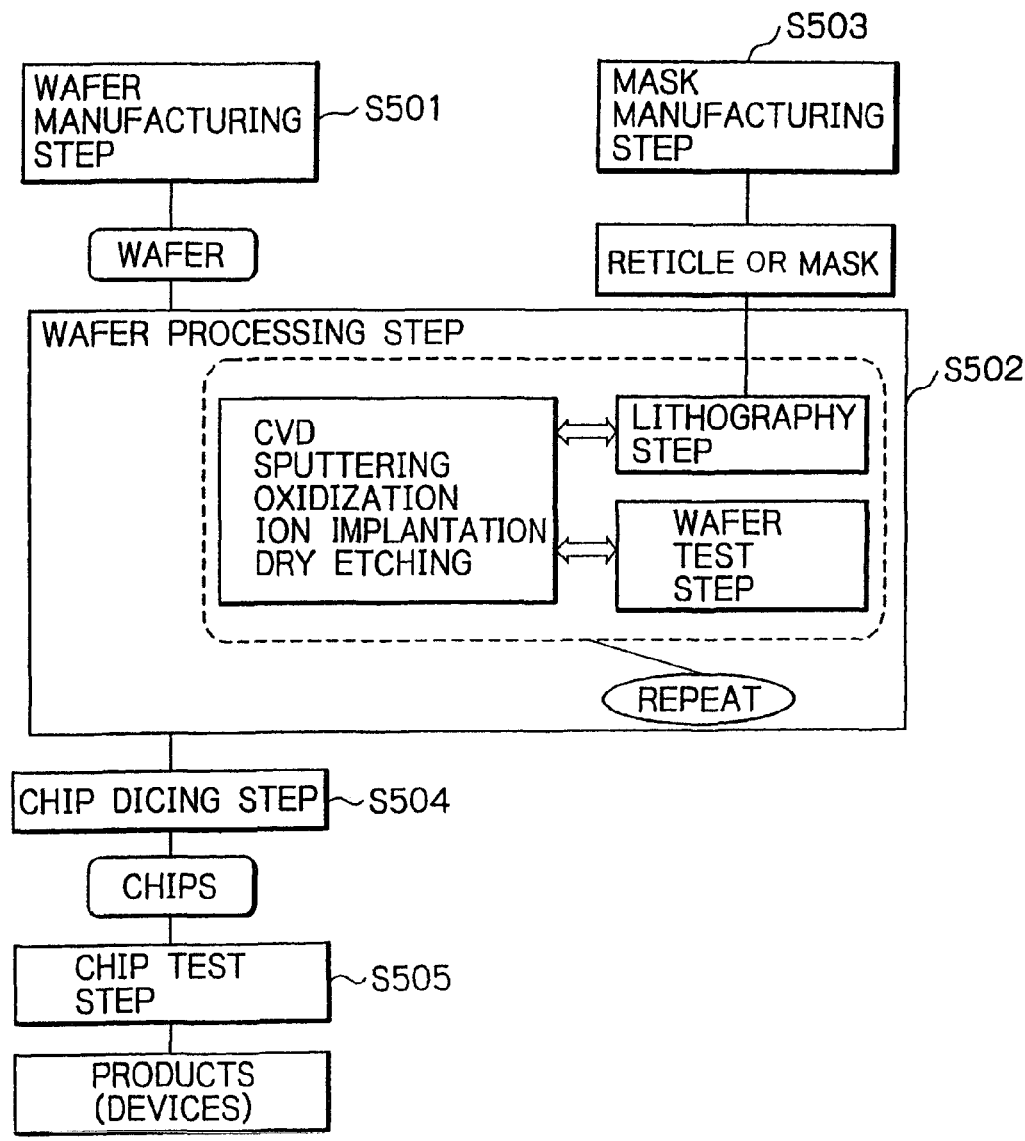
FIG. 67 is a flow chart depicting a method of fabricating a semiconductor device concerning the present invention.

As illustrated in FIG. 67, the method of manufacturing semiconductor devices, when generally divided, comprises a wafer manufacturing step S501 for manufacturing wafers; a wafer processing step S502 for processing wafers as required; a mask manufacturing step S503 for manufacturing masks required for exposure; a chip assembly step S504 for dicing chips formed on a wafer one by one and bringing each chip into an operable state; and a chip testing step S505 for testing finished chips. Each of the steps may include several sub-steps.

In the respective steps, a step which exerts a critical influence to the manufacturing of semiconductor devices is the wafer processing step S502. This is because designed circuit patterns are formed on a wafer, and a multiplicity of chips which operate as a memory and MPU are formed in this step.

It is therefore important to evaluate a processed state of a wafer executed in sub-steps of the wafer processing steps which influences the manufacturing of semiconductor devices. Such sub-steps will be described below.

First, a dielectric thin film serving as an insulating layer is formed, and a metal thin film is formed for forming wires and electrodes. The thin films are formed by CVD, sputtering or the like. Next, the formed dielectric thin film and metal thin film, and a wafer substrate are oxidized, and a mask or a reticle created in the mask manufacturing step S503 is used to form a resist pattern in a lithography step. Then, the substrate is processed in accordance with the resist pattern by a dry etching technique or the like, followed by injection of ions and impurities. Subsequently, a resist layer is stripped off, and the wafer is tested.

The wafer processing step as described is repeated the number of times equal to the number of required layers to form a wafer before it is separated into chips in the chip assembly step S504.

Figure 68:
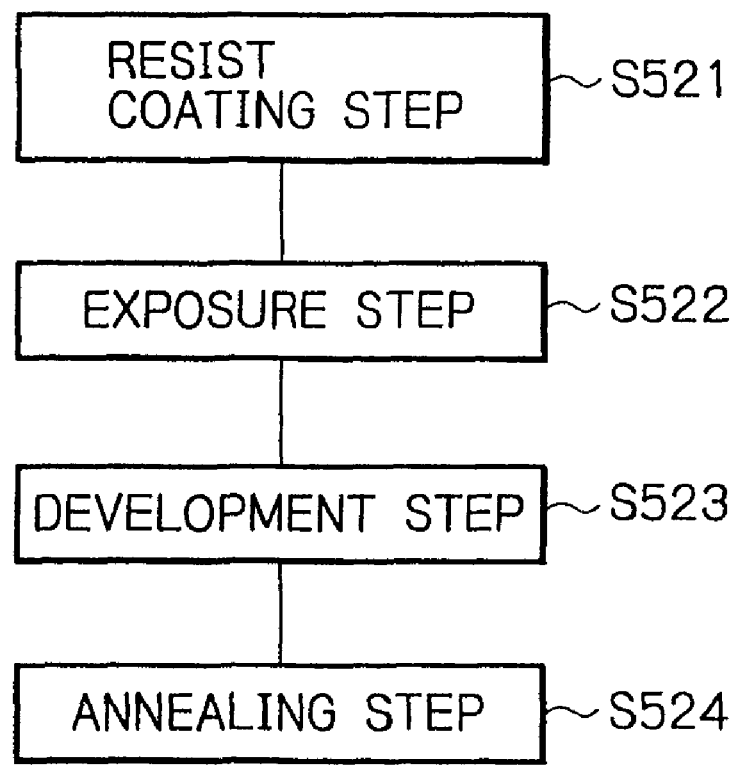
FIG. 68 is a flow chart depicting the details of the lithography process indicated in FIG. 67.

FIG. 68 is a flow chart illustrating the lithography step which is a sub-step of the wafer processing step in FIG. 67. As illustrated in FIG. 69, the lithography step includes a resist coating step S521, an exposure step S522, a development step S523, and an annealing step S524.

After a resist is coated on a wafer formed with circuit patterns using CVD or sputtering in the resist coating step S521, the coated resist is exposed in the exposure step S522. Then, in the development step S523, the exposed resist is developed to create a resist pattern. In the annealing step S524, the developed resist pattern is annealed for stabilization. These steps S521 through S524 are repeated the number of times equal to the number of required layers.

In the process of manufacturing semiconductor devices, a test is conducted for defects and the like after the processing step which requires the test. However, the electron beam based defect testing apparatus is generally expensive and is low in throughput as compared with other processing apparatuses, so that the defect testing apparatus is preferably used after a critical step which is considered to most require the test (for example, etching, deposition (including copper plating), CMP (chemical mechanical polishing), planarization, and the like).

As described above, according to the present invention, since semiconductor devices are manufactured while they are tested for defects and the like after termination of each step or sub-step, which requires the test, using a multi-beam based electron beam apparatus which presents a high throughput, the semiconductor devices themselves can be manufactured at a high throughput. It is therefore possible to improve the yield rate of products and prevent defective products from being shipped.

What is claimed is:

1. An electron beam apparatus for irradiating a sample with a primary electron beam, and detecting secondary electrons generated from a surface of the sample by the irradiation to evaluate the sample surface, comprising:
   a primary electro-optical system for focusing the primary electron beam on the sample surface and scanning it with the primary electron beam;
   a secondary electro-optical system comprising at least one stage of lens;
   an E×B separator for separating the secondary electrons generated from the sample surface and directing them to the secondary electro-optical system;
   a first detector for detecting the secondary electrons which have passed through the secondary electro-optical system;
   a second detector for detecting an exposure dose of the primary electron beam on the sample surface;
   a memory for storing the detected exposure doses on the sample surface; and
   a control apparatus adapted to calculate a unit exposure dose per unit area on the basis of the stored exposure doses, and controlling the primary electron beam such that the unit exposure dose does not exceed a predetermined level.

2. An electron beam apparatus according to claim 1, wherein the secondary electro-optical system further comprises a diaphragm.

3. An electron beam apparatus according to claim 1, wherein the primary electro-optical system comprises an aperture plate having a plurality of apertures by which a plurality of primary electron beams are formed from an electron beam emitted from an electron gun.

4. An electron beam apparatus according to claim 1, further comprising an apparatus for outputting a signal representing a position on the sample surface, at which the unit exposure dose exceeds the predetermined level.

5. An electron beam apparatus according to claim 1, wherein
   the sample is a wafer;
   the electron beam apparatus further comprises an evaluation apparatus for evaluating the wafer surface on the basis of the detected secondary electrons, the evaluation being executed for every constant stripe width on the wafer while a stage carrying wafer is moving; and
   the calculation of the unit exposure dose is executed for an area which is smaller than an area of (the stripe)×(a length of a chip in the stripe direction).

6. An electron beam apparatus according to claim 1, further comprising:
   a third detector for detecting a moving speed of a sample stage;
   a compensation apparatus included in at least one of the primary electro-optical system and the secondary electro-optical system, for compensating, in response to the moving speed of the sample stage detected by the third detector, a deflection amount of at least one of the primary electron beam and the secondary electron beam.

7. An electron beam apparatus according to claim 1, further comprising:

a third detector for detecting a moving speed of a stage carrying the sample;

a fourth detector for detecting a position of the stage;

a compensation apparatus included in at least one of the primary electro-optical system and the secondary electro-optical system, for compensating, in response to the moving speed and the position of the sample stage detected by the third and fourth detectors, a deflection amount of at least one of the primary electron beam and the secondary electron beam.

8. An electron beam apparatus according to claim 1, wherein the primary electron beam is irradiated on the sample surface in the form of a multi-beam; and the minimum interval between adjacent primary electron beams on the sample surface is wider than the resolution of the secondary electro-optical system.

9. An electron beam apparatus according to claim 1, wherein the primary electron beam is irradiated on the sample surface in the form of a multi-beam; and the multi-beam is set such that when the beams on the sample surface are projected onto an axis perpendicular to a moving direction of a sample stage, the projected points on the axis are spaced at substantially the same interval.

* * * * *

UNITED STATES PATENT AND TRADEMARK OFFICE
CERTIFICATE OF CORRECTION

| | | |
|---|---|---|
| PATENT NO. | : 7,888,642 B2 | |
| APPLICATION NO. | : 12/188567 | |
| DATED | : February 15, 2011 | |
| INVENTOR(S) | : Mamoru Nakasuji et al. | |

It is certified that error appears in the above-identified patent and that said Letters Patent is hereby corrected as shown below:

On the title page:
In Item 75, second Inventor name;
Change
"Nabuharu Noji"

To be

--Nobuharu Noji--

Signed and Sealed this
Ninth Day of August, 2011

David J. Kappos
*Director of the United States Patent and Trademark Office*